United States Patent [19]

Kohsaka et al.

[11] Patent Number: 4,645,765
[45] Date of Patent: Feb. 24, 1987

[54] TETRACYCLO COMPOUNDS AND A PHARMACEUTICAL COMPOSITION CONTAINING THE SAME

[75] Inventors: Masanobu Kohsaka, Sakai; Hiroshi Terano, Toyonaka; Tadaaki Komori, Takatsuki; Morita Iwami, Takarazuka; Michio Yamashita, Takarazuka; Masashi Hashimoto, Takarazuka; Itsuo Uchida, Kyoto; Shigehiro Takase, Nishinomiya, all of Japan

[73] Assignee: Fujisawa Pharmaceutical Co., Ltd., Osaka, Japan

[21] Appl. No.: 743,616

[22] Filed: Jun. 11, 1985

[30] Foreign Application Priority Data

Jun. 25, 1984 [GB] United Kingdom ............... 8416141
Apr. 24, 1985 [GB] United Kingdom ............... 8510378

[51] Int. Cl.$^4$ ............... A61K 31/535; C07D 498/18
[52] U.S. Cl. ............... 514/233; 514/234; 514/236; 514/237; 514/239; 544/63; 544/73
[58] Field of Search ............... 544/63, 73; 514/233, 514/234, 236, 237, 239

[56] References Cited

U.S. PATENT DOCUMENTS 3,193,557 7/1965 Jones et al. ............... 544/63 X

OTHER PUBLICATIONS

Revised Absolute Configuration of Mitomycin C., Shirahata, K.; Hirayama, N. J. Am. Chem. Soc. 105, 7199, (1983).

Primary Examiner—Richard L. Raymond
Attorney, Agent, or Firm—Oblon, Fisher, Spivak, McClelland & Maier

[57] ABSTRACT

New tetracyclo compounds of the formula:

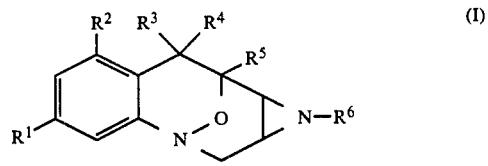

in which
$R^1$ is formyl, protected formyl, hydroxymethyl, protected hydroxymethyl, arylaminomethyl, carboxy, protected carboxy or substituted iminomethyl,
$R^2$ is hydroxy, alkoxy or protected hydroxy,
$R^3$ is hydrogen and $R^4$ is methyl, hydroxymethyl or protected hydroxymethyl, or
$R^3$ and $R^4$ are combined together to form methylene or oxo,
$R^5$ is hydroxy, alkoxy or protected hydroxy, and
$R^6$ is hydrogen, imino-protective group or alkyl, and pharmaceutically acceptable salts thereof, which have pharmacological activities such as antitumor activity, antimicrobial activity, and the like, and a process for their production and a pharmaceutical composition containing the same.

15 Claims, 2 Drawing Figures

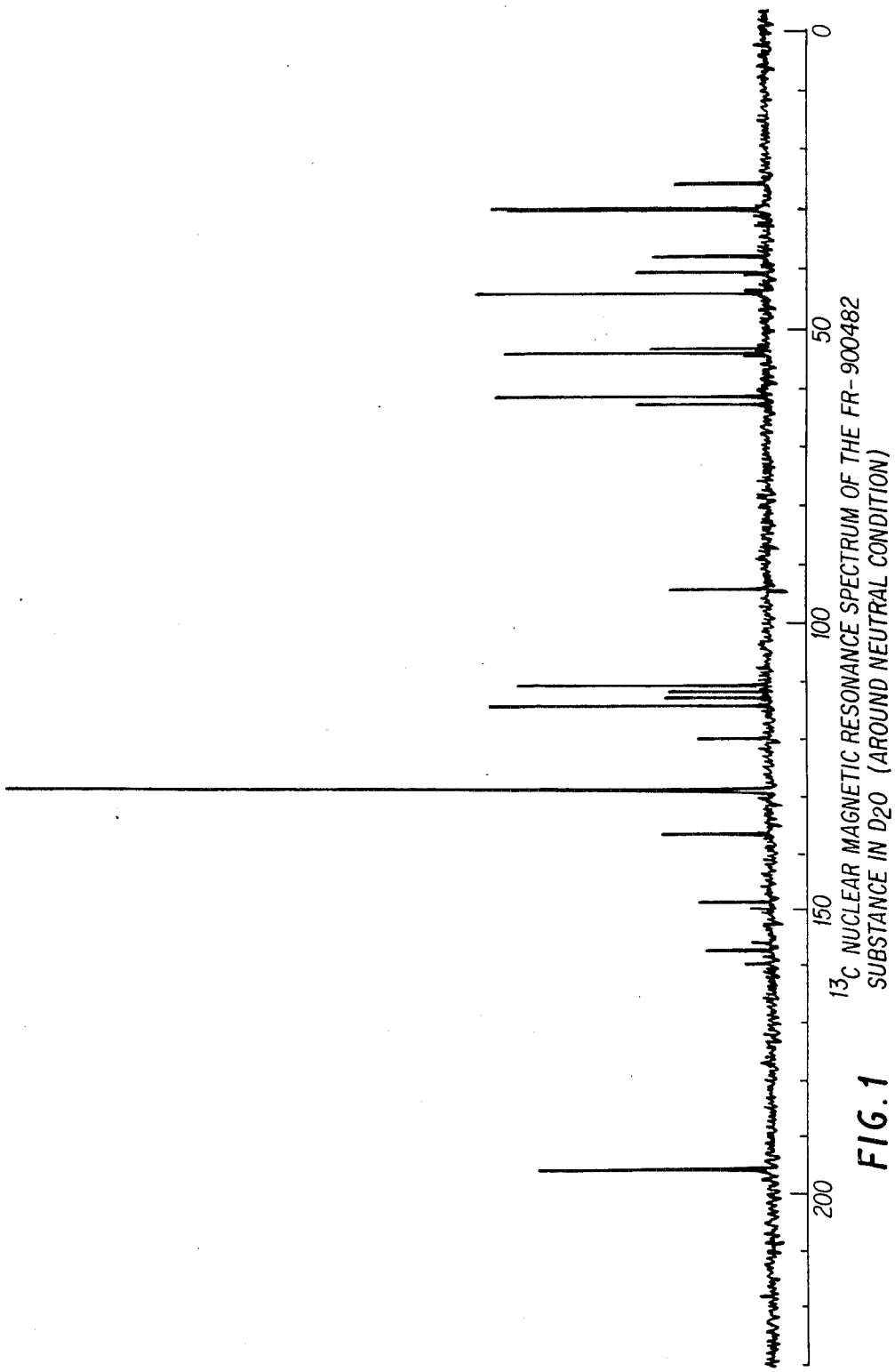

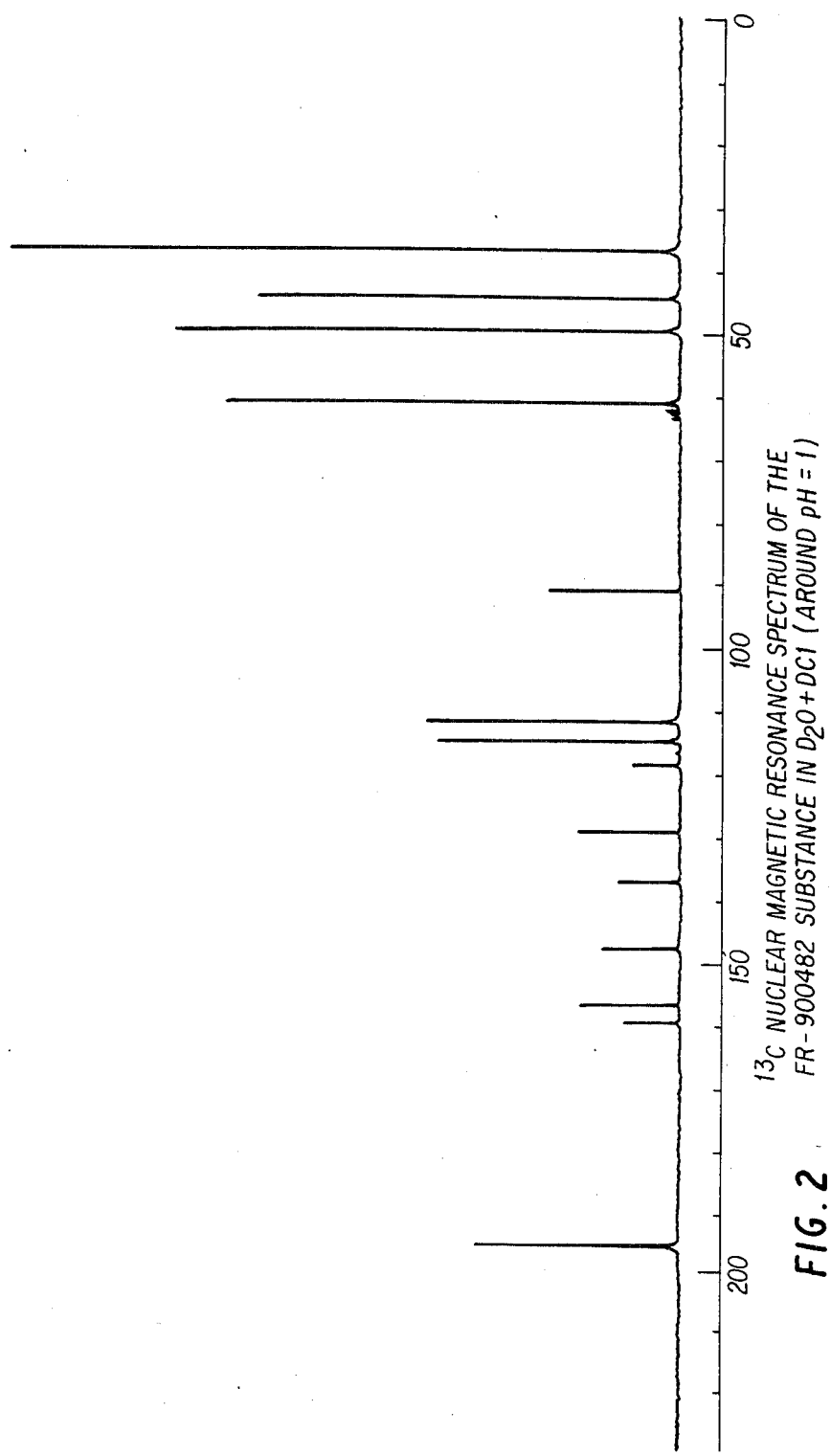
FIG. 2 13C NUCLEAR MAGNETIC RESONANCE SPECTRUM OF THE FR-900482 SUBSTANCE IN D₂O+DCl (AROUND pH=1)

TETRACYCLO COMPOUNDS AND A PHARMACEUTICAL COMPOSITION CONTAINING THE SAME

This invention relates to new tetracyclo compounds. More particularly, this invention relates to new tetracyclo compounds and pharmaceutically acceptable salts thereof, which have pharmacological activities, to a process for their production, to a pharmaceutical composition containing the same and to a use thereof for manufacture of medicaments.

Accordingly, one object of this invention is to provide new tetracyclo compounds and pharmaceutically acceptable salts thereof, which have pharmacological activities such as antitumor activity, antimicrobial activity, and the like.

Another object of this invention is to provide a process for production of the tetracyclo compounds or salts thereof which comprises a fermentation process and a synthetic process.

A further object of this invention is to provide a pharmaceutical composition containing, as active ingredients, the tetracyclo compounds or pharmaceutically acceptable salts thereof.

Still further object of this invention is to provide a use of the tetracyclo compounds and pharmaceutically acceptable salts thereof for manufacture of medicaments for treatments of tumors, infectious diseases, and the like.

In the appended drawings

FIG. 1 illustrates the nuclear magnetic resonance spectrum of FR-900482 in $D_2O$, and FIG. 2 illustrates the spectrum in $D_2O + DCl$.

With respect to the present invention, it is to be noted that this invention is originated from and based on the first and new discovery of the new certain specific compound, FR-900482 substance. In more detail, the FR-900482 substance was firstly and newly isolated in pure form from a culture broth obtained by fermentation of a new species belonging to genus Streptomyces.

And, as a result of an extensive study for elucidation of chemical structures of the FR-900482 substance and its triacetyl derivative, the inventors of this invention have succeeded in determining the chemical structures thereof and in producing the tetracyclo compounds of this invention.

The new tetracyclo compounds of this invention can be represented by the following general formula:

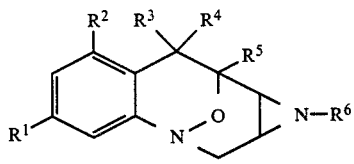

in which
$R^1$ is formyl, protected formyl, hydroxymethyl, protected hydroxymethyl, arylaminomethyl, carboxy, protected carboxy or substituted iminomethyl,
$R^2$ is hydroxy, alkoxy or protected hydroxy,
$R^3$ is hydrogen and $R^4$ is methyl, hydroxymethyl or protected hydroxymethyl, or
$R^3$ and $R^4$ are combined together to form methylene or oxo,
$R^5$ is hydroxy, alkoxy or protected hydroxy, and
$R^6$ is hydrogen, imino-protective group or alkyl.

Among the object compounds (I), certain specific compound, in which $R^1$ is formyl, $R^2$ and $R^5$ are each hydroxy, $R^3$ and $R^6$ are each hydrogen and $R^4$ is carbamoyloxymethyl, was found to be produced by fermentation and is entitled to the FR-900482 substance.

With respect to the tetracyclo compounds (I) of this invention, it is to be understood that there may be one or more stereoisomeric pairs such as optical and geometrical isomers due to asymmetric carbon atoms and double bond, and such isomers are also included within a scope of this invention.

Suitable salts of the object compounds (I) are conventional pharmaceutically acceptable salts and may include a salt with a base such as an inorganic base salt, for example, an alkali metal salt (e.g. sodium salt, potassium salt, etc.), an alkaline earth metal salt (e.g. calcium salt, magnesium salt, etc.), an ammonium salt, an organic base salt, for example, an organic amine salt (e.g. triethylamine salt, pyridine salt, picoline salt, ethanolamine salt, triethanolamine salt, dicyclohexylamine salt, N,N'-dibenzylethylenediamine salt, etc.); a salt with an acid such as an inorganic acid addition salt (e.g. hydrochloride, hydrobromide, sulfate, phosphate, etc.), an organic acid addition salt (e.g. formate, acetate, trifluoroacetate, maleate, tartrate, methanesulfonate, benzenesulfonate, toluenesulfonate, etc.); a salt with a basic or acidic amino acid (e.g. arginine, aspartic acid, glutamic acid, etc.); and the like.

According to this invention, the object tetracyclo compounds (I) can be prepared by the processes as illustrated in the following schemes.

[I] Fermentation Process:

Species belonging to the genus Streptomyces —Fermentation→

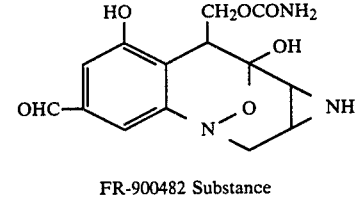

FR-900482 Substance

[II] Synthetic Process:

(1) Process 1 (Introduction of Imino-Protective Group)

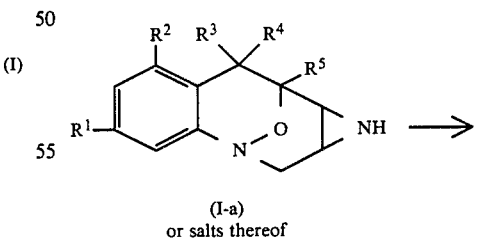

(I-a)
or salts thereof

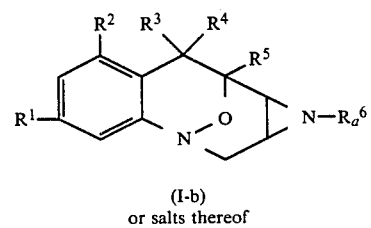

(I-b)
or salts thereof (2) Process 2 (Introduction of Hydroxy-Protective Group into 6-Hydroxy Group)

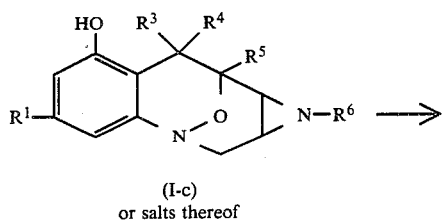

(I-c) or salts thereof

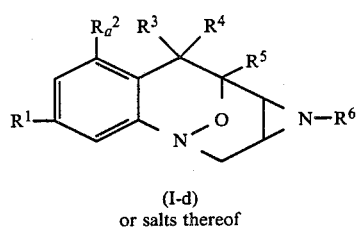

(I-d) or salts thereof (3) Process 3 (Introduction of Hydroxy-Protective Group into 9-Hydroxy Group)

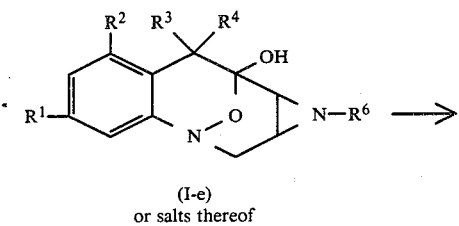

(I-e) or salts thereof

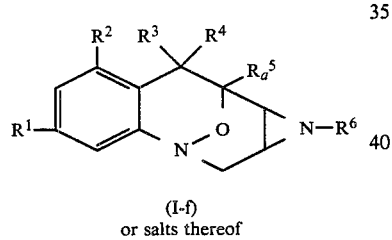

(I-f) or salts thereof (4) Process 4 (Introduction of Hydroxy-Protective Group into 8-Hydroxymethyl Group)

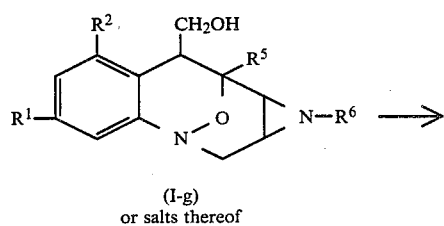

(I-g) or salts thereof

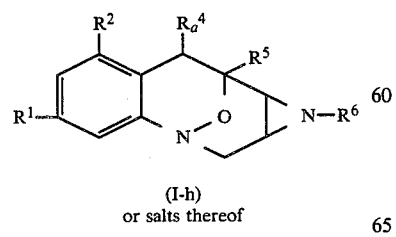

(I-h) or salts thereof (5) Process 5 (Introduction of Hydroxy-Protective Group into 4-Hydroxymethyl Group)

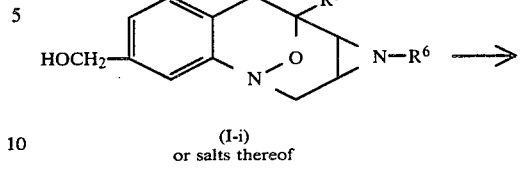

(I-i) or salts thereof

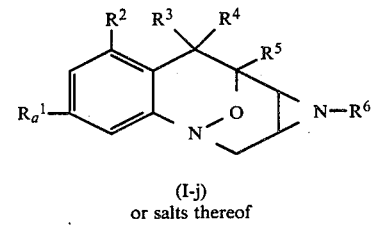

(I-j) or salts thereof (6) Process 6 (Reaction with Base)

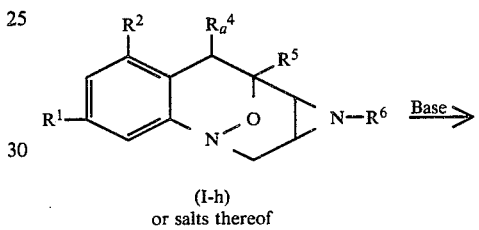

(I-h) or salts thereof

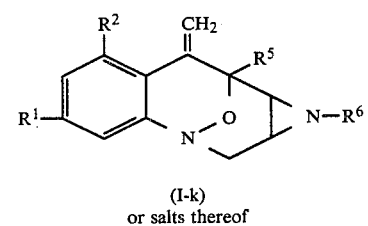

(I-k) or salts thereof (7) Process 7 (Reduction of Methylene Group)

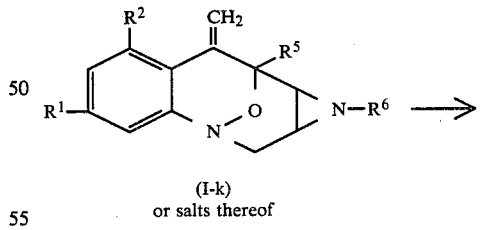

(I-k) or salts thereof

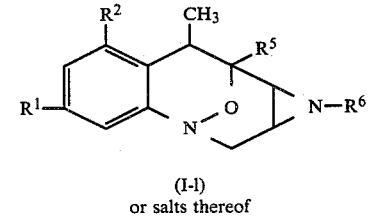

(I-l) or salts thereof (8) Process 8 (Reduction to Hydroxymethyl Group)

-continued (I-m) or salts thereof (I-i) or salts thereof (9) Process 9 (Introduction of Formyl-Protective Group)

(I-n) or salts thereof

(10) Process 10 (Alkylation of 6-Hydroxy Group)

(I-c) or salts thereof (I-p) or salts thereof

(11) Process 11 (Alkylation of 9-Hydroxy Group)

-continued (I-e) or salts thereof (I-q) or salts thereof

(12) Process 12 (Reaction with Substituted Amine)

(I-m) or salts thereof (I-r) or salts thereof

(13) Process 13 (Reduction of Arylimino Group)

(I-s) or salts thereof (I-t) or salts thereof

(14) Process 14 (Hydrolysis of Protected Hydroxymethyl Group)

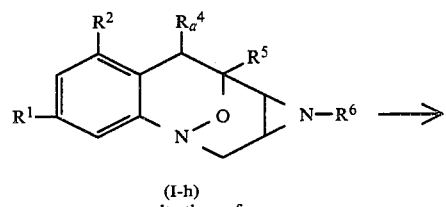

(I-h)
or salts thereof

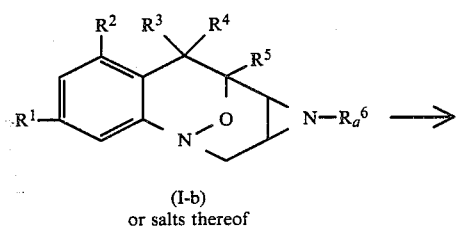

(I-g)
or salts thereof

(15) Process 15 (Removal of Imino-Protective Group)

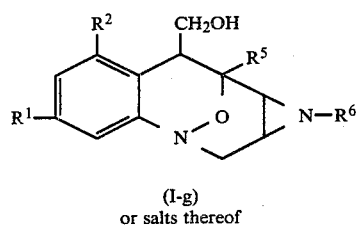

(I-b)
or salts thereof

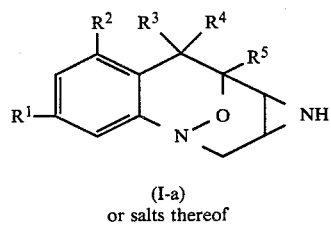

(I-a)
or salts thereof

(16) Process 16 (Oxidation of Formyl Group)

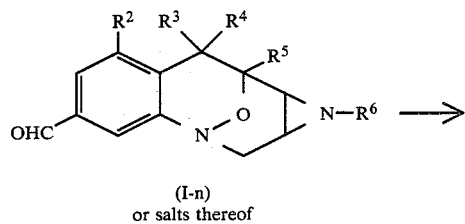

(I-n)
or salts thereof

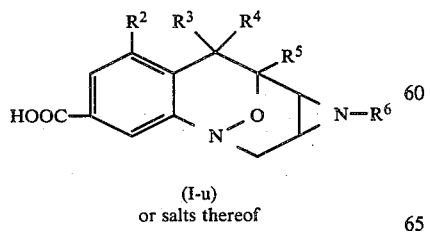

(I-u)
or salts thereof

(17) Process 17 (Oxidation of Methylene Group)

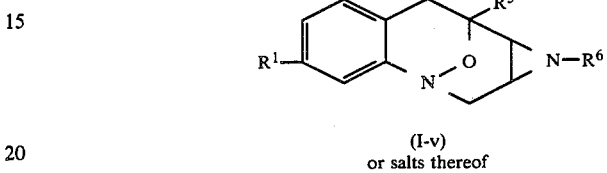

(I-k)
or salts thereof

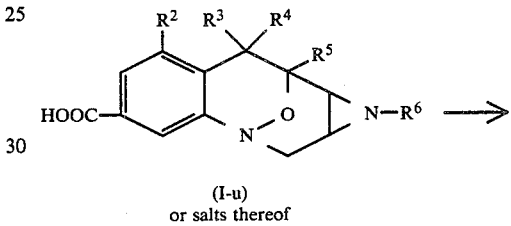

(I-v)
or salts thereof

(18) Process 18 (Introduction of Carboxy-Protective Group)

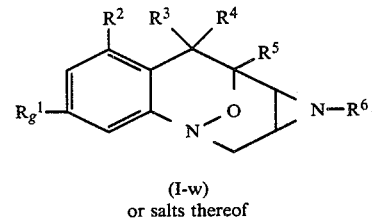

(I-u)
or salts thereof

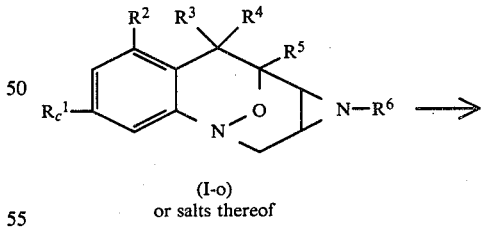

(I-w)
or salts thereof

(19) Process 19 (Removal of Formyl-Protective Group)

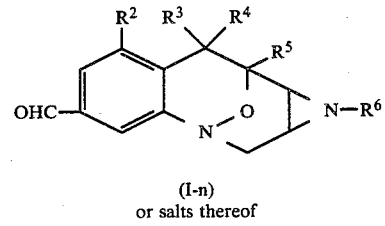

(I-o)
or salts thereof

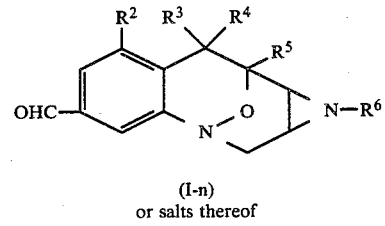

(I-n)
or salts thereof

(20) Process 20 (Alkylation of Imino Group)

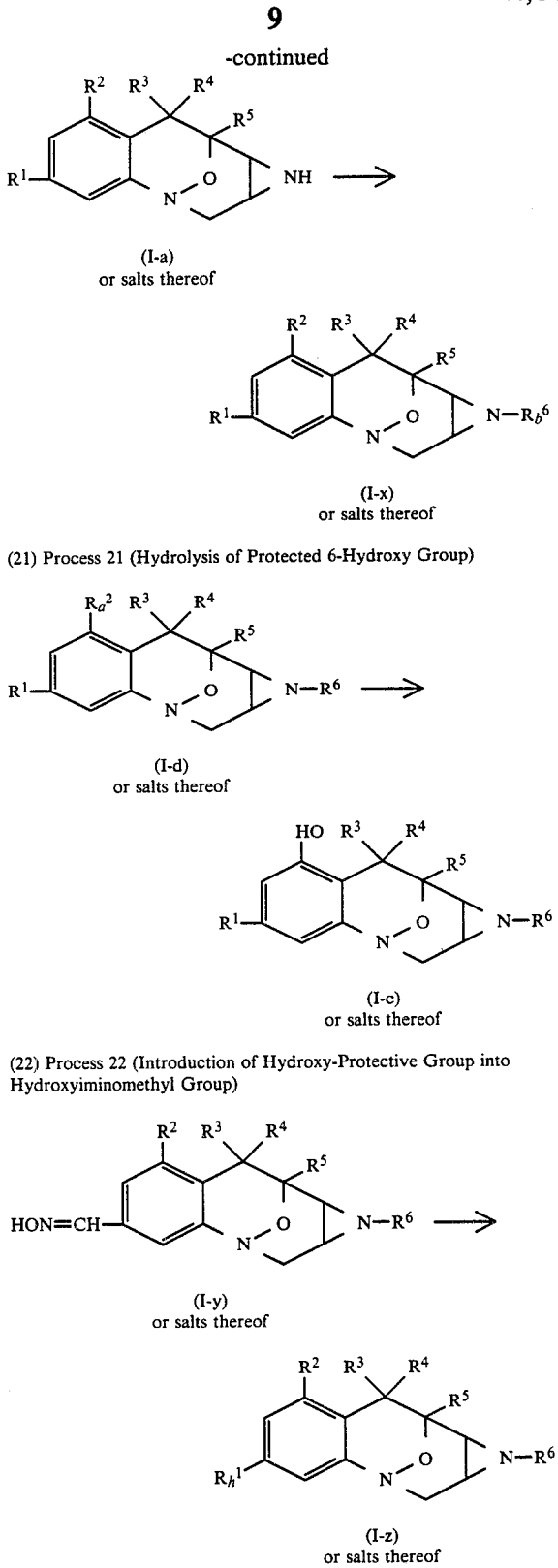

(I-a) or salts thereof (I-x) or salts thereof

(21) Process 21 (Hydrolysis of Protected 6-Hydroxy Group)

(I-d) or salts thereof (I-c) or salts thereof

(22) Process 22 (Introduction of Hydroxy-Protective Group into Hydroxyiminomethyl Group)

(I-y) or salts thereof (I-z) or salts thereof in which
$R^1$, $R^2$, $R^3$, $R^4$, $R^5$ and $R^6$ are each as defined above,
$R_a{}^1$ and $R_a{}^4$ are each protected hydroxymethyl,
$R_b{}^1$ is formyl or protected formyl,
$R_c{}^1$ is protected formyl,
$R_d{}^1$ is substituted iminomethyl,
$R_e{}^1$ is aryliminomethyl,
$R_f{}^1$ is arylaminomethyl,
$R_g{}^1$ is protected carboxy,
$R_h{}^1$ is protected hydroxyiminomethyl,
$R_a{}^2$ and $R_a{}^5$ are each protected hydroxy,
$R_b{}^2$ and $R_b{}^5$ are each alkoxy,
$R_a{}^6$ is imino-protective group, and
$R_b{}^6$ is alkyl.

Particulars of the above definitions and the preferred embodiments thereof are explained in detail as follows.

The term "lower" used in the specification is intended to mean 1 to 6 carbon atoms and the term "higher" is intended to mean 7 to 20 carbon atoms, unless otherwise indicated.

Suitable "imino-protective group" and the hydroxy-protective groups in "protected hydroxy" and "protected hydroxymethyl" and "protected hydroxyiminomethyl" may include acyl such as carbamoyl, aliphatic acyl, aromatic acyl, heterocyclic acyl and aliphatic acyl substituted with aromatic or heterocyclic group(s) derived from caboxylic, carbonic, sulfonic and carbamic acids.

The aliphatic acyl may include saturated or unsaturated, acyclic or cyclic ones, for example, alkanoyl such as lower or higher alkanoyl (e.g. formyl, acetyl, propionyl, butyryl, isobutyryl, valeryl, isovaleryl, pivaloyl, hexanoyl, heptanoyl, octanoyl, lauroyl, myristoyl, palmitoyl, stearoyl, etc.), alkylsulfonyl such as lower alkylsulfonyl (e.g. mesyl, ethylsulfonyl, propylsulfonyl, isopropylsulfonyl, butylsulfonyl, isobutylsulfonyl, pentylsulfonyl, hexylsulfonyl, etc.), N-alkylcarbamoyl (e.g. methylcarbamoyl, ethylcarbamoyl, etc.), alkoxycarbonyl such as lower alkoxycarbonyl (e.g. methoxycarbonyl, ethoxycarbonyl, propoxycarbonyl, butoxycarbonyl, tert-butoxycarbonyl, etc.), alkenoyl such as lower alkenoyl (e.g. acryloyl, methacryloyl, crotonoyl, etc.), cycloalkanecarbonyl such as cyclo(lower)alkanecarbonyl (e.g. cyclopropanecarbonyl, cyclopentanecarbonyl, cyclohexanecarbonyl, etc.), and the like.

The aromatic acyl may include aroyl (e.g. benzoyl, toluoyl, xyloyl, etc.), N-arylcarbamoyl (e.g. N-phenylcarbamoyl, N-tolylcarbamoyl, N-naphthylcarbamoyl, etc.), arenesulfonyl (e.g. benzenesulfonyl, tosyl, etc.), and the like.

The heterocyclic acyl may include heterocycliccarbonyl (e.g. furoyl, thenoyl, nicotinoyl, isonicotinoyl, thiazolylcarbonyl, thiadiazolylcarbonyl, tetrazolylcarbonyl, etc.), and the like.

The aliphatic acyl substituted with aromatic group(s) may include aralkanoyl such as phenyl(lower)alkanoyl (e.g. phenylacetyl, phenylpropionyl, phenylhexanoyl, etc.), aralkoxycarbonyl such as phenyl(lower)alkoxycarbonyl (e.g. benzyloxycarbonyl, phenethyloxycarbonyl, etc.), aryloxyalkanoyl such as phenoxy(lower)alkanoyl (e.g. phenoxyacetyl, phenoxypropionyl, etc.), and the like.

The aliphatic acyl substituted with heterocyclic group(s) may include heterocyclic-alkanoyl such as heterocyclic-(lower)alkanoyl (e.g. thienylacetyl, imidazolylacetyl, furylacetyl, tetrazolylacetyl, thiazolylacetyl, thiadiazolylacetyl, thienylpropionyl, thiadiazolylpropionyl, etc.), and the like.

These acyl groups may be further substituted with one or more suitable substituents such as lower alkyl (e.g. methyl, ethyl, propyl, isopropyl, butyl, pentyl, hexyl, etc.), halogen (e.g. chlorine, bromine, iodine, fluorine), lower alkoxy (e.g. methoxy, ethoxy, propoxy, isopropoxy, butoxy, pentyloxy, hexyloxy, etc.), lower alkylthio (e.g. methylthio, ethylthio, propylthio, isopropylthio, butylthio, pentylthio, hexylthio, etc.), nitro and the like, and preferable acyl having such substituent(s) may be mono (or di or tri)haloalkanoyl (e.g. chloroacetyl, bromoacetyl, dichloroacetyl, trifluoroacetyl, etc.), mono (or di or tri)haloalkoxycarbonyl (e.g. chloromethoxycarbonyl, dichloromethoxycarbonyl, 2,2,2-trichloroethoxycarbonyl, etc.), nitro (or halo or lower alkoxy)aralkoxycarbonyl (e.g. nitrobenzyloxycarbonyl, chlorobenzyloxycarbonyl, methoxybenzyloxycarbonyl, etc.), and the like.

More preferred example of the imino-protective group and the hydroxy-protective groups thus defined may be carbamoyl, lower alkanoyl, higher alkanoyl, aroyl which may have halogen, lower alkylsulfonyl, phenyl(lower)alkoxycarbonyl and N-arylcarbamoyl, and the most preferred one may be carbamoyl, acetyl, propionyl, octanoyl, p-bromobenzoyl, mesyl, benzyloxycarbonyl and N-phenylcarbamoyl.

Suitable "alkoxy" may include straight or branched one such as lower alkoxy (e.g. methoxy, ethoxy, propoxy, isopropoxy, butoxy, isobutoxy, pentyloxy, isopentyloxy, hexyloxy, etc.), and the like, in which more preferred example may be $C_1$-$C_4$ alkoxy and the most preferred one may be methoxy.

Suitable "protected formyl" may include acyclic or cyclic acetal of the formyl group, for example, dialkoxymethyl such as di(lower)alkoxymethyl (e.g. dimethoxymethyl, diethoxymethyl, dipropoxymethyl, diisopropoxymethyl, dibutoxymethyl, dipentyloxymethyl, dihexyloxymethyl, etc.), alkylenedioxymethyl such as lower alkylenedioxymethyl (e.g. 1,3-dioxolan-2-yl, 4-methyl-1,3-dioxolan-2-yl, 1,3-dioxan-2-yl, etc.), and the like, in which more preferred example may be di(lower)alkoxymethyl and the most preferred one may be dimethoxymethyl and diethoxymethyl.

Suitable "protected carboxy" may include esterified carboxy such as lower alkoxycarbonyl (e.g. methoxycarbonyl, ethoxycarbonyl, propoxycarbonyl, isopropoxycarbonyl, butoxycarbonyl, tert-butoxycarbonyl, etc.), mono(or di or tri)phenyl(lower)alkoxycarbonyl which may have a nitro group (e.g. benzyloxycarbonyl, 4-nitrobenzyloxycarbonyl, phenethyloxycarbonyl, benzhydryloxycarbonyl, trityloxycarbonyl, etc.), and the like, in which more preferred example may be $C_1$-$C_4$ alkoxycarbonyl and the most preferred one may be methoxycarbonyl.

Suitable aryl moiety of "arylaminomethyl" group may include phenyl, tolyl, xylyl, cumenyl, mesityl, naphthyl, and the like, in which the preferred example may be phenyl.

Suitable "alkyl" may include straight or branched one such as lower alkyl (e.g. methyl, ethyl, propyl, isopropyl, butyl, isobutyl, pentyl, isopentyl, neopentyl, hexyl, etc.), and the like, in which more preferred example may be $C_1$-$C_4$ alkyl and the most preferred one may be methyl.

Suitable "substituted imino" moiety in the term "substituted iminomethyl" may include arylimino (e.g. phenylimino, tolylimino, xylylimino, cumenylimino, mesitylimino, naphthylimino, etc.), hydroxyimino, alkoxyimino such as lower alkoxyimino (e.g. methoxyimino, ethoxyimino, propoxyimino, isopropoxyimino, butoxyimino, hexyloxyimino, etc.), acyloxyimino such as lower alkanoyloxyimino (e.g. formyloxyimino, acetoxyimino, propionyloxyimino, butyryloxyimino, pentanoyloxyimino, hexanoyloxyimino, etc.), semicarbazono, arylsemicarbazono (e.g. 4-phenylsemicarbazono, 4-tolylsemicarbazono, 4-naphthylsemicarbazono, etc.), and the like, in which more preferred example may be phenylimino, hydroxyimino, $C_1$-$C_4$ alkoxyimino, $C_1$-$C_4$ alkanoyloxyimino, semicarbazono and phenylsemicarbazono, and the most preferred one may be phenylimino, hydroxyimino, methoxyimino, acetoxyimino, semicarbazono and 4-phenylsemicarbazono.

The processes for production of the tetracyclo compound (I) of this invention are explained in detail in the following.

[I] Fermentation Process

The FR-900482 substance of this invention can be produced by fermentation of a FR-900482 substance-producing strain belonging to the genus Streptomyces such as *Streptomyces sandaensis* No. 6897 in a nutrient medium.

Particulars of microorganism used for the production of the FR-900482 substance will be explained in the following.

THE MICROORGANISM

The microorganism which can be used for the production of the FR-900482 substance is a FR-900482 substance-producing strain belonging to the genus Streptomyces, among which *Streptomyces sandaensis* No. 6897 has been newly isolated from a soil sample collected from Sanda City, Hyogo Prefecture, Japan.

A lyophilized sample of the newly isolated *Streptomyces sandaensis* No. 6897 has been deposited with the Fermentation Research Institute, Agency of Industrial Science and Technology (1–3, Higashi 1 chome Yatabe-machi, Tsukuba-gun, Ibaraki-ken, 305, Japan) under deposit number of FERM-P 7654 on June 1st, 1984, and then converted to Budapest Treaty route of the same depository on May 18, 1985 under the new deposit number of FERM BP-792.

It is to be understood that the production of the novel FR-900482 substance is not limited to the use of the particular organism described herein, which is given for the illustrative purpose only. This invention also includes the use of any mutants which are capable of producing the FR-900482 substance including natural mutants as well as artificial mutants which can be produced from the described organism by conventional means such as irradiation of X-rays, ultra-violet radiation, treatment with N-methyl-N'-nitro-N-nitrosoguanidine, 2-aminopurine, and the like.

The *Streptomyces sandaensis* No. 6897 has the following morphological, cultural, biological and physiological characteristics.

[1] Morphological Characteristics

The methods described by Shirling and Gottlieb (Shirling, E. B. and D. Gottlieb: Methods for characterization of Streptomyces species. International Journal of Systematic Bacteriology, 16, 313–340, 1966) were employed principally for this taxonomic study.

Morphological observations were made with light and electron microscopes on cultures grown at 30° C. for 14 days on yeast-malt extract agar, oatmeal agar or inorganic salts-starch agar. The mature sporophores formed Rectiflexibiles and Retinaculiaperti with 10 to 20 spores in each chain. The spores were cylindrical, 0.5–0.7×0.6–0.8 μm in size by electron microscopic observation. Spore surfaces were smooth.

[2] Cultural Characteristics

Cultural characteristics were observed on ten kinds of media described by Shirling and Gottlieb as mentioned above, and by Waksman (Waksman, S. A.: The actinomycetes, vol. 2: Classification, identification and description of genera and species. The Williams and Wilkins Co., Baltimore, 1961).

The incubation was made at 30° C. for 14 days. The color names used in this study were based on Color Standard (published by Nihon Shikisai Co., Ltd.). Colonies belonged to the gray color series when grown on oatmeal agar, yeast-malt extract agar and inorganic salts-starch agar. Soluble pigment was produced in yeast-malt extract agar but not in other media. The results are shown in Table 1.

acid. Accordingly, the cell wall of this strain is believed to be of type I.

[3] Biological and Physiological Properties

Physiological properties of the strain No. 6897 were determined according to the methods described in Shirling and Gottlieb as mentioned above. The results are shown in Table 2. Temperature range and optimum temperature for growth were determined on yeast-malt extract agar using a temperature gradient incubator (made by Toyo Kagaku Sangyo Co., Ltd.). Temperature range for growth was from 10° to 35° C. with optimum temperature from 30° to 32° C. Starch hydrolysis was positive. Melanoid pigment production was negative.

TABLE 1

Cultural characteristics of strain No. 6897, *Streptomyces aburaviensis* IFO 12830, *Streptomyces nitrosporeus* IFO 12803

| Medium | | No. 6897 | IFO 12830 | IFO 12803 |
|---|---|---|---|---|
| Oatmeal agar | G | Poor | Moderate | Poor |
| | A | Grayish yellow brown | Pale reddish brown | Grayish white, poor |
| | R | Pale yellow | Colorless | Colorless |
| | S | None | None | None |
| Yeast-malt extract agar | G | Moderate | Abundant | Moderate |
| | A | Light gray | Grayish yellow brown | Grayish yellow brown |
| | R | Dark yellow orange | Yellowish brown | Brown |
| | S | Pale brown | Pale brown | Brown |
| Inorganic salts strach agar | G | Moderate | Moderate | Moderate |
| | A | Grayish yellow brown | Grayish yellow brown | Olive gray |
| | R | Pale yelow orange | Pale reddish brown | Pale yellow orange |
| | S | None | None | None |
| Glucose-asparagine agar | G | Poor | Moderate | Moderate |
| | A | Pale yellow orange | Gray | Light gray |
| | R | Pale yellow orange | Dark gray | Pale yellowish brown |
| | S | None | None | Pale yellow |
| Glycerin-asparagine agar | G | Abundant | Moderate | Moderate |
| | A | Grayish yellow brown | Light gray | White |
| | R | Dark yellowish bown | Yellow orange | Pale yellow orange |
| | S | None | Pale brown | None |
| Sucrose-nitrate agar | G | Poor | Poor | Poor |
| | A | Light gray | None | Grayish white |
| | R | Colorless | Colorless | Colorless |
| | S | None | None | None |
| Nutrient agar | G | Moderate | Poor | Poor |
| | A | Grayish white | Light gray | Grayish white |
| | R | Pale yellow | Pale yellow | Colorless |
| | S | None | None | None |
| Potato-dextrose agar | G | Moderate | Moderate | Moderate |
| | A | Olive gray | Pale reddish brown | Olive gray |
| | R | Pale yellow orange | Pale yellow orange | Pale yellow orange |
| | S | None | None | None |
| Tyrosine agar | G | Abundant | Abundant | Moderate |
| | A | Grayishish yellow brown | Grayish yellow brown | Gray |
| | R | Pale yellowish brown to dark brown | Yellowish brown | Grayish yellow brown |
| | S | None | None | None |
| Peptone-yeat extract-iron agar | G | Poor | Poor | Moderate |
| | A | None | None | None |
| | R | Colorless | Colorless | Colorless |
| | S | None | None | Pale brown |

Abreviation: G = Growth, A = Aeial mass color, R = Reverse side color, S = Soluble pigment The cell wall analysis was performed by the method of Becker et al. (Becker, B., M. P. Lechevalier, R. E. Gordon and H. A. Lechevalier: Rapid differentiation between Nocardia and Streptomyces by paper chromatography of whole-cell hydrolysates: Appl. Microbiol., 12, 421–423, 1964) and Yamaguchi (Yamaguchi, T.: Comparison of the cell-wall composition of morphologically distinct actinomycetes: J. Bacteriol., 89, 444–453, 1965). Analysis of whole cell hydrolysates of the strain No. 6897 showed the presence of LL-diaminopimelic

TABLE 2

Physiological properties of strain No. 6897, *Streptomyces aburaviensis* IFO 12830 and *Streptomyces nitrosporeus* IFO 12803.

| Physiological Properties | Microorganisms | | |
|---|---|---|---|
| | No. 6897 | IFO 12803 | IFO 12803 |
| Temperature range for growth | 10° C.–35° C. | 17° C.–38 ° C. | 14° C.–37° C. |
| Optimum temperature | 30° C.–32° C. | 32° C. | 31° C. |
| Nitrate reduction | Negative | Negative | Positive |
| Starch hydrolysis | Positive | Positive | Positive |
| Milk coagulation | Negative | Negative | Negative |

TABLE 2-continued

Physiological properties of strain No. 6897, *Streptomyces aburaviensis* IFO 12830 and *Streptomyces nitrosporeus* IFO 12803.

| Physiological Properties | Microorganisms | | |
|---|---|---|---|
| | No. 6897 | IFO 12803 | IFO 12803 |
| Milk peptonization | Positive | Positive | Positive |
| Melanin production | Negative | Negative | Negative |
| Gelatin liquefaction | Positive | Negative | Positive |
| $H_2S$ production | Negative | Negative | Negative |
| Urease activity | Negative | Negative | Positive |
| NaCl tolerance (%) | 5% <, < 7% | 3% <, < 5% | 7% <, < 10% |

Utilization of carbon sources was examined according to the methods of Pridham and Gottlieb (Pridham, T. G. and D. Gottlieb: The utilization of carbon compounds by some Actinomycetales as an aid for species determination: J. Bacteriol., 56, 107–114, 1948). The growth was observed after 14 days incubation at 30° C.

Summarized carbon sources utilization of this strain is shown in Table 3. Sucrose and D-fructose could not be utilized by the strain No. 6897.

TABLE 3

Carbon utilizations of strain No. 6897, *Streptomyces aburaviensis* IFO 12830 and *Streptomyces nitrosporeus* IFO 12803

| Carbon Sources | Microorganisms | | |
|---|---|---|---|
| | No. 6897 | IFO 12830 | IFO 12803 |
| D-Glucose | + | + | + |
| Sucrose | − | − | − |
| Glycerin | + | + | + |
| D-Xylose | + | − | + |
| D-Fructose | − | − | − |
| Lactose | − | − | + |
| Maltose | + | + | + |
| Rhamnose | + | − | + |
| Raffinose | + | − | − |
| D-Galactose | + | − | + |
| L-Arabinose | + | − | + |
| D-Mannose | + | − | + |
| D-Trehalose | ± | ± | + |
| Inositol | − | − | − |
| Mannitol | − | − | − |
| Inulin | − | − | − |
| Cellulose | − | − | − |
| Salicin | + | − | + |
| Chitin | − | − | − |
| Sodium citrate | − | − | + |
| Sodium acetate | − | + | − |

Symbols:
+ = utilization, ± = doubtful utilization, − = no utilization

Microscopic studies and cell wall composition analysis of the strain No. 6897 indicate that this strain belongs to the genus Streptomyces Waksman and Henrici 1943.

Accordingly, a comparison of this strain was made with various Streptomyces species in the Light of the published descriptions [International Journal of Systematic Bacteriology, 18, 69 to 189, 279 to 392 (1968) and 19, 391 to 512 (1969), and Bergy's Manual of Determinative Bacteriology 8th Edition (1974)].

As a result of the comparison, the strain No. 6897 is considered to resemble *Streptomyces aburaviensis* Nishimura et. al. and *Streptomyces nitrosporeus* Okami. Therefore, the strain No. 6897 was further compared with the corresponding *Streptomyces aburaviensis* IFO 12830 and *Streptomyces nitrosporeus* IFO 12803 as shown in the above Tables 1, 2 and 3. From further comparison, the strain No. 6897 could be differentiated from these two strains in the following points, and therefore the strain No. 6897 is considered to be a novel species of Streptomyces and has been designated as *Streptomyces sandaensis* sp. nov., referring to the soil collected at Sanda City, from which the organism was isolated.

1 Difference from *Streptomyces aburaviensis* IFO 12830

Cultural characteristics of the strain No. 6897 are different from the *Streptomyces aburaviensis* on glucose-asparagine agar, sucrose-nitrate agar and potato-dextrose agar.

Gelatin liquefaction of the strain No. 6897 is positive, but that of the *Streptomyces aburaviensis* is negative.

In NaCl tolerance, the strain No. 6897 can grow in the presence of 5% NaCl, but the *Streptomyces aburaviensis* can not grow under the same condition.

In carbon sources utilization, the strain No. 6897 can utilize D-xylose, rhamnose, raffinose, D-galactose, L-arabinose, D-mannose and salicin, but the *Streptomyces aburaviensis* can not utilize them. And, the strain No. 6897 can not utilize sodium acetate, but the *Streptomyces aburaviensis* can utilize it.

2 Difference from *Streptomyces nitrosporeus* IFO 12803

Cultural characteristics of the strain No. 6897 are different from *Streptomyces nitrosporeus* on glucose-asparagine agar, glycerin-asparagine agar and tyrosine agar.

Nitrate reduction and urease activities of the strain No. 6897 are negative, but those of the *Streptomyces nitrosporeus* are positive.

In NaCl tolerance, the strain No. 6897 can not grow in the presence of 7% NaCl, but the *Streptomyces nitrosporeus* can grow under the same condition.

In carbon utilization, the strain No. 6897 can not utilize lactose and sodium citrate, but the *Streptomyces nitrosporeus* can utilize them. And the strain No. 6897 can utilize raffinose, but the *Streptomyces nitrosporeus* can not utilize it.

PRODUCTION OF FR-900482 SUBSTANCE

The novel FR-900482 substance of this invention can be produced by culturing a FR-900482 substance-producing strain belonging to the genus Streptomyces (e.g. *Streptomyces sandaensis* No. 6897, FERM P-7654) in a nutrient medium.

In general, the FR-900482 substance can be produced by culturing the FR-900482 substance-producing strain in an aqueous nutrient medium containing sources of assimilable carbon and nitrogen, preferably under aerobic conditions (e.g. shaking culture, submerged culture, etc.).

The preferred sources of carbon in the nutrient medium are carbohydrates such as glucose, xylose, galactose, glycerin, starch, dextrin, and the like. Other sources which may be included are maltose, rhamnose, raffinose, arabinose, mannose, salicin, sodium succinate, and the like.

The preferred sources of nitrogen are yeast extract, peptone, gluten meal, cottonseed meal, soybeam meal, corn steep liquor, dried yeast, wheat germ, feather meal, peanut powder etc., as well as inorganic and organic nitrogen compounds such as ammonium salts (e.g. ammonium nitrate, ammonium sulfate, ammonium phosphate, etc.), urea, amino acid and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salt and the like. If necessary, especially when the culture medium foams seriously, a defoaming agent, such as liquid paraffin, fatty oil, plant oil, mineral oil or silicone may be added.

As the conditions for the production of the FR-900482 substance in massive amounts, submerged aerobic cultural conditions are preferred therefor. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of the FR-900482 substance. Accordingly, it is desirable first to produce a vegetative inoculum of the organism by inoculating a relatively small quantity of culture medium with spores or mycelia of the organism and culturing said inoculated medium, and then to transfer the cultured vegetative inoculum aseptically to large tanks. The medium, in which the vegetative inoculum is produced, is substantially the same as or different from the medium utilized for the production of the FR-900482 substance.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 20° C. and 40° C., preferably 25°-35° C., for a period of about 50 hours to 150 hours, which may be varied according to fermentation conditions and scales.

Thus produced FR-900482 substance can be recovered from the culture medium by conventional means which are commonly used for the recovery of other known biologically active substances. In general, most of the FR-900482 substance produced are found in the cultured filtrate, and accordingly the the FR-900482 substance can be isolated and purified from the filtrate, which is obtained by filtering or centrifuging the cultured broth, by a conventional method such as concentration under reduced pressure, lyophilization, extraction with a conventional solvent, pH adjustment, treatment with a conventional resin (e.g. anion or cation exchange resin, non-ionic adsorption resin, etc.), treatment with a conventional adsorbent (e.g. activated charcoal, silicic acid, silica gel, cellulose, alumina, etc.), crystallization, recrystallization, and the like.

The FR-900482 substance produced according to the aforementioned process possesses the following physical and chemical properties, and the measurement of the silica gel thin layer chromatography indicates two kinds of Rf values.

(1) Form and Color: colorless powder
(2) Elemental Analysis: C: 49.73%, H: 4.83%, N: 12.52%, S: 0.00%
(3) Color Reaction:
  Positive: sulfuric acid reaction, potassium permanganate reaction, ninhydrin reaction, 2,4-dinitrophenylhydrazine reaction, iodine vapor reaction and ferric chloride-potassium ferricyanide reaction
  Negative: ferric chloride reaction and Sakaguchi reaction
(4) Solubility:
  Soluble: water and methanol
  Insoluble: acetone, ethyl acetate and chloroform
(5) Melting Point:
  around 175° C.: starting coloring to pale yellow,
  around 210° C.: turning to brown and charamelizing,
  around 300° C.: no melting
(6) Specific Rotation:
  $[\alpha]_D^{23}$: +8° (c=1.0, $H_2O$)
  $[\alpha]_D^{23}$: −26.5° (c=1.0, 0.1N HCl)
(7) Ultraviolet Absorption Spectra:

| | |
|---|---|
| $\lambda_{max}^{methanol}$: | 218 nm ($E_{1cm}^{1\%}$ = 630) |
| | 236 nm ($E_{1cm}^{1\%}$ = 600) |
| | 281 nm ($E_{1cm}^{1\%}$ = 190) |
| | 330 nm ($E_{1cm}^{1\%}$ = 70) |
| $\lambda_{max}^{methanol+HCl}$: | 216, ca.240(sh), 282, 331 nm |
| $\lambda_{max}^{methanol+NaOH}$: | 238, 302, 374 nm |

(8) Infrared Absorption Spectrum: $\nu_{max}^{KBr}$: 3600−3000, 1690, 1580, 1400, 1340, 1080 $cm^{-1}$
(9) Molecular Weight: SI Mass: m/z (observed) 322
(10) $^{13}C$ Nuclear Magnetic Resonance Spectrum: δ(ppm, DCl+$D_2O$, pD=ca.1): 195.4 (d), 159.1 (s), 156.3 (s), 147.4 (s), 136.6 (s), 118.3 (s), 114.3 (d), 111.2 (d), 90.8 (s), 60.7 (t), 49.4 (t), 44.1 (d), 36.3 (d), 36.3 (d)
(11) $^1H$ Nuclear Magnetic Resonance spectrum: δ(ppm, DCl+$D_2O$, pD=ca.1): 9.67 (1H, s), 7.00 (2H, s), 5.21 (1H, dd, J=11 and 6 Hz), 4.6 (1H, d, J=11 Hz), 4.16 (1H, d, J=17 Hz), 4.04 (1H, dd, J=17 and 5 Hz), 3.74 (2H, m), 3.65 (1H, d, J=6 Hz)
(12) Thin Layer Chromatography:

| Stationary Phase | Developing Solvent | Rf Value |
|---|---|---|
| silica gel plate | isopropyl alcohol:water (9:1 v/v) | 0.55 and 0.65 |
| | chloroform:methanol (4:1, v/v) | 0.20 and 0.45 |
| | butanol:acetic acid:water (20:1:2, v/v) | 0.50 |
| cellulose plate | isopropyl alcohol:water (8:2, v/v/v) | 0.80 |

With regard to the FR-900482 substance, it is to be noted that this substance further possesses the following chemical characteristics.

(A) A single compound having the following physical and chemical properties (hereinafter entitled FR-900482A substance) can be obtained by treating the FR-900482 substance with hydrochloric acid.
(1) Form and Color: colorless powder
(2) Solubility:
  Soluble: water and methanol
  Insoluble: acetone, ethyl acetate and chloroform
(3) Melting Point:
  around 160° C.: coloring to pale yellow,
  around 200° C.: turning to brown,
  200° to about 300° C.: becoming dark (no melting)
(4) Specific Rotation: $[\alpha]_D^{23}$: −27° (c=1.0, 0.1N HCl)
(5) Ultraviolet Absorption Spectrum:

| | |
|---|---|
| $\lambda_{max}^{0.1N\ HCl}$: | 228 nm ($E_{1cm}^{1\%}$ = 545) |

| | |
|---|---|
| 273 nm ($E_{1cm}^{1\%}$ = 180) | |
| 327 nm ($E_{1cm}^{1\%}$ = 60) | |

(6) Infrared Absorption Spectrum: $\nu_{max}^{KBr}$: 3600–3000, 1690, 1580, 1340, 1270, 1130, 1080 cm$^{-1}$ Thus obtained single FR-900482A substance can be converted by neutralization with an aqueous sodium hydroxide into the starting FR-900482 substance which shows two kinds of the Rf values in the silica gel thin layer chromatography.

(B) A single triacetyl derivative of the FR-900482 substance having the following physical and chemical properties can be obtained by treating the FR-900482 substance with an excess of an acetic anhydride.

(1) Form and Color: colorless platelet
(2) Elementary Analysis: Found C: 53.85%, H: 4.91%, N: 9.19% Calculated for $C_{20}H_{21}O_9N_3$ C: 53.69%, H: 4.73%, N: 9.39%
(3) Color Reaction:
  Positive: cerium sulfate reaction, iodine vapor reaction and phosphomolybdic acid reaction
  Negative: Sakaguchi reaction
(4) Solubility:
  Soluble: chloroform, acetone and methanol
  Insoluble: water
(5) Melting Point: 170° to 173° C.
(6) Specific Rotation: $[\alpha]_D^{23}$: +66.6° (c=1.0, $CH_3OH$)
(7) Ultraviolet Absorption Spectra:

| | |
|---|---|
| $\lambda_{max}^{methanol}$: | 239 nm ($\epsilon$ = 15,400) |
| | 270(sh) nm ($\epsilon$ = 4,100) |
| | 322 nm ($\epsilon$ = 1,100) |
| $\lambda_{max}^{methanol+HCl}$: | 240, 280 nm |
| $\lambda_{max}^{methanol+NaOH}$: | 230, 250(sh), 300, 370 nm |

(8) Infrared Absorption Spectrum: $\nu_{max}^{chloroform}$: 3550, 3450, 3030, 2930, 2850, 1760(sh), 1735, 1700, 1580, 1440, 1400, 1375, 1340, 1200, 1170, 1140, 1110, 1095, 1080, 1040, 995 cm$^{-1}$ (9) Thin Layer Chromatography:

| Stationary Phase | Developing Solvent | Rf value |
|---|---|---|
| silica gel plate | chloroform:methanol (95:5, v/v) | 0.35 |

(10) Molecular Weight:
  EI Mass: m/z 447 (M+)
  High Mass:
    M+observed 447.1286
    M+calculated 447.1277 for $C_{20}H_{21}N_3O_9$
(11) $^{13}C$ Nuclear Magnetic Resonance Spectrum:
  δ(ppm, $CDCl_3$): 21.0 (q), 21.7 (q), 22.9 (q), 31.6 (d), 39.8 (d), 40.2 (d), 52.9 (t), 63.2 (t), 96.4 (s), 115.5 (d), 119.0 (d), 124.2 (s), 136.2 (s), 149.4 (s), 149.7 (s), 155.9 (s), 168.5 (s), 169.1 (s), 180.8 (s), 190.3 (d)
(12) $^1H$ Nuclear Magnetic Resonance Spectrum: δ(ppm, $CDCl_3$): 9.9 (1H, s), 7.31 (1H, d, J=1.3 Hz), 7.14 (1H, d, J=1.3 Hz), 4.72 (2H, broad), 4.4 (1H, dd, J=12 and 7 Hz), 4.35 (1H, dd, J=12 and 3.8 Hz), 4.06 (1H, dd, J=15 and 2 Hz), 3.89 (1H, dd, J=7 and 3.8 Hz), 3.74 (1H, d, J=15 Hz), 3.41 (1H, d, J=6.3 Hz), 2.84 (1H, dd, J=6.3 and 2 Hz), 2.40 (3H, s), 2.24 (3H, s), 1.98 (3H, s)

From the above physical and chemical properties and the analysis of the X ray diffraction, the triacetyl derivative of the FR-900482 substance could be determined to have the following chemical structure.

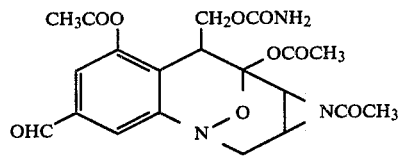

11-acetyl-8-carbamoyloxymethyl-4-formyl-14-oxa-1,11-diazatetracyclo[7.4.1.0$^{2,7}$,0$^{10,12}$]tetradeca-2,4,6-trien-6,9-diyl diacetate.

Thus obtained single triacetyl derivative of the FR-900482 substance can be converted by an aqueous sodium bicarbonate into the starting FR-900482 substance which shows two kinds of the Rf values in the silica gel thin layer chromatography.

(C) The FR-900482 substance can be proved to exist as a mixture of two components around neutral condition and further to exist as a single component around pH 1 condition by the nuclear magnetic resonance spectra as shown in the attached FIGS. 1 and 2 or the silica gel thin layer chromatography using a chromatoscanner.

(D) The isolated component showing 0.55 Rf value in the aforementioned silica gel thin layer chromatography was further subject to the silica gel thin layer chromatography, which indicates two kinds of the Rf values corresponding to those of the FR-900482 substance. Similarly, the other isolated component showing 0.65 Rf value was further subjected to the silica gel thin layer chromatography, which also indicates two kinds of the Rf values corresponding to those of the FR-900482 substance.

From the above chemical characteristics of the FR-900482 substance, the FR-900482 substance can be represented by the following plane structural formula and two kinds of the components which revealed in the measurement of the silica gel thin layer chromatography are considered to be a mutual equilibrium mixture having the same plane structure.

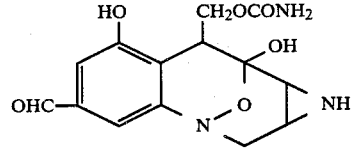

4-Formyl-6,9-dihydroxy-14-oxa-1,11-diazatetracyclo[7.4.1.0$^{2,7}$,0$^{10,12}$]tetradeca-2,4,6-trien-8-ylmethyl carbamate.

[II] Synthetic Process (1) Process 1 (Introduction of Imino-Protective Group)

The compound (I-b) or salts thereof can be prepared by introducing an imino-protective group into the compound (I-a) or salts thereof.

Suitable salts of the compounds (I-a) and (I-b) may be the same as those for the compounds (I).

Suitable introducing agent of the imino-protective group used in this reaction may be a conventional acylating agent which is capable of introducing the acyl group as mentioned before such as carboxylic acid, carbonic acid, sulfonic acid and their reactive derivative, for example, an acid halide, an acid anhydride, an activated amide, an activated ester, and the like. Preferable example of such reactive derivative may include acid chloride, acid bromide, a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkyl carbonate (e.g. methyl carbonate, ethyl carbonate, propyl carbonate, etc.), aliphatic carboxylic acid (e.g. pivalic acid, pentanoic acid, isopentanoic acid, 2-ethylbutyric acid, trichloroacetic acid, etc.), aromatic carboxylic acid (e.g. benzoic acid, etc.), a symmetrical acid anhydride, an activated acid amide with a heterocyclic compound containing imino function such as imidazole, 4-substituted imidazole, dimethylpyrazole, triazole and tetrazole, an activated ester (e.g. p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyridyl ester, piperidinyl ester, 8-quinolyl thioester, or an ester with a N-hydroxy compound such as N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.), and the like.

This reaction can be carried out in the presence of an organic or inorganic base such as alkali metal (e.g. lithium, sodium, potassium, etc.), alkaline earth metal (e.g. calcium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compound (e.g. pyridine, lutidine, picoline, 4-dimethylaminopyridine, etc.), quinoline, and the like.

In case that the introducing agent of the imino-protective group is used in a free form or its salt in this reaction, the reaction is preferably carried out in the presence of a condensing agent such as a carbodiimide compound [e.g. N,N'-dicyclohexylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.], a ketenimine compound (e.g. N,N'-carbonylbis(2-methylimidazole), pentamethyleneketene-N-cyclohexylimine, diphenylketene-N-cyclohexylimine, etc.); an olefinic or acetylenic ether compounds (e.g. ethoxyacetylene, β-chlorovinylethyl ether), a sulfonic acid ester of N-hydroxybenzotriazole derivative [e.g. 1-(4-chlorobenzenesulfonyloxy)-6-chloro-1H-benzotriazole, etc.], a combination of trialkylphosphite or triphenylphosphine and carbon tetrachloride, disulfide or diazenedicarboxylate (e.g. diethyl diazenedicarboxylate, etc.), a phosphorus compound (e.g. ethyl polyphosphate, isopropyl polyphosphate, phosphoryl chloride, phosphorus trichloride, etc.), thionyl chloride, oxalyl chloride, N-ethylbenzisoxazolium salt, N-ethyl-5-phenylisoxazolium-3-sulfonate, a reagent (referred to a so-called "Vilsmeier reagent") formed by the reaction of an amide compound such as N,N-di(lower)alkylformamide (e.g. dimethylformamide, etc.), N-methylformamide or the like with a halogen compound such as thionyl chloride, phosphoryl chloride, phosgene or the like.

The reaction is usually carried out in a conventional solvent which does not adversely influence the reaction such as water, acetone, dichloromethane, alcohol (e.g. methanol, ethanol, etc.), tetrahydrofuran, pyridine, N,N-dimethylformamide, etc., or a mixture thereof, and further in case that the imino-introducing agent is in liquid, it can also be used as a solvent.

The reaction temperature is not critical and the reaction is usually carried out under from cooling to heating.

This process includes, within a scope thereof, a case that during the reaction, at least one of the hydroxyiminomethyl or hydroxymethyl group for $R^1$ and hydroxymethyl group for $R^4$ and the hydroxy groups for $R^2$ and $R^5$ of the compound (I-a) may occasionally be transformed into the corresponding protected hydroxyiminomethyl and protected hydroxymethyl and protected hydroxy groups in the object compound (I-b).

(2) Process 2 (Introduction of Hydroxy-Protective Group into 6-Hydroxy Group)
(3) Process 3 (Introduction of Hydroxy-Protective Group into 9-Hydroxy Group)
(4) Process 4 (Introduction of Hydroxy-Protective Group into 8-Hydroxymethyl Group)
(5) Process 5 (Introduction of Hydroxy-Protective Group into 4-Hydroxymethyl Group)

The compounds (I-d), (I-f), (I-h) and (I-j) or salts thereof can be prepared by introducing a hydroxy-protective group into the compounds (I-c), (I-e), (I-g) and (I-i) or salts thereof, respectively.

Suitable salts of the compounds (I-c) to (I-j) are the same as those for the compounds (I).

Suitable introducing agent of the hydroxy-protective group used in the Processes 2 to 5 may be a conventional acylating agent which is capable of introducing the acyl group as mentioned before such as those given in the Process 1.

These reactions may be carried out by substantially the same method as the Process 1, and therefore the reaction method and reaction conditions (e.g. solvent, reaction temperature, etc.) are to be referred to the explanation for the Process 1.

During the reactions in these Processes 2 to 5, there may occur
  (i) a case that in the Processes 2 to 4, the hydroxyiminomethyl or hydroxymethyl groups for $R^1$ of the starting compounds (I-c), (I-e) and (I-g) may occasionally be transformed into the corresponding protected hydroxyiminomethyl or hydroxymethyl groups, respectively,
  (ii) a case that in the Processes 3 to 5, the hydroxy groups for $R^2$ of the starting compounds (I-e), (I-g) and (I-i) may occasionally be transformed into the corresponding protected hydroxy groups, respectively,
  (iii) a case that in the Processes 2, 3 and 5, the hydroxymethyl groups for $R^4$ of the starting compounds (I-c), (I-e) and (I-i) may occasionally be transformed into the corresponding protected hydroxymethyl groups, respectively, (iv) a case that in the Processes 2, 4 and 5, the hydroxy groups for $R^5$ of the starting compounds (I-c), (I-g) and (I-i) may occasionally be transformed into the corresponding protected hydroxy groups, respectively, and (v) a case that in the Processes 2 to 5, the free imino group of the starting compounds (I-c), (I-e), (I-g) and (I-i), which is formed by $R^6$ being hydrogen, may occasionally be transformed into their protected imino groups, respectively, and these cases are also included within scopes of the Processes 2 to 5.

(6) Process 6 (Reaction with Base)

The compound (I-k) or salts thereof can be prepared by reacting the compound (I-h) or salts thereof with base.

Suitable salts of the compounds (I-h) and (I-k) are the same as those for the compounds (I).

Suitable base used in this reaction may be a conventional one which is used in conversion of a protected hydroxymethyl group to a methylene group such as those given in Process 1.

This reaction is usually carried out in a conventional solvent which does not adversely influence the reaction such as water, alcohol (e.g. methanol, ethanol, etc.), pyridine, N,N-dimethylformamide, etc., or a mixture thereof, and further in case that the base to be used is in liquid, it can also be used as a solvent.

The reaction temperature is not critical and the reaction is usually carried out from at room temperature to under warming.

This process includes, within a scope thereof, a case that during the reaction the formyl group for $R^1$ may occasionally be transformed into the hydroxymethyl group.

(7) Process 7 (Reduction of Methylene Group)

The compound (I-l) or salts thereof can be prepared by reducing the compound (I-k) or salts thereof.

Suitable salts of the compound (I-l) are the same as those for the compounds (I).

Reduction in this process can be carried out by a conventional method which is capable of reducing a methylene group to a methyl group, such as catalytic reduction, or the like.

Suitable catalysts used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.), and the like.

The reduction is usually carried out in a conventional solvent which does not adversely influence the reaction such as water, methanol, ethanol, propanol, pyridine, N,N-dimethylformamide, dichloromethane, or a mixture thereof.

The reaction temperature of this reduction is not critical and the reaction is usually carried out under from cooling to warming.

(8) Process 8 (Reduction to Hydroxymethyl Group)

The compound (I-i) or salts thereof can be prepared by reducing the compound (I-m) or salts thereof.

Suitable salts of the compound (I-m) are the same as those for the compounds (I).

Reduction in this process can be carried out by a conventional method, which is capable of reducing a formyl or a protected formyl group to a hydroxymethyl group, such as catalytic reduction, reduction using reducing agent, and the like.

The catalytic reduction can be carried out by substantially the same method as the Process 7, and therefore the suitable catalysts and the reaction conditions of this reduction (e.g. solvent, reaction temperature, etc.) are to be referred to the explanation for the Process 7.

Suitable reducing agent may be alkali borohydride compounds (e.g. sodium borohydride, sodium cyanoborohydride, etc.), alkali amalgam (e.g. sodium amalgam, etc.), and the like.

The reduction using reducing agent is usually carried out in a conventional solvent which does not adversely influence the reaction such as those for the catalytic reduction in the Process 7.

The reaction temperature of this reduction is not critical and the reaction is usually carried out under from cooling to warming.

This reduction includes, within a scope thereof, a case that at least one of the hydroxy-protective groups in $R^2$, $R^4$ and $R^5$ and the imino-protective group in $R^6$ may occasionally be removed at the same time during the reaction.

Further, the reduction can also be carried out by using alkali metal hydroxide given in the Process 1, and in this case, the protected hydroxymethyl group for $R^4$ may occasionally be transformed into the methylene group.

(9) Process 9 (Introduction of Formyl-Protective Group)

The compound (I-o) or salts thereof can be prepared by introducing a formyl-protective group into the compound (I-n) or salts thereof.

Suitable salts of the compounds (I-n) and (I-o) are the same as those for the compounds (I).

Suitable introducing agent of the formyl-protective group used in this reaction may include alcohol such as alkanol (e.g. methanol, ethanol, propanol, isopropanol, butanol, pentyl alcohol, hexyl alcohol, etc.), alkanediol (e.g. ethylene glycol, propylene glycol, 1,3-propanediol, etc.), and the like.

This reaction is preferably carried out under anhydrous condition in the presence of an acid such as hydrogen halide (e.g. hydrogen chloride, hydrogen bromide, etc.).

Further, this reaction is usually carried out in a conventional solvent which does not adversely influence the reaction, and in many cases the alcohol enumerated as the introducing agent of the formyl-protective group can be used as such a solvent.

The reaction temperature of this reduction is not critical and the reaction is usually carried out under from cooling to warming.

(10) Process 10 (Alkylation of 6-Hydroxy Group)
(11) Process 11 (Alkylation of 9-Hydroxy Group)

The compounds (I-p) and (I-q) or salts thereof can be prepared by reacting the compounds (I-c) and (I-e) or salts thereof with an alkylating agent, respectively.

Suitable salts of the compounds (I-p) and (I-q) are the same as those for the compounds (I).

Suitable alkylating agent used in this reaction may include a conventional one which is capable of alkylating a hydroxy group to an alkoxy group such as dialkyl sulfate (e.g. dimethyl sulfate, diethyl sulfate, etc.), alkyl sulfonate (e.g. methyl sulfonate, etc.), alkyl halide (e.g. methyl iodide, ethyl iodide, propyl bromide, etc.), diazoalkanes (e.g. diazomethane, diazoethane, etc.), and the like.

This reaction is preferably carried out in the presence of an inorganic or organic base such as those given in the explanation of the Process 1.

Further, this reaction is usually carried out in a conventional solvent which does not adversely influence the reaction such as water, acetone, dichloromethane, methanol, ethanol, propanol, pyridine, N,N-dimethylformamide, or a mixture thereof.

The reaction temperature is not critical and the reaction is usually carried out under from cooling to warming.

The process 10 includes, within a scope thereof, a case that during the reaction, at least one of the hydroxy group for $R^5$ and the imino group formed by $R^6$ being hydrogen of the starting compound (I-c) may occasionally be transformed into the corresponding alkoxy group and the alkylamino group, respectively.

Further, the Process 11 includes, within a scope thereof, a case that during the reaction, at least one of the hydroxy group for $R^2$ and the imino group formed by $R^6$ being hydrogen of the starting compound (I-e) may occasionally be transformed into the corresponding alkoxy group and the alkylimino group, respectively.

(12) Process 12 (Reaction with Substituted Amine)

The compound (I-r) or salts thereof can be prepared by reacting the compound (I-m) or salts thereof with the substituted amine or salts thereof.

Suitable salts of the compound (I-r) may be the same as those for the compounds (I)

Suitable salts of the substituted amine may be the salts with an acid such as those for the compounds (I).

Suitable substituted amine used in this reaction may be arylamine (e.g. aniline, toluidine, xylidine, cumenylamine, mesitylamine, naphthyamine, etc.), hydroxylamine, O-alkylhydroxylamine (e.g. O-methylhydroxylamine, etc.), semicarbazide, arylsemicarbazide (e.g. 4-phenylsemicarbazide, etc.), and the like.

The reaction is usually carried out in a conventional solvent which does not adversely influence the reaction such as water, dichloromethane, methanol, ethanol, propanol, pyridine, N,N-dimethylformamide, or a mixture thereof.

In case that the substituted amine is used in a salt form, this reaction is preferably carried out in the presence of a base such as those given in the explanation of the Process 1.

The reaction temperature is not critical and the reaction is usually carried out under from cooling to warming.

(13) Process 13 (Reduction of Arylimino Group)

The compound (I-t) or salts thereof can be prepared by reducing the compound (I-s) or salts thereof.

Suitable salts of the compound (I-t) may be the same as those for the compounds (I).

Reduction in this process can be carried out by a conventional method which is capable of reducing an arylimino group to an arylamino group, such as catalytic reduction, or the like.

The catalytic reduction can be carried out by substantially the same method as the Process 7, and therefore the suitable catalysts and the reaction conditions of this reduction (e.g. solvent, reaction temperature, etc.) are to be referred to the explanation for the Process 7.

(14) Process 14 (Hydrolysis of Protected Hydroxymethyl Group)

The compound (I-g) or salts thereof can be prepared by hydrolysing the compound (I-h) or salts thereof.

The hydrolysis can be carried out in the presence of a base or an acid, and suitable base may be the inorganic base such as those given in the Process 1. Suitable acid may be an organic acid (e.g. formic acid, acetic acid, propionic acid, trifluoroacetic acid, benzenesulfonic acid, p-toluenesulfonic acid, etc.) and an inorganic acid (e.g. hydrochloric acid, hydrobromic acid, sulfuric acid, phosphoric acid, etc.).

This reaction is usually carried out in a conventional solvent which does not adversely influence the reaction such as water, acetone, dichloromethane, methanol, ethanol, propanol, pyridine, N,N-dimethylformamide, or a mixture thereof.

The reaction temperature is not critical and the reaction is usually carried out under from cooling to warming.

(15) Process 15 (Removal of Imino-Protective Group)

The compound (I-a) or salts thereof can be prepared by removing an imino-protective group from the compound (I-b) or salts thereof.

This removal reaction is carried out in a conventional method such as reduction, hydrolysis, and the like.

The reduction method applicable for this removal reaction may include catalytic reduction as explained in the Process 7, and therefore the reaction mode and the reaction conditions (e.g. reaction temperature, solvent, etc.) are to be referred to the explanation therefor.

Hydrolysis is preferably carried out in the presence of a base or an acid. Suitable base may include an alkali metal hydroxide (e.g. sodium hydroxide, potassium hydroxide, etc.), an alkaline earth metal hydroxide (e.g. magnesium hydroxide, calcium hydroxide, etc.), an alkali metal carbonate (e.g. sodium carbonate, potassium carbonate, etc.), an alkaline earth metal carbonate (e.g. magnesium carbonate, calcium carbonate, etc.), an alkali metal bicarbonate (e.g. sodium bicarbonate, potassium bicarbonate, etc.), and the like.

Suitable acid may include an organic acid (e.g. formic acid, acetic acid, propionic acid, trifluoroacetic acid, benzenesulfonic acid, p-toluenesulfonic acid, etc.) and an inorganic acid (e.g. hydrochloric acid, hydrobromic acid, sulfuric acid, phosphoric acid, etc.). The acidic hydrolysis using trifluoroacetic acid is usually accelerated by addition of cation trapping agent (e.g. phenol, anisole, etc.).

The solvent and the reaction temperature in this hydrolysis may be the same as those for the reduction as mentioned above.

The removal method can be selected according to the kinds of the imino-protective group to be removed.

This process includes, within a scope thereof, a case that the protected formyl group for $R^1$ of the starting compound (I-b) may occasionally be transformed into the formyl group in the object compound (I-a).

(16) Process 16 (Oxidation of Formyl Group)

The compound (I-u) or salts thereof can be prepared by oxidizing the formyl group of the compound (I-n) or salts thereof.

Suitable salts of the compound (I-u) may be the same as those for the compounds (I).

Suitable oxidizing agent of the formyl group used in this reaction may be a conventional one which is capable of converting a formyl group to a carboxy group such as potassium permanganate, chromic compound (e.g. chromium trioxide, chromic acid, sodium chromate, dichromic acid, sodium dichromate, pyridinium dichromate, etc.), and the like.

This oxidation can be carried out in the presence of an acid such as those given in the explanation of the Process 14, preferably sulfuric acid.

The reaction is usually carried out in a conventional solvent which does not adversely influence the reaction such as water, acetone, dioxane, dimethylformamide, pyridine, etc., or a mixture thereof.

The reaction temperature is not critical and the reaction is usually carried out under from cooling to warming.

This process includes, within a scope thereof, a case that during the reaction, the protected imino group for $R^6$ of the starting compound (I-n) may occasionally be eliminated when the oxidation is carried out in the presence of the acid.

(17) Process 17 (Oxidation of Methylene Group)

The compound (I-v) or salts thereof can be prepared by oxidizing the compound (I-k) or salts thereof.

Suitable salts of the compound (I-v) may be the same as those for the compounds (I).

This oxidation can be carried out by reacting the compound (I-k) with ozone, and then degrading the resultant ozonide in a conventional manner, if necessary.

The ozonide produced by reacting the starting compound (I-k) with ozone is usually degraded by reduction.

The reduction can be carried out in substantially the same method as the Process 7, and therefore the reaction conditions of this reduction (e.g. solvent, reaction temperature, etc.) are to be reffered to the explanation for the Process 7.

In addition, as suitable reducing agents, there may be exemplified by trialkyl phosphite (e.g. trimethylphosphite, etc.), triphenylphosphine, dimethyl sulfide, sodium bisulfite, sodium sulfite, sodium iodide, stannous chloride, and the like.

The reaction temperature is not critical and the reaction is usually carried out under from cooling to warming.

(18) Process 18 (Introduction of Carboxy-Protective Group)

The compound (I-w) or salts thereof can be prepared by introducing a carboxy-protective group into the compound (I-u) or salts thereof.

Suitable salts of the compound (I-w) may be the same as those for the compounds (I).

Suitable introducing agent of the carboxy-protective group used in this reaction may include a conventional esterifying agent which can convert a carboxy group to an esterified carboxy group, for example, alcohol or its reactive equivalent such as halide (e.g. chloride, bromide, iodide), sulfonate, sulfate, diazoalkane compound (e.g. diazomethane, diazoethane, etc.), and the like.

This reaction can be carried out in the presence of a base or an acid, and suitable base may be the inorganic base such as those given in the Process 1. Suitable acid may be the inorganic or the organic acid such as those given in the Process 14.

This reaction is usually carried out in a conventional solvent which does not adversely influence the reaction such as water, methanol, ethanol, propanol, diethyl ether, pyridine, N,N-dimethylformamide, etc., or a mixture thereof.

The reaction temperature is not critical and the reaction is usually carried out under from cooling to warming.

(19) Process 19 (Removal of Formyl-Protective Group)

The compound (I-n) or salts thereof can be prepared by removing a formyl-protective group from the compound (I-o) or salts thereof.

This removal reaction can be carried out in a conventional method such as hydrolysis, and the like.

Hydrolysis is usually carried out in a conventional manner which is conventionally applied for cleavage of so-called an acetal function into the corresponding carbonyl function and preferably, for example, hydrolysis is carried out by an acidic hydrolysis, i.e. in the presence of an acid such as an inorganic acid (e.g. hydrochloric acid, sulfuric acid, etc.), an organic acid (e.g. formic acid, acetic acid, trifluoroacetic acid, p-toluenesulfonic acid, etc.) or an acidic ion-exchange resin.

This reaction is usually carried out in a conventional solvent which does not adversely influence the reaction such as water, acetone, methyl ethyl ketone, dioxane, ethanol, methanol, N,N-dimethylformamide, or dimethylsulfoxide, etc., or a mixture thereof.

The reaction temperature is not critical and the reaction is usually carried out under from cooling to warming.

This process includes, within a scope thereof, a case that during the reaction, the imino-protective group for $R^6$ of the starting compound (I-o) may occasionally be eliminated.

(20) Process 20 (Alkylation of Imino Group) The compound (I-x) or salts thereof can be prepared by reacting a compound (I-a) or salts thereof with an alkylating agent.

Suitable salts of the compound (I-x) may be the same as those for the compounds (I).

Suitable alkylating agent used in this reaction may be a conventional one which is capable of alkylating an imino group to an alkylimino group such as those given in the Processes 10 and 11.

This reaction is preferably carried out in the presence of an inorganic or organic base such as those given in the explanation of the Process 1.

This reaction is usually carried out in a conventional solvent which does not adversely influence the reaction such as water, methanol, ethanol, propanol, pyridine, N,N-dimethylformamide, etc., or a mixture thereof.

The reaction temperature is not critical and the reaction is usually carried out under from cooling to warming.

This process includes, within a scope thereof, a case that during the reaction, at least one of the hydroxy groups for $R^2$ and $R^5$ of the starting compound (I-a) may occasionally be transformed into the alkoxy group(s).

(21) Process 21 (Hydrolysis of Protected 6-Hydroxy Group)

The compound (I-c) or salts thereof can be prepared by hydrolysing the compound (I-d) or salts thereof.

This hydrolysis can be carried out by substantially the same method as the Process 14, and therefore the suitable base or acid used in the hydrolysis and reaction conditions (e.g. solvent, reaction temperature, etc.) are to be referred to the explanation for the Process 14.

(22) Process 22 (Introduction of Hydroxy-Protective Group into Hydroxyiminomethyl Group)

The compound (I-z) or salts thereof can be prepared by introducing a hydroxy-protective group into the compound (I-y) or salts thereof.

Suitable salts of the compounds (I-z) and (I-y) may be the same as those for the compounds (I).

Suitable introducing agent of the hydroxy-protective group used in this reaction may be a conventional acylating agent which is capable of introducing an acyl group such as those given in the Process 1.

This reaction can be carried out by substantially the same method as the Process 1, and therefore the reaction method and reaction conditions (e.g. solvent, reaction temperature, etc.) are to be referred to the explanation for the Process 1.

This process includes, within a scope thereof, a case that during the reaction, at least one of the hydroxymethyl group for $R^4$, the hydroxy groups for $R^2$ and $R^5$ and the imino group formed by $R^6$ being hydrogen of the compound (I-y) may occasionally be transformed into the corresponding protected hydroxymethyl, protected hydroxy and protected imino group(s) in the object compound (I-z), respectively.

The object tetracyclo compounds (I) obtained according to the fermentation process and the synthetic processes 1 to 22 as explained above can be isolated and purified in a conventional manner, for example, extraction, precipitation, fractional crystallization, recrystallization, chromatography, and the like.

It is to be noted that in the aforementioned reactions in the synthetic processes 1 to 22 or the post-treatment of the reaction mixture therein, the configuration(s) of the starting or object compounds may occasionally be transformed into the other configuration(s), and such cases are also included within the scope of the present invention.

The tetracyclo compounds (I) and pharmaceutically acceptable salts thereof of this invention are new and exhibit pharmacological activities such as antitumor activity, antimicrobial activity, and the like, and therefore is useful for the treatment of tumors, infectious diseases, and the like in mammals including human being.

In order to show the utility of the tetracyclo compounds (I), pharmacological test data of some representative compounds of the compounds (I) are illustrated in the following.

Test 1

Antitumor activity of FR-900482 substance

The antitumor activity of FR-900482 substance was determined in experimental tumor system in mice.

Lymphocytic leukemia P388 was implanted intraperitoneally into $BDF_1$ mice at an inoculum size of $1 \times 10^6$ cells per mouse. Twenty-four hours after the implantation of tumor cells, graded doses of the FR-900482 substance were administered to mice intraperitoneally. Treatments were once a day on day 1, 2, 3 and 4 after the tumor inoculation. Control animals received intraperitoneal doses of physiological saline solution. The injection volume was 0.2 ml in all experiments. Six mice were used for each experimental group.

Antitumor activity was evaluated by the mean survival time of a group of mice and also expressed by the T/C % value (mean survival time of treated group/mean survival time of control group, x 100).

The results are shown in Table 4.

The FR-900482 substance was quite active against the leukemia P388. Doses between 3.2–18 mg/kg resulted in significant increase in life span in mice.

TABLE 4

| Antitumor activity of the FR-900482 substance | | | |
|---|---|---|---|
| Drug | Dose | Mean Survival time | T/C |
| FR-900482 substance | 18 mg/kg | 29.0 days | 264% |
| | 10 | 24.5 | 223 |
| | 5.6 | 16.0 | 145 |
| | 3.2 | 14.0 | 127 |
| | 1.0 | 13.0 | 118 |
| Control | — | 11.0 | 100 |

Test 2

Antimicrobial activity of the FR-900482 substance

Antimicrobial activity of the FR-900482 substance against some bacteria was determined by a serial broth dilution method in bouillon media for bacteria. Minimum inhibitory concentrations (MIC) were expressed in terms of μg/ml after overnight incubation at 37° C.

The FR-900482 substance showed an antimicrobial activity against various pathogenic microorganisms, for example, *Bacillus subtilis* ATCC 6633 (MIC: μg/ml), *Escherichia coli* NIHJ JC-2 (MIC: 50 μg/ml) and *Pseudomonas aeruginosa* NCTC-10490 (MIC: 25 μg/ml).

Test 3

Acute toxicity of the FR-900482 substance

Test on acute toxicity of the FR-900482 substance in ddY mice by intraperitoneal and intravenous injections were conducted, and the $LD_{50}$ values were each 32 mg/kg.

Test 4 in vitro Cytotoxicity (i) Test Method

A suspension of mouse lymphocytic leukemia P388 tumor cells was prepared from a diluted ascitic fluid using Hanks' solution after 7 days of tumor implantation, and centrifuged at 1000 rpm for 15 minutes at cold temperature. The cells were adjusted at a concentration of $2.5 \times 10^6$ cell/ml in MEM Dulbecco medium supplemented with 10% foetal bovine serum, penicillin G (60 μg/ml) and streptomycin (20 μg/ml). Then, cells were treated with the graded doses of the test compounds in plastic tissue culture dishes at 37° C. and incubated for 72 hours in humidified atmosphere of 5% carbon. Concentration of the substance required for 50% inhibition of cell growth ($IC_{50}$ value) (μg/ml) was determined by plotting the logarithms of the drug concentration versus the growth rate (percentage of control) of the treated cells.

(ii) Test Compounds 1   11-Acetyl-4-formyl-8-carbamoyloxymethyl-14-oxa-1,11-diazatetracyclo[7.4.1.0$^{2,7}$.0$^{10,12}$]tetradeca-2,4,6-trien-6,9-diyl diacetate (hereinafter referred to as Compound R), 2   11-Acetyl-4-formyl-9-hydroxy-8-methylene-14-oxa-1,11-diazatetracyclo[7.4.1.0$^{2,7}$.0$^{10,12}$]tetradeca-2,4,6-trien-6-yl acetate (hereinafter referred to as Compound S), 3   11-Acetyl-4-acetoxymethyl-8-carbamoyloxymethyl-9-hydroxy-14-oxa-1,11-diazatetracyclo[7.4.1.0$^{2,7}$.0$^{10,12}$]-tetradeca-2,4,6-trien-6-yl acetate (hereinafter referred to as Compound T), 4   4-Acetoxymethyl-11-acetyl-8-carbamoyloxymethyl-14-oxa-1,11-diazatetracyclo[7.4.1.0$^{2,7}$.0$^{10,12}$]tetradeca-2,4,6-trien-6,9-diyl diacetate (hereinafter referred to as Compound U), 11-Acetyl-8-carbamoyloxymethyl-4-formyl-6-methoxy-14-oxa-1,11-diazatetracyclo[7.4.1.0$^{2,7}$.0$^{10,12}$]tetradeca-2,4,6-trien-9-yl acetate (hereinafter referred to as Compound V), 11-Acetyl-4-formyl-9-hydroxy-6-methoxy-14-oxa-1,11-diazatetracyclo[7.4.1.0$^{2,7}$.0$^{10,12}$]tetradeca-2,4,6-trien-8-ylmethyl carbamate (hereinafter referred to as Compound W)

(iii) Test Results

| IC$_{50}$ Values of Test Compound | |
|---|---|
| Test Compounds | IC$_{50}$ (μg/ml) |
| R | 0.05 |
| S | 0.02 |
| T | 0.02 |
| U | 0.01–0.02 |
| V | 0.02 |
| W | 0.01 |

The pharmaceutical composition of this invention can be used in the form of a pharmaceutical preparation, for example, in solid, semisolid or liquid form, which contains the tetracyclo compounds (I), as active ingredients, in admixture with an organic or inorganic carrier or excipient suitable for external, enteral or parenteral applications. The active ingredients may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of diseases.

For applying this composition to human, it is preferable to apply it by parenteral or enteral administration. While the dosage of therapeutically effective amount of the tetracyclo compounds (I) varies from and also depends upon the age and condition of each individual patient to be treated, a daily dose of about 0.1–1000 mg, preferably 0.5–500 mg and more preferably 1–100 mg, of the active ingredients is generally given for treating diseases, and an average single dose of about 1 mg, 5 mg, 10 mg, 50 mg, 100 mg, 250 mg and 500 mg is generally administered.

The following examples are given for the purpose of illustrating the present invention.

EXAMPLE 1

Isolation of *Streptomyces sandaensis* No. 6897

*Streptomyces sandaensis* No. 6897 was isolated by using dilution plate techniques as shown in the following.

About one gram soil which was collected at Sanda City, Hyogo Prefecture, Japan, was added to a sterile test tube and the volume made up to 5 ml with sterile water. The mixture was then blended for 10 second by a tube buzzer and kept on 10 minutes. The supernatant was sequentially diluted by 100 fold with sterile water. The diluted solution (0.1 ml) was spread on Czapek agar supplemented with thiamine hydrochloride (saccharose 30 g, sodium nitrate 3 g, dipotassium phosphate 1 g, magnesium sulfate 0.5 g, potassium chloride 0.5 g, ferrous sulfate 0.01 g, thiamine hydrochloride 0.1 g, agar 20 g, tap water 1000 ml; pH 7.2) in a Petri dish. The growing colonies developed on the plates after 21 days incubation at 30° C. were transferred to slants [yeast-malt extract agar (ISP-medium 2)], and cultured for 10 days at 30° C. Among of the colonies isolated, the *Streptomyces sandaensis* No. 6897 could be found.

Fermentation

A seed medium (160 ml) containing soluble starch (2%), glucose (0.5%), cottonseed meal (1%), dried yeast (1%), corn steep liquor (0.5%) and calcium carbonate (0.2%) (adjusted to pH 7.0 with an aqueous sodium hydroxide) was poured into each of eight 500 ml-Erlenmeyer flasks and sterilized at 120° C. for 30 minutes. A loopful of slant culture of *Streptomyces sandaensis* No. 6897, FERM P-7654 was inoculated to each of the media and cultured at 30° C. for 72 hours on a rotary shaker with 3-inch throw at 200 rpm. The resultant culture was inoculated to the same seed medium (20 liters) in a 30-liter jar-fermentor, which had been sterilized at 120° C. for 30 minutes in advance, and cultured at 30° C. for 48 hours under aeration of 20 liters/minutes and agitation of 200 rpm. Eighteen liters of the seed culture were inoculated to a production medium (1760 liters) containing soluble starch (8%), dried yeast (1%), peanut powder (3%) and soybean meal (0.5%) (adjusted to pH 6.2 with sulfuric acid) in a 2000-liter stainless steel fermentor, which had been sterilized at 120° C. for 30 minutes, and cultured at 31° C. for 96 hours under aeration of 880 liters/minutes and agitation of 130 rpm.

Isolation and Purification

The cultured broth thus obtained was filtered with an aid of diatomaseous earth (125 kg). The filtrate obtained (1600 liters) was passed through a column filled with a non-ionic adsorption resin "Diaion HP-20" (Trade Mark, made by Mitsubishi Chemical Industries Ltd.) (400 liters). This column was washed with water (400 liters) and eluted with 50% aqueous methanol (1200 liters). The active eluate was concentrated in vacuo to a volume of 300 liters. The active fraction was charged with an ion-exchange resin "Amberlite IRC-50" (Trade Mark, made by Rohm & Haas Chemical Co.) (H+form) (300 liters). This column was washed with deionized water (600 liters) and eluted with 0.1N hydrochloric acid (1200 liters). The eluate was neutralized with 12N aqueous sodium hydroxide, and then passed through a column filled with a non-ionic adsorption resin "Diaion HP-20" (200 liters). The column was washed with deionized water (200 liters) and eluted with 50% aqueous methanol (600 liters). The active eluate was concentrated in vacuo to a volume of 10 liters, and thereto was added 15 liters of n-butanol and then stirred for 10 minutes. This extraction procedure was carried out four times and the obtained extracts were combined (60 liters). Then, to the combined butanol extracts was added 240 liters of n-hexane and stirred for 10 minutes. After separating the aqueous layer, to the butanol-n-hexane layer was added 15 liters of deionized water and stirred for 10 minutes. The aqueous layers were combined and concentrated in vacuo to a volume of 6 liters, and applied to a column filled with "Alumina Oxide AC-11" (Trade Mark, made by Sumitomo Chemical Co., Ltd.) (100 liters). The column was developed with 80% aqueous isopropyl alcohol and the active eluate was concentrated in vacuo to a volume of 300 ml. The active fraction was subjected to column chromtography on "Toyopearl HW-40 Fine" (Trade Mark, made by Toyo Soda Manufacturing Co., Ltd.) (7 liters) using deionized water as a developing agent. Fractions containing active materials (30 liters) were concentrated in vacuo to a volume of 500 ml and then lyophilized to give a crude powder. The crude powder was dissolved in deionized water so as to make its final concentration become 50 mg/ml and subjected to high performance liquid chromatography (hereinafter referred to as HPLC). HPLC was carried out using "Waters Model 6000A" pump with "Waters Model U6K" injector (Trade Mark, maker: Waters Associates, Inc.). Chromatography was monitored by UV detector, "Waters Model 440" (Trade Mark, maker: Water Associates, Inc.) at 254 nm. A steel column (7.9 mm inside diameter, 30 mm length) packed with "μBondapak C18" (Trade mark, maker: Waters Associates, Inc.) was used at a flow rate of 6 ml/minute. Mobile phase was a mixture of methanol and distilled water (1:9). HPLC under the above mentioned conditions gave the active fraction (retention time: 8 minutes). One gram of colorless powder of the FR-900482 substance was obtained.

EXAMPLE 2

The FR-900482 substance (57 mg) was dissolved in water (2 ml) and 1N hydrochloric acid (0.3 ml) was added thereto. The solution was allowed to stand at room temperature for 30 minutes and then lyophilized. The resultant powder was dried over phosphorus pentoxide in vacuo and then dried over potassium hydroxide pellets in vacuo to give a colorless powder of the FR-900482A substance (60 mg).

This FR-900482A substance (5 mg) was dissolved in water (0.4 ml), and 0.1N aqueous sodium hydroxide (100 μl) was added thereto. After the mixture was allowed to stand at room temperature for an hour, the solution was spotted on silica gel plate and developed with several solvent systems. The resultant substance showed the same Rf values as those of the FR-900482 substance in silica gel thin layer chromatography.

EXAMPLE 3

To the FR-900482 substance (25 mg) were added pyridine (2 ml) and acetic anhydride (1 ml). After shaking for 20 minutes, the resultant solution was allowed to stand overnight at room temperature. Excess of the solvent was removed under reduced pressure by using high vacuum pump. The residue was purified by preparative thin layer chromatography on silica gel, which was developed with a mixed solvent of methanol and chloroform (5:95) to obtain the triacetyl derivative of the FR-900482 substance (20 mg) as a colorless powder. The obtained powder was crystalized from a mixture of ethyl acetate and diethyl ether to give colorless platelet of the above substance.

This triacetyl derivative of the FR-900482 substance (20 mg) was dissolved in methanol (1 ml), and thereto was added 10% aqueous sodium bicarbonate (1 ml). After stirring at room temperature overnight, the resultant mixture was subjected to preparative thin layer chromatography using a mixture of chloroform and methanol (4:1, v/v) as a developing solvent to give the FR-900482 substance (10 mg), which was identified by comparison of the silica gel thin layer chromatography (developing solvent: mixture of chloroform and methanol, and a mixture of isopropyl alcohol and water) and infrared absorption spectrum.

EXAMPLE 4

The FR-900482 substance (100 mg) was dissolved in water (3 ml), and acetic anhydride (30 μl) was added thereto. After stirring at room temperature for 3 hours, the resultant mixture was subjected to preparative thin layer chromatography using a mixture of chloroform and acetone (1:1, v/v) as a developing solvent to give the monoacetyl derivative of the FR-900482 substance (58.5 mg).

(1) Specific Rotation: $[\alpha]_D^{23}$: +41° (c=1.02, CH$_3$OH)
(2) Infrared Absorption Spectrum: $\nu_{max}^{KBr}$: 3600-3000, 1680, 1580, 1340 cm$^{-1}$
(3) Molecular Weight: SI Mass: m/z 364 (M+1), 386 (M+23)
(4) $^1$H Nuclear Magnetic Resonance: δ(ppm, CD$_3$OD): 9.9 (1H, s), 7.0 (1H, d, J=2 Hz), 6.9 (1H, d, J=2 Hz), 4.7–4.5 (2H, m), 3.85–3.75 (2H, m), 2.9 (1H, d, J=6 Hz), 1.85 (3H, s)

EXAMPLE 5

Measurement of the mixture ratios of the two components of the FR-900482 substance under various pH values The FR-900482 substance was dissolved in various buffer solutions so as to make its concentration to 10 mg/ml. After allowing to stand for 2 hour, 4 μl of each of these solutions was subjected to silica gel thin layer chromatography using a mixture of chloroform and methanol (4:1, v/v) as a developing solvent. After developing, the mixture ratios of the two components were calculated by a chromatoscanner at 254 nm, the results of which are shown in the following.

| pH Values | Buffer Solution | Ratios of the two components* |
|---|---|---|
| 1.0 | 0.1 N hydrochloric acid | single component |
| 2.0 | 0.1 M sodium acetate-hydrochloric acid | about 12:1 |
| 4.0 | 0.1 M sodium acetate-hydrochloric acid | about 6:1 |
| 7.0 | 0.1 M potassium phosphate-disodium phosphate | about 2.3:1 |
| 9.0 | 0.1 M trisaminomethane-hydrochloric acid | about 3:1 |

Note*: The single component in pH 1 and the component described in the left side of pH 2.0, 4.0, 7.0, 9.0 correspond to that showing Rf value 0.20 in the silica gel thin layer chromatography using a mixture of chloroform and methanol as the developing solvent, and the other component described in the right side in pH 2.0, 4.0, 7.0 and 9.0 corresponds to that showing Rf value 0.45 in the same thin layer chromatography as mentioned above.

EXAMPLE 6

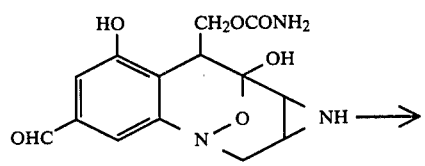

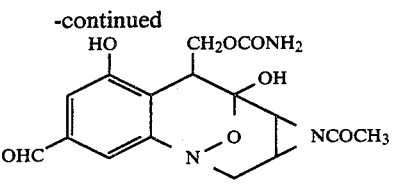

4-Formyl-6,9-dihydroxy-14-oxa-1,11-diazatetracyclo[7.4.1.0$^{2,7}$.0$^{10,12}$]tetradeca-2,4,6-trien-8-ylmethyl carbamate (100 mg) was dissolved in water (3 ml). To this solution was added acetic anhydride (30 μl), and the mixture was stirred at room temperature for 3 hours. The reaction mixture was subjected to preparative thin layer chromatography, which was developed with a mixture of chloroform and acetone (1:1, v/v) to afford 11-acetyl-4-formyl-6,9-dihydroxy-14-oxa-1,11-diazatetracyclo[7.4.1.0$^{2,7}$.0$^{10,12}$]tetradeca-2,4,6-trien-8-ylmethyl carbamate (80.5 mg).

$^1$H NMR δ(ppm, CD$_3$OD): 9.9 (1H, s), 7.00 (1H, d, J=2 Hz), 6.9 (1H, d, J=2 Hz), 4.7–4.5 (2H, m), 3.85–3.75 (2H, m), 3.00–2.85 (1H, m), 1.85 (3H, s)

IR ν$_{max}$$^{KBr}$: 3600–3000, 1680, 1580, 1340 cm$^{-1}$

SI Mass: m/z 364 (M$^+$+1)

EXAMPLE 7

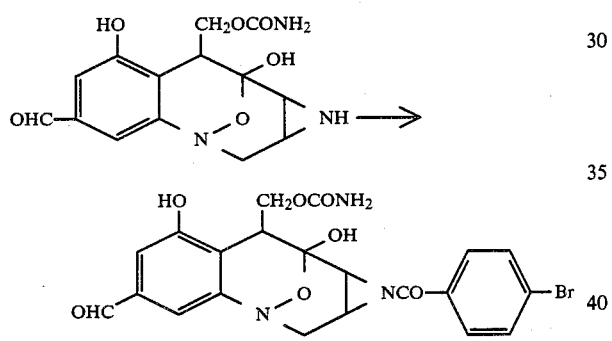

To a solution of 4-formyl-6,9-dihydroxy-14-oxa-1,11-diazatetracyclo[7.4.1.0$^{2,7}$.0$^{10,12}$]tetradeca-2,4,6-trien-8-ylmethyl carbamate (50 mg) in pyridine (2 ml) was added 4-bromobenzoyl chloride (170 mg), and the mixture was stirred at room temperature for 1 hour. The resultant solution was allowed to stand at room temperature overnight and then the solvent was evaporated off in vacuo. To the residue was added an aqueous sodium bicarbonate and the mixture was extracted with ethyl acetate. The ethyl acetate solution was evaporated to dryness to give a residue (52 mg), which was subjected to preparative thin layer chromatography. Development was carried out with a mixture of methanol and chloroform (1:9, v/v) to afford 11-(4-bromobenzoyl)-4-formyl-6,9-dihydroxy-14-oxa-1,11-diazatetracyclo[7.4.1.0$^{2,7}$.0$^{10,12}$]tetradeca-2,4,6-trien-8-ylmethyl carbamate (26 mg).

$^1$H NMR δ(ppm, CD$_3$OD+CDCl$_3$): 9.88 (1H, s), 7.50 (2H, d, J=8.5 Hz), 7.33 (2H, d, J=8.5 Hz), 7.02 (1H, d, J=1.3 Hz), 6.99 (1H, d, J=1.3 Hz), 4.65 (2H, m), 3.97 (1H, dd, J=2, 15 Hz), 3.90 (1H, d, J=15 Hz), 3.40 (2H, m), 2.90 (1H, dd, J=2,7 Hz)

IR ν$_{max}$$^{KBr}$: 3350, 1680, 1580, 1340, 1280, 1080, 1065, 840 cm$^{-1}$

SI Mass: m/z 506 (M$^+$+3), 504 (M$^+$+1)

EXAMPLE 8

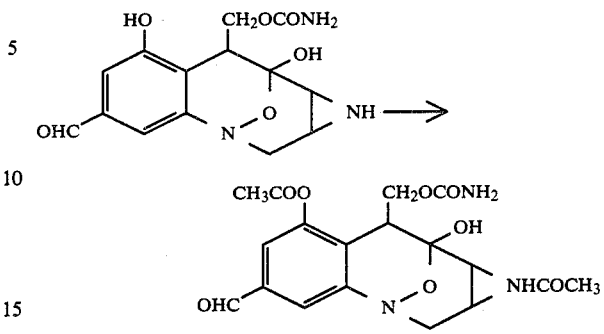

To a solution of 4-formyl-6,9-dihydroxy-14-oxa-1,11-diazatetracyclo[7.4.1.0$^{2,7}$.0$^{10,12}$]tetradeca-2,4,6-trien-8-ylmethyl carbamate (20 mg) in methanol (2 ml) was added acetic anhydride (1 ml), and the mixture was stirred at room temperature for 1 hour. The solvent and the excess of acetic anhydride was removed in vacuo to give a residue, which was subjected to preparative thin layer chromatography. Development was carried out with a mixture of methanol and chloroform (1:9, v/v) to afford 11-acetyl-8-carbamoyloxymethyl-4-formyl-9-hydroxy-14-oxa-1,11-diazatetracyclo[7.4.1.0$^{2,7}$.0$^{10,12}$]tetradeca-2,4,6-trien-6-yl acetate (9 mg).

$^1$H NMR δ(ppm, CDCl$_3$): 9.9 (1H, s), 7.31 (1H, d, J=1.5 Hz), 7.17 (1H, d, J=1.5 Hz), 6.70 (1H, s), 5.06 (1H, dd, J=2, 12.7 Hz), 4.78 (2H, broad), 4.35 (1H, dd, J=5, 12.7 Hz), 3.96 (1H, dd, J=2, 14.7 Hz), 3.71 (1H, d, J=14.7 Hz), 3.19 (1H, d, J=6.5 Hz), 3.15 (1H, dd, J=2, 5 Hz), 2.81 (1H, dd, J=2, 6.5 Hz), 2.40 (3H, s), 1.90 (3H, s)

IR ν$_{max}$$^{CHCl_3}$: 3550, 3450, 1770, 1705, 1580, 1400, 1370, 1355, 1335, 1190 cm$^{-1}$ SI Mass: m/z 406 (M$^+$+1)

EXAMPLE 9

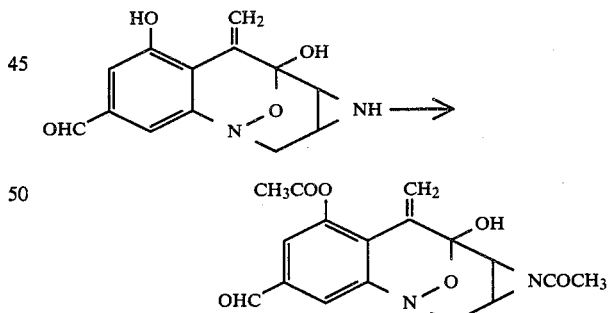

To a solution of 6,9-dihydroxy-8-methylene-14-oxa-1,11-diazatetracyclo[7.4.1.0$^{2,7}$.0$^{10,12}$]tetradeca-2,4,6-triene-4-carbaldehyde (20 mg) in pyridine (500 μl) was added acetic anhydride (16 μl), and the mixture was allowed to stand at room temperature overnight. The reaction mixture was evaporated to dryness in vacuo to give an oil, which was subjected to silica gel column chromatography. Elution was carried out with a mixture of methanol and chloroform (5:95, v/v). The desired fractions were combined and then evaporated to dryness in vacuo to afford 11-acetyl-4-formyl-9-hydroxy-8-methylene-14-oxa-1,11-diazatetracyclo[7.4.1.0$^{2,7}$.0$^{10,12}$]tetradeca-2,4,6-trien-6-yl acetate (19.5 mg).

$^1$H NMR δ(ppm, CDCl$_3$): 9.85 (1H, s), 7.27 (1H, d, J=1.5 Hz), 7.20 (1H, d, J=1.5 Hz), 6.21 (1H, s), 6.14 (1H, s), 4.50 (1H, broad s), 3.87 (1H, dd, J=15, 2 Hz), 3.61 (1H, dd, J=15, 6.4 Hz), 2.93 (1H, ddd, J=6.4, 6.4, 2 Hz), 2.77 (1H, d, J=6.4 Hz), 2.31 (3H, s), 2.18 (3H, s)

IR ν$_{max}$$^{CHCl_3}$: 3550, 1770, 1700, 1560, 1360, 1180 cm$^{-1}$

EI Mass: m/z 344 (M+)

EXAMPLE 10

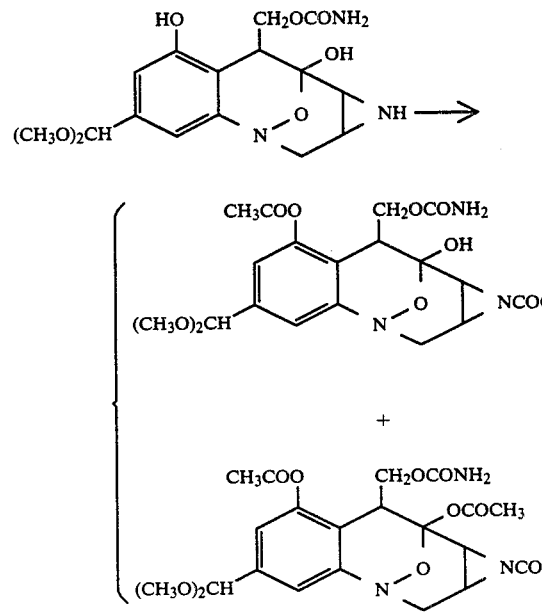

To a solution of 6,9-dihydroxy-4-dimethoxymethyl-14-oxa-1,11-diazatetracyclo[7.4.1.0$^{2,7}$.0$^{10,12}$]tetradeca-2,4,6-trien-8-ylmethyl carbamate (35 mg) in pyridine (1 ml) was added acetic anhydride (100 μl), and the mixture was allowed to stand at room temperature overnight. After the reaction mixture was evaporated to dryness in vacuo, the residual oil was subjected to preparative thin layer chromatography, which was developed with a mixture of methanol and chloroform (1:9, v/v) to afford 11-acetyl-8-carbamoyloxymethyl-9-hydroxy-4-dimethoxymethyl-14-oxa-1,11-diazatetracyclo[7.4.1.0$^{2,7}$.0$^{10,12}$]tetradeca-2,4,6-trien-6-yl acetate (22 mg).

$^1$H NMR δ(ppm, CDCl$_3$+CD$_3$OD): 6.88 (1H, d, J=2 Hz), 6.77 (1H, d, J=2 Hz), 5.37 (1H, s), 4.53 (1H, dd, J=12, 3 Hz), 3.87 (1H, dd, J=15, 2 Hz), 3.73 (1H, d, J=15 Hz), 3.30 (6H, s), 3.20 (1H, d, J=6 Hz), 2.83 (1H, dd, J=6, 2 Hz), 2.33 (3H, s), 1.89 (3H, s)

IR ν$_{max}$$^{CHCl_3}$: 3550, 3450, 2950, 1770, 1710, 1360, 1200, 1100 cm$^{-1}$ EI Mass: m/z 451 (M+)

Further, 11-acetyl-8-carbamoyloxymethyl-4-dimethoxymethyl-14-oxa-1,11-diazatetracyclo[7.4.1.0$^{2,7}$.0$^{10,12}$]tetradeca-2,4,6-trien-6,9-diyl diacetate (11 mg) was also afforded from the same preparative thin layer chromatography.

$^1$H NMR δ(ppm, CDCl$_3$): 6.92 (1H, d, J=2 Hz), 6.77 (1H, d, J=2 Hz), 5.37 (1H, s), 4.37 (2H, d, J=6 Hz), 4.03 (1H, dd, J=15, 2 Hz), 3.83 (1H, t, J=6 Hz), 3.73 (1H, d, J=15 Hz), 3.41 (1H, d, J=6 Hz), 3.30 (6H, s), 2.80 (1H, dd, J=6, 2 Hz), 2.33 (3H, s), 2.23 (3H, s), 1.97 (3H, s)

IR ν$_{max}$$^{CHCl_3}$: 3550, 3450, 2950, 1760, 1735, 1700, 1340, 1190 cm$^{-1}$ EI Mass: m/z 493 (M+)

EXAMPLE 11

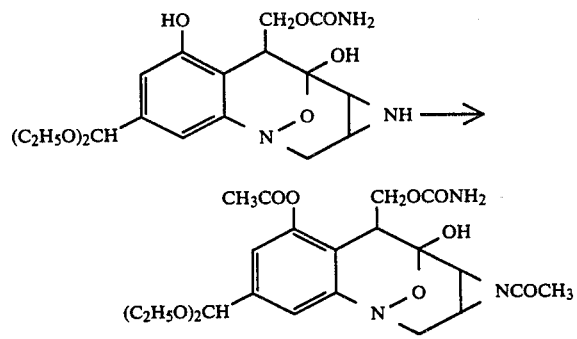

To a solution of 4-diethoxymethyl-6,9-dihydroxy-14-oxa-1,11-diazatetracyclo[7.4.1.0$^{2,7}$.0$^{10,12}$]tetradeca-2,4,6-trien-8-ylmethyl carbamate (17 mg) in pyridine (1 ml) was added acetic anhydride (20 μl), and the mixture was allowed to stand at room temperature overnight. After the reaction mixture was evaporated to dryness, the residual oil was subjected to preparative thin layer chromatography, which was developed with a mixture of methanol and chloroform (5:95, v/v) to give 11-acetyl-8-carbamoyloxymethyl-4-diethoxymethyl-9-hydroxy-14-oxa-1,11-diazatetracyclo[7.4.1.0$^{2,7}$.0$^{10,12}$]tetradeca-2,4,6-trien-6-yl acetate (7 mg).

$^1$H NMR δ(ppm, CDCl$_3$): 6.87 (1H, d, J=2 Hz), 6.77 (1H, d, J=2 Hz), 5.43 (1H, s), 4.90 (1H, dd, J=12, 2 Hz), 4.33 (1H, dd, J=12, 6 Hz), 3.87 (1H, dd, J=15, 2 Hz), 3.63 (1H, d, J=15 Hz), 3.53 (4H, q, J=7 Hz), 3.10 (1H, d, J=6 Hz), 3.07 (1H, dd, J=6, 2 Hz), 2.73 (1H, dd, J=6, 2 Hz), 2.33 (3H, s), 1.83 (3H, s), 1.17 (6H, t, J=7 Hz)

IR ν$_{max}$$^{CHCl_3}$: 3550, 3450, 1760, 1700, 1580, 1400, 1190 cm$^{-1}$

EI Mass: m/z 479 (M+)

EXAMPLE 12

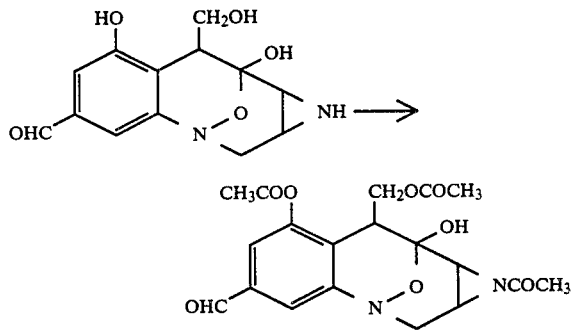

6,9-Dihydroxy-8-hydroxymethyl-14-oxa-1,11-diazatetracyclo[7.4.1.0$^{2,7}$.0$^{10,12}$]tetradeca-2,4,6-triene-4-carbaldehyde (4 mg) was dissolved in pyridine (1 ml). To this solution was added acetic anhydride (50 μl) and the mixture was allowed to stand at room temperature overnight. The reaction mixture was evaporated to dryness in vacuo and the residual oil was subjected to preparative thin layer chromatography, which was developed with a mixture of methanol and chloroform (5:95, v/v) to yield 8-acetoxymethyl-11-acetyl-4-formyl-9-hydroxy-14-oxa-1,11-diazatetracyclo[7.4.1.0$^{2,7}$.0$^{10,12}$]tetradeca-2,4,6-trien-6-yl acetate (1.5 mg).

$^1$H NMR δ(ppm, CDCl$_3$): 9.90 (1H, s), 7.31 (1H, d, J=2 Hz), 7.15 (1H, d, J=2 Hz), 5.65 (1H, s), 4.97 (1H, dd, J=12, 2 Hz), 4.32 (1H, dd, J=12, 6.7 Hz), 3.94 (1H, dd, J=15, 2 Hz), 3.72 (1H, d, J=15 Hz), 3.25 (1H, dd, J=6.7, 2 Hz), 3.18 (1H, d, J=6.5 H), 2.80 (1H, dd, J=6.5, 2 Hz), 2.39 (3H, s), 2.07 (3H, s), 1.88 (3H, s)

IR ν$_{max}^{CHCl_3}$: 3550, 2940, 1770, 1700, 1370, 1190 cm$^{-1}$

EI Mass: m/z 404 (M$^+$)

EXAMPLE 13

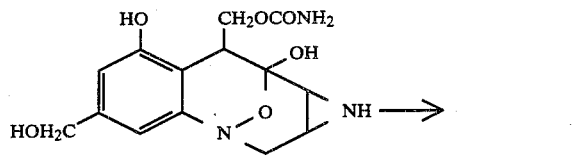

To a solution of 6,9-dihydroxy-4-hydroxymethyl-14-oxa-1,11-diazatetracyclo[7.4.1.0$^{2,7}$.0$^{10,12}$]tetradeca-2,4,6-trien-8-ylmethyl carbamate (21 mg) in pyridine (1 ml) was added acetic anhydride (34 μl), and the mixture was allowed to stand at room temperature overnight. The reaction mixture was evaporated to dryness in vacuo, and the residual oil was subjected to preparative thin layer chromatography, which was developed with a mixture of methanol and chloroform (5:95, v/v) to give 4-acetoxymethyl-11-acetyl-8-carbamoyloxymethyl-9-hydroxy-14-oxa-1,11-diazatetracyclo[7.4.1.0$^{2,7}$.0$^{10,12}$]tetradeca-2,4,6-trien-6-yl acetate (24 mg).

$^1$H NMR δ(ppm, CDCl$_3$): 6.77 (1H, d, J=2 Hz), 6.63 (1H, d, J=2 Hz), 5.03 (2H, s), 4.87 (1H, dd, J=12, 2 Hz), 4.33 (1H, dd, J=12, 5 Hz), 3.90 (1H, dd, J=15, 2 Hz), 3.63 (1H, d, J=15 Hz), 3.20–3.05 (2H, m), 2.77 (1H, dd, J=6, 2 Hz), 2.33 (3H, s), 2.10 (3H, s), 1.87 (3H, s)

IR ν$_{max}^{CHCl_3}$: 3550, 3350, 3000, 1760, 1735, 1700, 1580, 1200 cm$^{-1}$

EI Mass: m/z 449 (M$^+$)

EXAMPLE 14

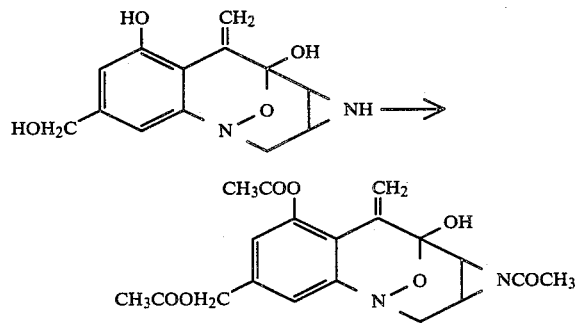

4-Hydroxymethyl-8-methylene-14-oxa-1,11-diazatetracyclo[7.4.1.0$^{2,7}$.0$^{10,12}$]tetradeca-2,4,6-triene-6,9-diol (10 mg) was dissolved in pyridine (1 ml). To this solution was added acetic anhydride (100 μl), and the mixture was allowed to stand at room temperature overnight. The reaction mixture was evaporated to dryness in vacuo and the residual oil was subjected to preparative thin layer chromatography, which was developed with a mixture of methanol and chloroform (5:95, v/v) to give 4-acetoxymethyl-11-acetyl-9-hydroxy-8-methylene-14-oxa-1,11-diazatetracyclo[7.4.1.0$^{2,7}$.0$^{10,12}$]tetradeca-2,4,6-trien-6-yl acetate (6 mg).

$^1$H NMR δ(ppm, CDCl$_3$): 6.80 (1H, d, J=2 Hz), 6.73 (1H, d, J=2 Hz), 6.07 (1H, s), 6.03 (1H, s), 5.00 (2H, s), 3.83 (1H, dd, J=15, 2 Hz), 3.63 (1H, dd, J=15, 6 Hz), 3.00 (1H, ddd, J=6, 6, 2 Hz), 2.80 (1H, d, J=6 Hz), 2.30 (3H, s), 2.20 (3H, s), 2.07 (3H, s)

IR ν$_{max}^{CHCl_3}$: 3550, 3000, 1770, 1735, 1700, 1620, 1560, 1360, 1190 cm$^{-1}$ EI Mass: m/z 388 (M$^+$)

EXAMPLE 15

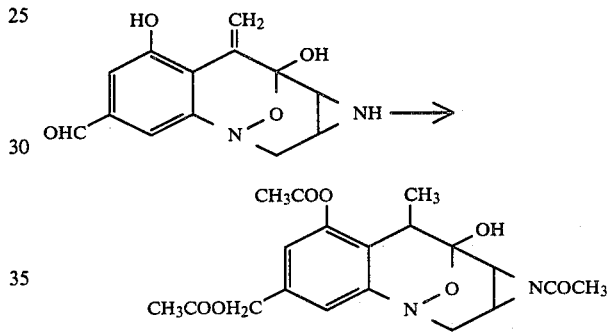

6,9-Dihydroxy-8-methylene-14-oxa-1,11-diazatetracyclo[7.4.1.0$^{2,7}$.0$^{10,12}$]tetradeca-2,4,6-triene-4-carbaldehyde (5 mg) was dissolved in methanol (2 ml), and the solution was subjected to catalytic reduction for 120 minutes using 10% palladium on carbon in hydrogen gas under atmospheric pressure at room temperature. The reaction mixture was filtered and the filtrate was evaporated to dryness to give an oily residue of 4-hydroxymethyl-8-methyl-14-oxa-1,11-diazatetracyclo[7.4.1.0$^{2,7}$.0$^{10,12}$]tetradeca-2,4,6-triene-6,9-diol. This oil was dissolved in pyridine (1 ml) and to this solution was added acetic anhydride (20 μl), followed by allowing to stand at room temperature overnight. The resultant mixture was evaporated to dryness to give an oil, which was subjected to preparative thin layer chromatography. Development was carried out with a mixture of methanol and chloroform (5:95, v/v) to afford 4-acetoxymethyl-11-acetyl-9-hydroxy-8-methyl-14-oxa-1,11-diazatetracyclo[7.4.1.0$^{2,7}$.0$^{10,12}$]tetradeca-2,4,6-trien-6-yl acetate (3 mg).

$^1$H NMR δ(ppm, CDCl$_3$): 6.74 (1H, d, J=2 Hz), 6.61 (1H, d, J=2 Hz), 5.02 (2H, s), 3.90 (1H, dd, J=14.5, 2.3 Hz), 3.68 (1H, d, J=14.5 Hz), 3.13 (1H, d, J=6 Hz), 3.04 (1H, q, J=7 Hz), 2.82 (1H, dd, J=6, 2 Hz), 2.33 (3H, s), 2.10 (3H, s), 1.94 (3H, s), 1.31 (3H, d, J=7 Hz)

IR ν$_{max}^{CHCl_3}$: 3550, 2940, 1760, 1730, 1690, 1360, 1190 cm$^{-1}$

EI Mass: m/z 390 (M$^+$)

EXAMPLE 16

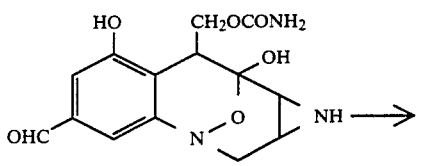

A solution of 4-formyl-6,9-dihydroxy-14-oxa-1,11-diazatetracyclo[7.4.1.0²,⁷.0¹⁰,¹²]tetradeca-2,4,6-trien-8-ylmethyl carbamate (140 mg) in methanol (10 ml) was subjected to catalytic reduction for 120 minutes using 10% palladium on carbon in hydrogen gas under atmospheric pressure at room temperature. The reaction mixture was filtered and the filtrate was evaporated to dryness in vacuo to give 6,9-dihydroxy-4-hydroxymethyl-14-oxa-1,11-diazatetracyclo[7.4.1.0²,⁷.0¹⁰,¹²]tetradeca-2,4,6-trien-8-ylmethyl carbamate (105 mg).

$^1$H NMR δ(ppm, DCl+D₂O, pD=ca.1): 6.68 (1H, s), 6.55 (1H, s), 5.22 (1H, dd, J=11.5, 6 Hz), 4.67 (1H, dd, J=11.5, 1.5 Hz), 4.54 (2H, s), 4.16 (1H, d, J=16 Hz), 4.06 (1H, dd, J=16, 5.7 Hz), 3.80–3.64 (3H, m)

$^{13}$C NMR δ(ppm, DCl+D₂O, pD=ca.1): 159.3 (s), 155.7 (s), 146.6 (s), 142.3 (s), 110.8 (d), 110.4 (d), 110.3 (s), 90.9 (s), 63.6 (t), 61.0 (t), 49.6 (t), 43.6 (d), 36.3 (d), 36.2 (d)

IR $ν_{max}^{KBr}$: 3300, 1680, 1580, 1420, 1340, 1080 cm$^{-1}$

SI Mass: m/z 324 (M$^+$+1)

EXAMPLE 17

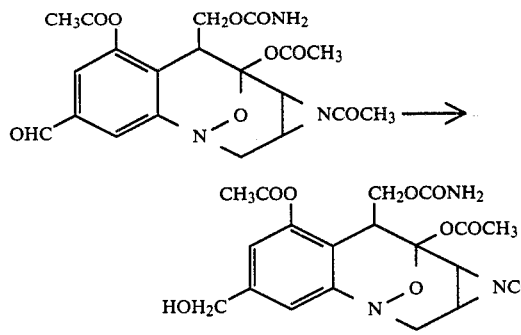

11-Acetyl-4-formyl-8-carbamoyloxymethyl-14-oxa-1,11-diazatetracyclo[7.4.1.0²,⁷.0¹⁰,¹²]tetradeca-2,4,6-trien-6,9-diyl diacetate (20 mg) was dissolved in ethyl acetate (5 ml) and the solution was subjected to catalytic reduction for 2 hours using 10% palladium on carbon under atmospheric pressure at room temperature. The reaction mixture was filtered and the filtrate was evaporated to dryness in vacuo. The residual oil was subjected to preparative thin layer chromatography, which was developed with a mixture of methanol and chloroform (5:95, v/v) to yield 11-acetyl-8-carbamoyloxymethyl-4-hydroxymethyl-14-oxa-1,11-diazatetracyclo[7.4.1.0²,⁷.0¹⁰,¹²]tetradeca-2,4,6-trien-6,9-diyl diacetate (17 mg).

$^1$N NMR δ (ppm, CDCl₃+CD₃OD): 6.80 (1H, s), 6.70 (1H, s), 4.57 (2H, s), 4.10–3.70 (3H, m), 3.50 (1H, d, J=6 Hz), 2.83 (1H, dd, J=6,2 Hz), 2.33 (3H, s), 2.23 (3H, s), 1.97 (3H, s)

IR $ν_{max}^{CHCl_3}$: 3550, 3450, 3000, 1740, 1580, 1370, 1340, 1200, 1100 cm$^{-1}$ EI Mass: m/z 449 (M$^+$)

EXAMPLE 18

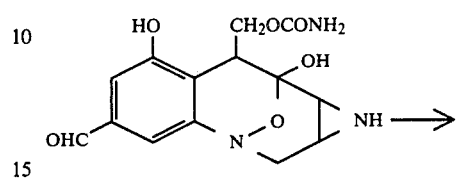

To a solution of 4-formyl-6,9-dihydroxy-14-oxa-1,11-diazatetracyclo[7.4.1.0²,⁷.0¹⁰,¹²]tetradeca-2,4,6-trien-8-ylmethyl carbamate (30 mg) in methanol (3 ml) was added sodium borohydride (40 mg), and the mixture was stirred at room temperature for 1 hour. After evaporation of the solvent, the residue was subjected to column chromatography on non-ionic adsorption resin "Diaion HP-20" (Trade Mark, maker Mitsubishi Chemical Industries Ltd.). Elution was carried out with 50% methanol, and fractions containing the desired compound were collected. The solvent was evaporated off to give 6,9-dihydroxy-4-hydroxymethyl-14-oxa-1,11-diazatetracyclo[7.4.1.0²,⁷.0¹⁰,¹²]tetradeca-2,4,6-trien-8-ylmethyl carbamate, which was dissolved in pyridine (1 ml). To this solution was added acetic anhydride (0.5 ml), and the resultant solution was allowed to stand at room temperature overnight. Removal of the solvent by using high vacuum pump gave an oil, which was subjected to preparative thin layer chromatography. Development was carried out with a mixture of methanol and chloroform (1:9, v/v) to afford 4-acetoxymethyl-11-acetyl-8-carbamoyloxymethyl-14-oxa-1,11-diazatetracyclo[7.4.1.0²,⁷.0¹⁰,¹²]tetradeca-2,4,6-trien-6,9-diyl diacetate (12 mg).

$^1$H NMR δ (ppm, CDCl₃): 6.78 (1h, d, J=1.3 Hz), 6.62 (1H, d, J=1.3 Hz), 5.02 (2H, s), 4.65 (2H, broad s), 4.33 (2H, d, J=6.2 Hz), 4.01 (1H, dd, J=2.1, 15 Hz), 3.83 (1H, t, J=6.2 Hz), 3.68 (1H, d, J=15 Hz), 3.40 (1H, d, J=6.5 Hz), 2.81 (1H, dd, J=2.1, 6.5 Hz), 2.38 (3H, s), 2.23 (3H, s), 2.21 (3H, s), 2.00 (3H, s)

IR $ν_{max}^{CHCl_3}$: 3530, 3420, 1735, 1700, 1580, 1370, 1335 cm$^{-1}$

EI Mass: m/z 491 (M$^+$)

EXAMPLE 19

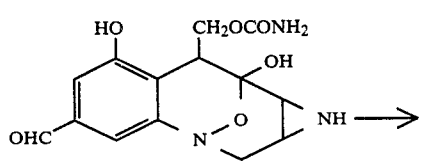

-continued

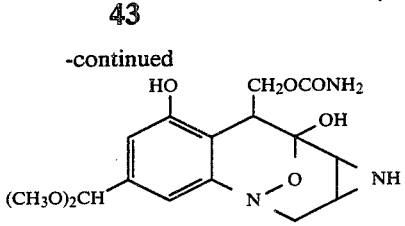

To a solution of 4-formyl-6,9-dihydroxy-14-oxa-1,11-diazatetracyclo[7.4.1.0²,⁷.0¹⁰,¹²]tetradeca-2,4,6-trien-8-ylmethyl carbamate (50 mg) in anhydrous methanol (20 ml) was added anhydrous methanolic hydrogen chloride (hydrogen chloride content: 10% w/w) (200 μl), and the solution was allowed to stand at room temperature overnight. To this solution was added triethylamine (75 μl) and the resultant solution was evaporated to dryness in vacuo. The residue was subjected to preparative thin layer chromatography, which was developed with a mixture of methanol and chloroform (1:4, v/v) to give 6,9-dihydroxy-4-dimethoxymethyl-14-oxa-1,11-diazatetracyclo[7.4.1.0²,⁷.0¹⁰,¹²]tetradeca-2,4,6-trien-8-ylmethyl carbamate (51 mg).

$^1$H NMR δ (ppm, pyridine-$d_5$): 7.13 (1H, s), 6.93 (1H, s), 6.00 (1H, m), 5.50 (1H, m), 5.43 (1H, s), 4.20–3.70 (3H, m), 3.33 (6H, s), 3.10 (1H, m), 2.20 (1H, m)

IR $\nu_{max}^{KBR}$: 3400, 1700, 1420, 1340, 1080 cm$^{-1}$

SI Mass: m/z 368 (M$^+$+1)

EXAMPLE 20

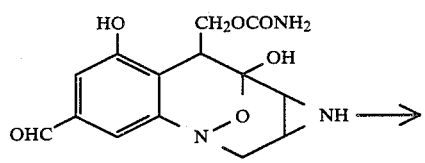

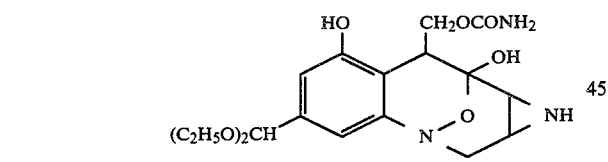

4-Formyl-6,9-dihydroxy-14-oxa-1,11-diazatetracyclo[7.4.1.0²,⁷.0¹⁰,¹²]tetradeca-2,4,6-trien-8-ylmethyl carbamate (75 mg) was dissolved in anhydrous ethanol (20 ml) containing anhydrous ethanolic hydrogen chloride (hydrogen chloride content: 10% w/w) (100 μl) and the solution was allowed to stand at room temperature for 2 hours. The reaction mixture was evaporated to dryness in vacuo, and the residue was subjected to silica gel column chromatography. Elution was carried out with a mixture of methanol and chloroform (1:9, v/v) and the desired fractions were combined and evaporated to dryness to afford 4-diethoxymethyl-6,9-dihydroxy-14-oxa-1,11-diazatetracyclo[7.4.1.0²,⁷.0¹⁰,¹²]tetradeca-2,4,6-trien-8-ylmethyl carbamate (90 mg).

IR $\nu_{max}^{KBr}$: 3300, 1690, 1580, 1400, 1340, 1070, 1050 cm$^{-1}$

SI Mass: m/z 396 (M$^+$+1)

EXAMPLE 21

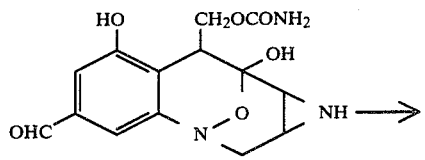

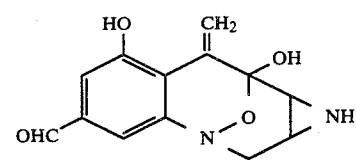

4-Formyl-6,9-dihydroxy-14-oxa-1,11-diazatetracyclo[7.4.1.0²,⁷.0¹⁰,¹²]tetradeca-2,4,6-trien-8-ylmethyl carbamate (40 mg) was dissolved in 1N aqueous sodium hydroxide (4 ml) and the solution was heated at 50° C. for 100 minutes under argon atmosphere. The reaction mixture was cooled and neutralized with 1N aqueous hydrochloric acid (4 ml) and the resultant aqueous solution was lyophilized. The residue was subjected to a silica gel column chromatography and elution was carried out with a mixture of methanol and chloroform (1:4, v/v). The desired fractions were combined and then evaporated to dryness in vacuo to give 6,9-dihydroxy-8-methylene-14-oxa-1,11-diazatetracyclo[7.4.1.0²,⁷.0¹⁰,¹²]tetradeca-2,4,6-triene-4-carbaldehyde (23 mg).

$^1$NMR δ(ppm, CD$_3$OD): 9.81 (1H, s), 7.05 (1H, d, J=1.3 Hz), 6.90 (1H, d, J=1.3 Hz), 6.80 (1H, d, J=1.6 Hz), 6.07 (1H, d, J=1.6 Hz), 3.76–3.68 (2H, m), 2.40 (1H, m), 2.30 (1H, m)

IR $\nu_{max}^{Nujol}$: 3300, 1680, 1570, 1460, 1380, 1260, 1100 cm$^{-1}$

SI Mass: m/z 261 (M$^+$+1)

EXAMPLE 22

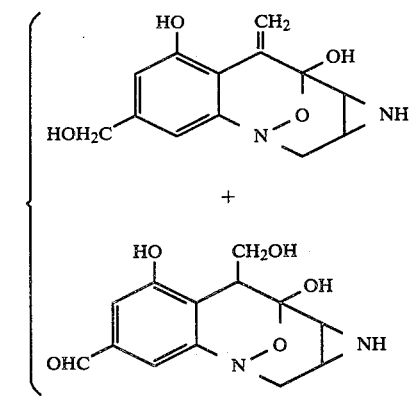

4-Formyl-6,9-dihydroxy-14-oxa-1,11-diazatetracyclo[7.4.1.0²,⁷.0¹⁰,¹²]tetradeca-2,4,6-trien-8-ylmethyl carbamate (100 mg) was dissolved in 1N aqueous sodium hydroxide (10 ml), and the pale yellow solution was allowed to stand at room temperature for 72 hours. The reaction mixture was neutralized with 1N hydrochloric acid and then lyophilized. The residue was subjected to a silica gel column chromatography and elution was carried out with a mixture of methanol and chloroform (1:9, v/v). The desired fractions were combined and then evaporated to dryness in vacuo to give 4-hydroxymethyl-8-methylene-14-oxa-1,11-diazatetracyclo[7.4.1.0$^{2,7}$.0$^{10,12}$]tetradeca-2,4,6-triene-6,9-diol (21 mg).

$^1$H NMR δ (ppm, CD$_3$OD): 6.60 (1H, s), 6.58 (1H, d, J=2 Hz), 6.36 (1H, s), 5.87 (1H, d, J=2 Hz), 4.47 (2H, s), 3.77–3.57 (2H, m), 2.43–2.20 (2H, m)

IR $\nu_{max}^{KBr}$: 3250, 1660, 1600, 1560, 1420, 1180 cm$^{-1}$

SI Mass: m/z 263 (M$^+$+1)

Elution was further carried out with the same solvent system to give 6,9-dihydroxy-8-hydroxymethyl-14-oxa-1,11-diazatetracyclo[7.4.1.0$^{2,7}$.0$^{10,12}$]tetradeca-2,4,6-triene-4-carbaldehyde (4.5 mg).

$^1$H NMR δ(ppm, CD$_3$OD): 9.87 (1H, s), 7.00 (1H, d, J=2 Hz), 6.83 (1H, d, J=2 Hz), 4.50 (1H, dd, J=12, 3 Hz), 4.10 (1H, dd, J=12, 6 Hz), 3.80–3.60 (2H, m), 2.60–2.33 (2H, m)

IR $\nu_{max}^{KBr}$: 3400, 1680, 1570, 1420, 1380, 1140 cm$^{-1}$

SI Mass: m/z 279 (M$^+$+1)

EXAMPLE 23

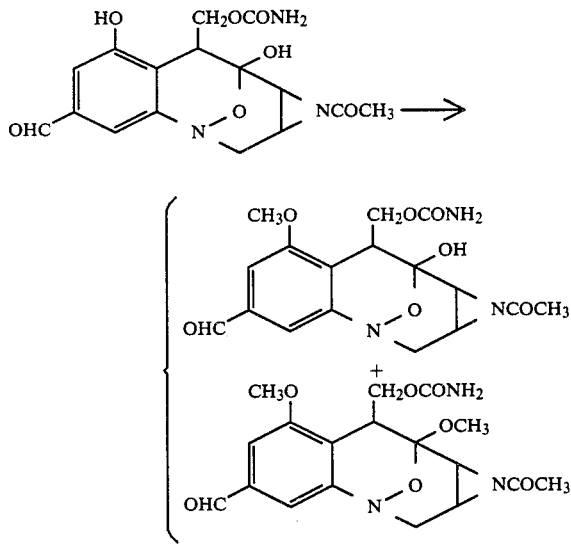

11-Acetyl-4-formyl-6,9-dihydroxy-14-oxa-1,11-diazatetracyclo[7.4.1.0$^{2,7}$.0$^{10,12}$]tetradeca-2,4,6-trien-8-ylmethyl carbamate (55 mg) was dissolved in a mixture of acetone (2 ml) and methyl iodide (2 ml). To the solution was added potassium carbonate (150 mg), and the mixture was stirred at 45° C. overnight under nitrogen atmosphere. The mixture was cooled to room temperature and filtered, and the filter cake was washed with a mixture of chloroform and acetone (1:1, v/v, 10 ml). The filtrate and the washings were combined and evaporated in vacuo. The residue was subjected to column chromatography on silica gel, and elution was carried out with a mixture of chloroform and acetone (4:1, v/v). The desired fractions were collected and evaporated to dryness. The residue was subjected to preparative thin layer chromatography, which was developed with a mixture of chloroform and methanol (1:1, v/v) to afford 11-acetyl-4-formyl-9-hydroxy-6-methoxy-14-oxa-1,11-diazatetracyclo[7.4.1.0$^{2,7}$.0$^{10,12}$]tetradeca-2,4,6-trien-8-ylmethyl carbamate (11 mg).

$^1$H NMR δ(ppm, CDCl$_3$): 9.95 (1H, s), 7.23 (1H, s), 6.93 (1H, s), 5.08 (1H, d d, J=1.4, 13 Hz), 4.79 (2H, s like), 4.58 (1H, d d, J=4.1, 13 Hz), 3.99 (1H, d d, J=2.3, 14.9 Hz), 3.96 (3H, s), 3.67 (1H, d, J=14.9 Hz), 3.28 (1H, dd, J=1.4, 4.1 Hz), 3.22 (1H, d, J=6.3 Hz), 2.80 (1H, d d, J=2.3, 6.3 Hz), 1.88 (3H, s)

IR $\nu_{max}^{CHCl_3}$: 3540, 3430, 1695 cm$^{-1}$

EI Mass: m/z 377 (M$^+$)

Further, 11-acetyl-4-formyl-6,9-dimethoxy-14-oxa-1,11-diazatetracyclo[7.4.1.0$^{2,7}$.0$^{10,12}$]tetradeca-2,4,6-trien-8-ylmethyl carbamate (20 mg) was afforded from the same preparative thin layer chromatography.

$^1$H NMR δ (ppm, CDCl$_3$): 9.93 (1H, s), 7.13 (1H, s), 6.91 (1H, s), 4.66 (1H, d d, J=6.3, 11.3 Hz), 4.64 (2H, s), 4.31 (1H, d d, J=2.7, 11.3 Hz), 3.93 (3H, s), 3.66 (3H, s), 3.44 (1H, d d, J=2.7, 6.3 Hz), 3.25 (1H, d, J=6.3 Hz), 2.86 (1H, d d, J=2.3, 6.3 Hz), 1.87 (3H, s)

IR $\nu_{max}^{CHCl_3}$: 3550, 3435, 1720, 1705, 1695 cm$^{-1}$

EI Mass: 391 (M$^+$)

EXAMPLE 24

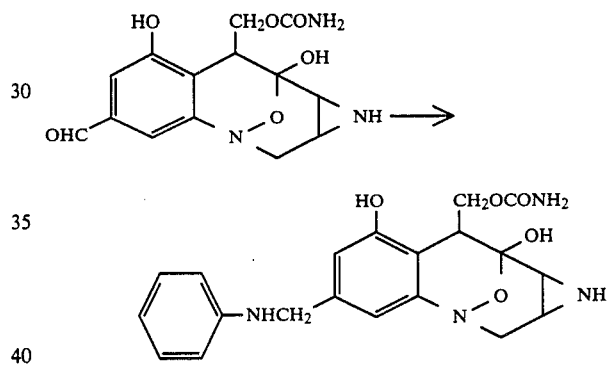

4-Formyl-6,9-dihydroxy-14-oxa-1,11-diazatetracyclo[7.4.1.0$^{2,7}$.0$^{10,12}$]-tetradeca-2,4,6-trien-8-ylmethyl carbamate (50 mg) was dissolved in methanol (5 ml). Aniline (0.05 ml) was added to this solution and the mixture was allowed to stand at room temperature for 3 hours to give a solution containing 6,9-dihydroxy-4-phenyliminomethyl-14-oxa-1,11-diazatetracyclo[7.4.1.0$^{2,7}$.0$^{10,12}$]tetradeca-2,4,6-trien-8-ylmethyl carbamate. 10% Palladium on carbon (100 mg) was added to the solution, and the mixture was stirred for 2 hours at room temperature under hydrogen atmosphere (4.5 atm). The mixture was filtered through cellulose powder and the filter cake was washed with methanol (20 ml). The filtrate and the washings were combined and evaporated in vacuo. The residue was subjected to preparative thin layer chromatography, which was developed with a mixture of chloroform, methanol and water (65:25:4, v/v/v) to afford 4-anilinomethyl-6,9-dihydroxy-14-oxa-1,11-diazatetracyclo[7.4.1.0$^{2,7}$.0$^{10,12}$]tetradeca-2,4,6-trien-8-ylmethyl carbamate (25 mg).

$^1$H NMR δ (ppm, CD$_3$OD): 7.0–7.2 (2H), 6.3–6.7 (5H), 5.2–4.4 (3H, m), 4.18 (2H, s), 3.9–3.2 (3H, m), 2.6 (1H, m)

IR $\nu_{max}^{KBr}$: 3200, 1673 cm$^{-1}$

SI Mass: m/z 399 (M$^+$+1), 421 (M$^+$+23)

EXAMPLE 25

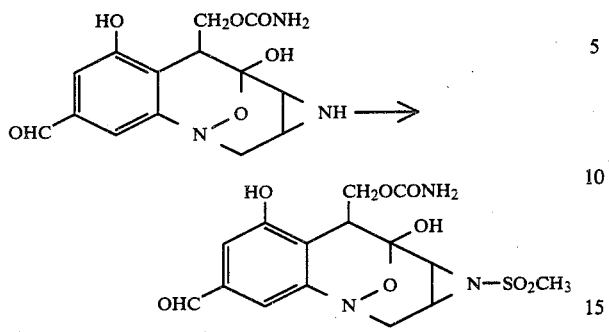

4-Formyl-6,9-dihydroxy-14-oxa-1,11-diazatetracyclo[7.4.1.0$^{2,7}$.0$^{10,12}$]tetradeca-2,4,6-trien-8-ylmethyl carbamate (50 mg) was dissolved in pyridine (1.19 ml) containing mesyl chloride (12 μl). The solution was stirred for 1 hour in a dry ice-carbon tetrachloride bath under nitrogen atmosphere. The solution was evaporated in vacuo and the residue was subjected to preparative thin layer chromatography. Development was carried out with a mixture of chloroform and methanol to afford 4-formyl-6,9-dihydroxy-11-mesyl-14-oxa-1,11-diazatetracyclo[7.4.1.0$^{2,7}$.0$^{10,12}$]tetradeca-2,4,6-trien-8-ylmethyl carbamate (47 mg).

$^1$H NMRδ (ppm, pyridine-d$_5$): 10.65(s) } (1H), 3.00(s) } (3H)
10.00(s) 3.57(s)

IR $\nu_{max}^{KBr}$: 3200(broad), 1660, 1574 cm$^{-1}$
SI Mass: m/z 400 (M$^+$+1)

EXAMPLE 26

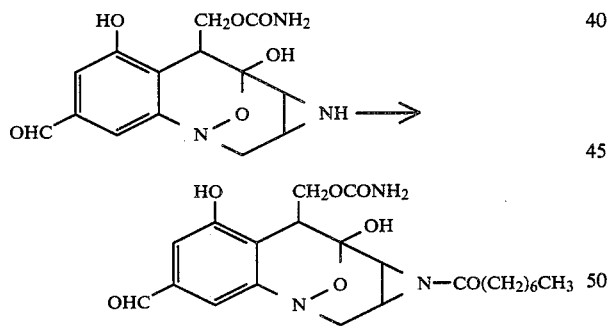

4-Formyl-6,9-dihydroxy-14-oxa-1,11-diazatetracyclo[7.4.1.0$^{2,7}$.0$^{10,12}$]tetradeca-2,4,6-trien-8-ylmethyl carbamate (32 mg) was dissolved in a mixture of N,N-dimethylformamide (1.0 ml) and pyridine (1.0 ml). To the solution was added octanoyl chloride (17 μl) with stirring under nitrogen atmosphere in an ice-water bath. The mixture was stirred for 2 hours under nitrogen atmosphere in an ice-water bath and evaporated in vacuo. The residue was subjected to preparative thin layer chromatography and development was carried out with a mixture of chloroform and methanol to afford 4-formyl-6,9-dihydroxy-11-octanoyl-14-oxa-1,11-diazatetracyclo[7.4.1.0$^{2,7}$.0$^{10,12}$]tetradeca-2,4,6-trien-8-ylmethyl carbamate (33 mg).
IR $\nu_{max}^{KBr}$: 1715, 1688, 1650, 1580, 1345 cm$^{-1}$
SI Mass: m/z 448 (M$^+$+1)

EXAMPLE 27

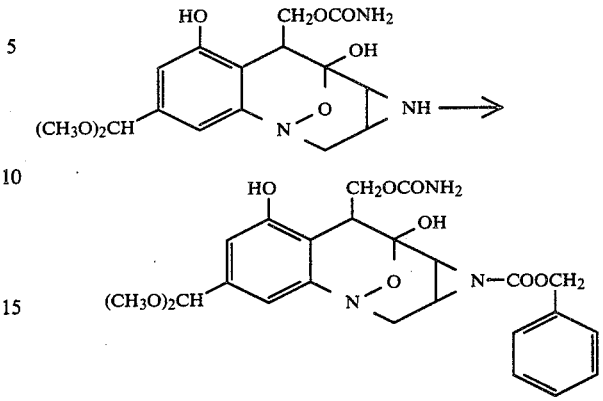

6,9-Dihydroxy-4-dimethoxymethyl-14-oxa-1,11-diazatetracyclo[7.4.1.0$^{2,7}$.0$^{10,12}$]tetradeca-2,4,6-trien-8-ylmethyl carbamate (22 mg) and sodium bicarbonate (12 mg) were dissolved in water (0.5 ml). To the solution was added benzyl chloroformate (0.02 ml) with stirring in an ice-water bath. The mixture was stirred for 30 minutes in an ice-water bath and subjected to preparative thin layer chromatography. Development was carried out with a mixture of chloroform and methanol to afford 11-benzyloxycarbonyl-6,9-dihydroxy-4-dimethoxymethyl-14-oxa-1,11-diazatetracyclo[7.4.1.0$^{2,7}$.0$^{10,12}$]tetradeca-2,4,6-trien-8-ylmethyl carbamate (15 mg).

$^1$H NMRδ (ppm, CDCl$_3$):7.39 (5H, s), 6.63 (1H, s),
6.50(s) } (1H), 3.32(s) } (6H)
6.42(s) 3.26(s)

IR $\nu_{max}^{CHCl_3}$: 3520, 3340, 1717, 1589, 1350 cm$^{-1}$

EI Mass: m/z 501 (M$^+$)

IR $\nu_{max}^{CHCl_3}$: 3520, 3340, 1717, 1589, 1350 cm$^{-1}$
EI Mass: m/z 501 (M$^+$)

EXAMPLE 28

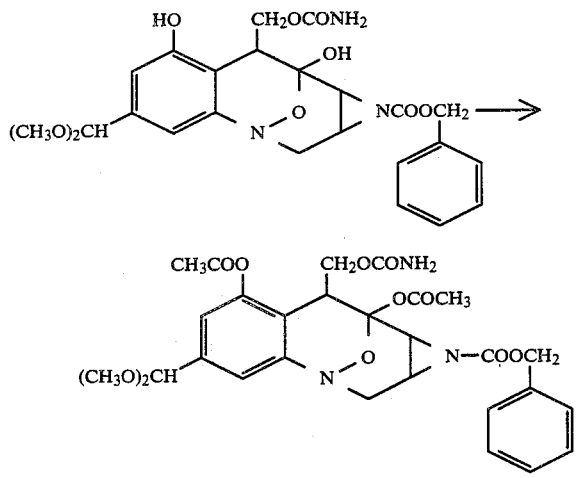

11-Benzyloxycarbonyl-6,9-dihydroxy-4-dimethoxymethyl-14-oxa-1,11-diazatetracyclo[7.4.1.0$^{2,7}$.0$^{10,12-}$ ]tetradeca-2,4,6-trien-8-ylmethyl carbamate (15 mg) was dissolved in a mixture of pyridine (1.0 ml) and acetic anhydride (0.5 ml). The solution was stirred for 1 day at room temperature. To the solution was added 4-dimethylaminopyridine (catalytic amount) and the mixture was stirred for 12 hours at room temperature. The reaction mixture was evaporated in vacuo, and the residue was subjected to preparative thin layer chromatography. Development was carried out with a mixture of chloroform and methanol to afford 11-benzyloxycarbonyl-8-carbamoyloxymethyl-4-dimethoxymethyl-14-oxa-1,11-diazatetracyclo[7.4.1.0$^{2,7}$.0$^{10,12}$]tetradeca-2,4,6-trien-6,9-diyl diacetate (17 mg).

IR $\nu_{max}^{CHCl_3}$: 3525, 3430, 1762, 1723, 1583 cm$^{-1}$
SI Mass: m/z 586 (M$^+$+1)

EXAMPLE 29

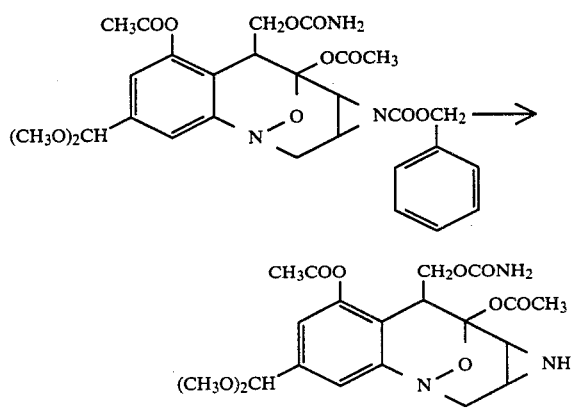

11-Benzyloxycarbonyl-8-carbamoyloxymethyl-4-dimethoxymethyl-14-oxa-1,11-diazatetracyclo[7.4.1.0$^{2,7}$.0$^{10,12}$]tetradeca-2,4,6-trien-6,9-diyl diacetate (270 mg) was dissolved in methanol (10 ml). To the solution was added 10% palladium on carbon (300 mg) and the mixture was stirred for 1 hour under hydrogen atmosphere (20 psi) at room temperature. The reaction mixture was filtered through cellulose powder and the filtrate was evaporated in vacuo. The residue was subjected to preparative thin layer chromatography and development was carried out with a mixture of chloroform and methanol to afford 8-carbamoyloxymethyl-4-dimethoxymethyl-14-oxa-1,11-diazatetracyclo[7.4.1.0$^{2,7}$.0$^{10,12}$]tetradeca-2,4,6-trien-6,9-diyl diacetate (80 mg).

$^1$H NMR δ(ppm, CDCl$_3$): 6.95 (1H, s), 6.77 (1H, s), 5.37 (1H, s), 4.63 (2H, broad s), 4.34 (2H, d, J=6 Hz), 3.99 (1H, dd, J=3, 15 Hz), 3.83 (1H, t, J=6 Hz), 3.61 (1H, d, J=15 Hz), 3.30 (6H, s), 2.35 (3H, s), 2.22 (3H, s)
IR $\nu_{max}^{CHCl_3}$: 3540, 3440, 1740, 1585, 1370, 1335 cm$^{-1}$
SI Mass: m/z 452 (M$^+$+1)

EXAMPLE 30

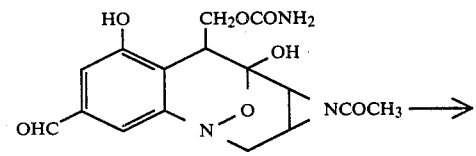

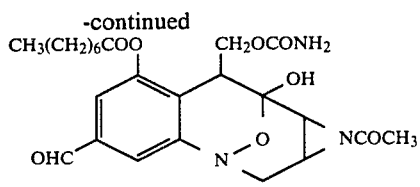

11-Acetyl-4-formyl-6,9-dihydroxy-14-oxa-1,11-diazatetracyclo[7.4.1.0$^{2,7}$.0$^{10,12}$]tetradeca-2,4,6-trien-8-ylmethyl carbamate (25 mg) was dissolved in tetrahydrofuran (2.5 ml) and the solution was added to a suspension of sodium hydride (60% in oil, 3 mg) in tetrahydrofuran (0.5 ml). To this mixture was added a solution of octanoyl chloride (12 μl) in tetrahydrofuran (108 μl) in an ice-water bath and the mixture was stirred for 1 hour in an ice-water bath. After stirring for 36 hours at room temperature, an additional amount of octanoyl chloride (50 μl) was added and the mixture was stirred for 3 hours at room temperature. The reaction mixture was then directly subjected to a preparative thin layer chromatography. Development was carried out with a mixture of chloroform and acetone (1:1, v/v) to afford 11-acetyl-8-carbamoyloxymethyl-4-formyl-9-hydroxy-14-oxa-1,11-diazatetracyclo[7.4.1.0$^{2,7}$.0$^{10,12}$]tetradeca-2,4,6-trien-6-yl octanoate (7 mg).

| $^1$H NMRδ (ppm, CDCl$_3$): 9.90(s) | (1H) | 7.36(s) | (2H) |
|---|---|---|---|
| 9.84(s) | | 7.14(s) | |
| | | 7.01(s) | |
| | | 6.83(s) | |

IR $\nu_{max}^{CHCl_3}$: 3550, 3440, 3250, 2940, 1750, 1720, 1700, 1580 cm$^{-1}$
SI Mass: m/z 490 (M$^+$+1)

EXAMPLE 31

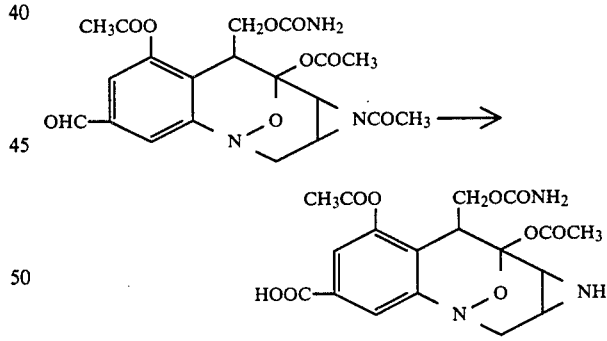

To a solution of 11-acetyl-8-carbamoyloxymethyl-4-formyl-14-oxa-1,11-diazatetracyclo[7.4.1.0$^{2,7}$.0$^{10,12}$]tetradeca-2,4,6-trien-6,9-diyl diacetate (29 mg) in acetone (2 ml) was added a mixture of chromium trioxide (26 mg), water (76 μl) and sulfuric acid (22 μl) in an ice-water bath. After stirring for 30 minutes in an ice-water bath, isopropyl alcohol (2 ml) was added to the reaction mixture. The resultant mixture was then poured into water (10 ml) and extracted with a mixture of chloroform and methanol (2:1, v/v) (10 ml×5). The extracts were combined and dried over magnesium sulfate, and then evaporated in vacuo. The residue was subjected to preparative thin layer chromatography, which was developed with a mixture of chloroform, methanol and water (65:25:4, v/v) to afford 6,9-diacetoxy-8-carbamoyloxymethyl-14-oxa-1,11-diazatetracyclo[7.4.1.0²,⁷.0¹⁰,¹²]tetradeca-2,4,6-triene-4-carboxylic acid (5 mg).

¹H NMR δ (ppm, CD₃OD): 7.34 (1H, s), 7.19 (1H, s), 4.25 (1H, dd, J=8.1, 11.7 Hz), 4.1-3.5 (4H), 2.95 (1H, d, J=7.2 Hz), 2.30 (3H, s), 2.13 (3H, s)

IR ν$_{max}^{KBr}$: 3300, 2910, 1740, 1720, 1688 cm⁻¹

SI Mass: m/z 444 (M⁺+23), 422 (M⁺+1)

EXAMPLE 32

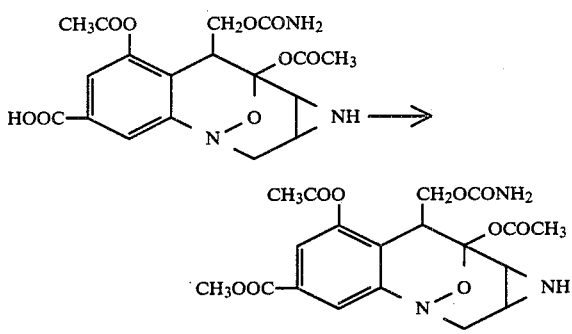

To a solution of 6,9-diacetoxy-8-carbamoyloxymethyl-14-oxa-1,11-diazatetracyclo[7.4.1.0²,⁷.0¹⁰,¹²]tetradeca-2,4-6-triene-4-carboxylic acid (12 mg) in methanol (2 ml) was added a solution of diazomethane (excess) in diethyl ether at room temperature. The mixture was allowed to stand at room temperature for 20 minutes and then evaporated to dryness in vacuo. The residue was subjected to preparative thin layer chromatography, which was developed with a mixture of chloroform and methanol (15:1 v/v) to afford methyl 6,9-diacetoxy-8-carbamoyloxymethyl-14-oxa-1,11-diazatetracyclo[7.4.1.0²,⁷.0¹⁰,¹²]tetradeca-2,4,6-triene-4-carboxylate (5 mg).

¹H NMR δ (ppm, CDCl₃): 7.47 (1H, s), 7.30 (1H, s), 4.62 (2H, broad s), 4.32 (2H, d, J=5.4 Hz), 3.86 (3H, s), 2.37 (3H, s), 2.20 (3H, s)

EXAMPLE 33

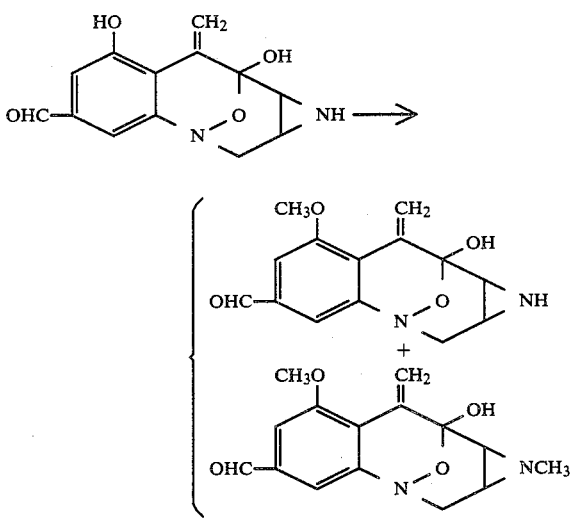

To a solution of 6,9-dihydroxy-8-methylene-14-oxa-1,11-diazatetracyclo[7.4.1.0²,⁷.0¹⁰,¹²]tetradeca-2,4,6-triene-4-carbaldehyde (30 mg) in dimethylformamide (1.0 ml) was added a suspension of sodium hydride (60% in oil, 4.6 mg) in dimethylformamide (0.5 ml) in an ice-water bath. To this mixture was added a solution of methyl iodide (7.2 μl) in dimethylformamide (0.1 ml) in an ice-water bath. After stirring for 1 hour in an ice-water bath, the reaction mixture was evaporated to dryness in vacuo, and the residue was subjected to preparative thin layer chromatography, which was developed with a mixture of chloroform and methanol (8:1, v/v) to afford 9-hydroxy-6-methoxy-8-methylene-14-oxa-1,11-diazatetracyclo[7.4.1.0²,⁷.0¹⁰,¹²]tetradeca-2,4,6-triene-4-carbaldehyde (19 mg).

¹H NMR δ (ppm, CDCl₃): 9.90 (1H, s), 7.13 (1H, d, J=2 Hz), 6.97 (1H, d, J=2 Hz), 6.63 (1H, d, J=2 Hz), 6.17 (1H, d, J=2 Hz), 3.97 (3H, s), 3.89 (1H, dd, J=2, 14.9 Hz), 3.58 (1H, dd, J=4.5, 14.9 Hz), 2.3-3.0 (4H)

IR ν$_{max}^{KBr}$: 3400, 2915, 1680, 1560, 1378 cm⁻¹

SI Mass: m/z 275 (M⁺+1)

Further, 6-methoxy-11-methyl-8-methylene-14-oxa-1,11-diazatetracyclo[7.4.1.0²,⁷.0¹⁰,¹²]tetradeca-2,4,6-triene-4-carbaldehyde (2 mg) could be afforded from the same preparative thin layer chromatography.

¹H NMR δ (ppm, CDCl₃): 9.89 (1H, s), 7.12 (1H, d, J=1.4 Hz), 6.96 (1H, d, J=1.4 Hz), 6.61 (1H, d, J=1.4 Hz), 6.16 (1H, d, J=1.4 Hz), 3.99 (3H, s), 3.83 (1H, dd, J=1.9, 15 Hz), 3.64 (1H, dd, J=6.2, 15 Hz), 2.43 (3H, s), 1.89 (1H, ddd, J=1.9, 6.2, 6.8 Hz), 1.79 (1H, d, J=6.8 Hz)

EXAMPLE 34

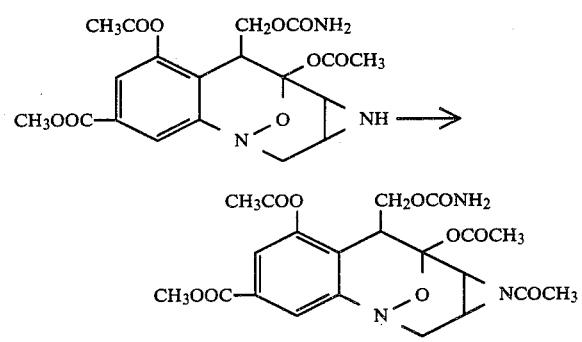

To a solution of methyl 6,9-diacetoxy-8-carbamoyloxymethyl-14-oxa-1,11-diazatetracyclo[7.4.1.0²,⁷.0¹⁰,¹²]tetradeca-2,4,6-triene-4-carboxylate (5 mg) in pyridine (1.0 ml) was added acetic anhydride (0.5 ml), and the solution was stirred for 5 hours at room temperature. The reaction mixture was evaporated to dryness in vacuo and the residue was subjected to preparative thin layer chromatography, which was developed with a mixture of chloroform and methanol (30:1 v/v) to afford methyl 6,9-diacetoxy-11-acetyl-8-carbamoyloxymethyl-14-oxa-1,11-diazatetracyclo[7.4.1.0²,⁷.0¹⁰,¹²]tetradeca-2,4,6-triene-4-carboxylate (5 mg).

¹H NMR δ (ppm, CDCl₃): 7.44 (1H, d, J=1.1 Hz), 7.31 (1H, d, J=1.1 Hz), 4.63 (2H, broad s), 4.39 (1H, dd, J=7.0, 11.9 Hz), 4.33 (1H, dd, J=4.3, 11.9 Hz), 4.04 (1H, dd, J=2.4, 14.9 Hz), 3.89 (3H, s), 3.86 (1H, dd, J=4.3, 7.0 Hz), 3.74 (1H, d, J=14.9 Hz), 3.40 (1H, d, J=6.8 Hz), 2.82 (1H, dd, J=2.4, 6.8 Hz), 2.38 (3H, s), 2.24 (3H, s), 1.97 (3H, s)

IR ν$_{max}^{CHCl_3}$: 3525, 3420, 1761, 1734, 1721, 1715, 1580 cm⁻¹

SI Mass: m/z 478 (M⁺+1)

EXAMPLE 35

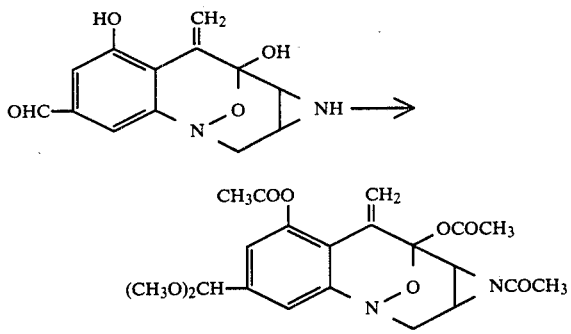

To a solution of 6,9-dihydroxy-8-methylene-14-oxa-1,11-diazatetracyclo[7.4.1.0$^{2,7}$.0$^{10,12}$]tetradeca-2,4,6-triene-4-carbaldehyde (151 mg) in methanol (15 ml) was added 6% solution of hydrogen chloride in methanol (0.5 ml). The mixture was stirred for 1 hour at ambient temperature and evaporated to dryness in vacuo to afford a crude product of 4-dimethoxymethyl-8-methylene-14-oxa-1,11-diaza-tetracyclo[7.4.1.0$^{2,7}$.0$^{10,12}$]tetradeca-2,4,6-triene-6,9-diol (286 mg). This crude product (260 mg) was dissolved in a mixture of pyridine (5.0 ml) and acetic anhydride (2.5 ml). To this solution was added 4-dimethylaminopyridine (25 mg) and the mixture was stirred for 2 days at ambient temperature, and then evaporated in vacuo. The residue was subjected to preparative thin layer chromatography, which was developed with a mixture of chloroform and acetone (15:1 v/v) to afford A-isomer of 11-acetyl-4-dimethoxymethyl-8-methylene-14-oxa-1,11-diazatetracyclo[7.4.1.0$^{2,7}$.0$^{10,12}$]tetradeca-2,4,6-trien-6,9-diyl diacetate (100 mg).

$^1$H NMR δ (ppm, CDCl$_3$): 6.82 (1H, s), 6.77 (1H, s), 6.17 (1H, s), 5.78 (1H, s), 5.35 (1H, s), 4.08 (1H, dd, J=2.7, 14.9 Hz), 3.72 (1H, d, J=14.9 Hz), 3.35 (1H, d, J=6.3 Hz), 3.29 (6H, s), 2.99 (1H, dd, J=2.7, 6.3 Hz), 2.34 (3H, s), 2.24 (3H, s), 1.87 (3H, s)

SI Mass: m/z 433 (M$^+$+1)

Further, B-isomer of 11-acetyl-4-dimethoxymethyl-8-methylene-14-oxa-1,11-diazatetracyclo[7.4.1.0$^{2,7}$.0$^{10,12}$]tetradeca-2,4,6-trien-6,9-diyl diacetate (100 mg) could be afforded from the same preparative thin layer chromatography.

$^1$H NMR δ (ppm, CDCl$_3$): 6.96 (1H, d, J=2 Hz), 6.90 (1H, d, J=2 Hz), 6.18 (1H, s), 5.53 (1H, s), 5.34 (1H, s), 3.97 (1H, dd, J=2.7, 14.4 Hz), 3.60 (1H, dd, J=5.4, 14.4 Hz), 3.30 (6H, s), 2.90–3.15 (2H), 2.32 (3H, s), 2.25 (3H, s), 2.22 (3H, s)

SI Mass: m/z 433 (M$^+$+1)

EXAMPLE 36

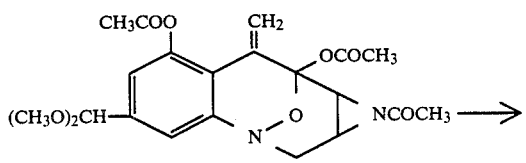

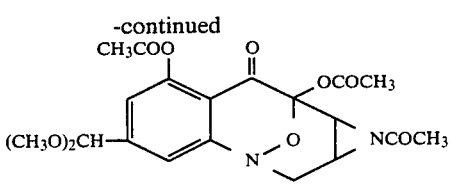

B-Isomer of 11-acetyl-4-dimethoxymethyl-8-methylene-14-oxa-1,11-diazatetracyclo[7.4.1.0$^{2,7}$.0$^{10,12}$]tetradeca-2,4,6-trien-6,9-diyl diacetate (12 mg) was dissolved in dichloromethane (10 ml), and ozone was bubbled for 30 minutes in a dry ice-carbon tetrachloride bath and then nitrogen was passed for 3 minutes. To the mixture was added dimethylsulfide (0.5 ml) in a dry ice-carbon tetrachloride bath under nitrogen atmosphere and the resultant mixture was stirred for 10 minutes. After allowing to stand for 15 minutes at ambient temperature, the mixture was evaporated in vacuo, and the residue was subjected to preparative thin layer chromatography, which was developed with a mixture of n-hexane and ethyl acetate (1:2, v/v) to afford B-isomer of 11-acetyl-4-dimethoxymethyl-8-oxo-14-oxa-1,11-diazatetracyclo[7.4.1.0$^{2,7}$.0$^{10,12}$]tetradeca-2,4,6-trien-6,9-diyl diacetate (2 mg).

$^1$H NMR δ (ppm, CDCl$_3$): 6.971 (1H, d, J=1.6 Hz), 6.969 (1H, d, J=1.6 Hz), 5.35 (1H, s), 4.05 (1H, dd, J=1.4, 14.6 Hz), 3.65 (1H, dd, J=6.2, 14.6 Hz), 3.33 (3H, s), 3.32 (3H, s), 3.35–3.29 (1H), 3.16 (1H, dt, J=1.4, 6.2 Hz), 2.38 (3H, s), 2.26 (3H, s), 2.22 (3H, s)

IR $\nu_{max}^{KBr}$: 2890, 1750, 1732, 1711, 1688 cm$^{-1}$

SI Mass: m/z 435 (M$^+$+1)

EXAMPLE 37

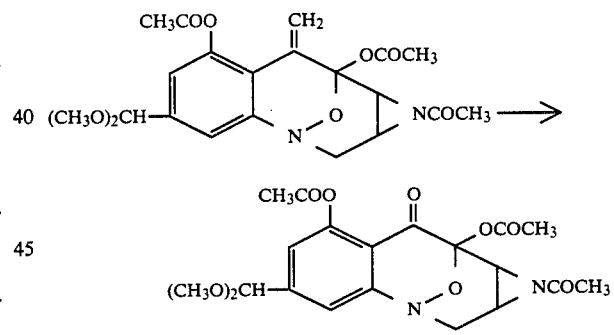

A-Isomer of 11-acetyl-4-dimethoxymethyl-8-methylene-14-oxa-1,11-diazatetracyclo[7.4.1.0$^{2,7}$.0$^{10,12}$]tetradeca-2,4,6-trien-6,9-diyl diacetate (45 mg) was dissolved in dichloromethane (15 ml), and ozone was bubbled for 10 minutes in a dry ice-carbon tetrachloride bath and then nitrogen was passed for 3 minutes. To the mixture was added dimethyl sulfide (0.5 ml) in a dry ice-carbon tetrachloride bath under nitrogen atmosphere. The mixture was allowed to stand for 20 minutes at ambient temperature and evaporated in vacuo. The residue was subjected to preparative thin layer chromatography, which was developed with a mixture of n-hexane and ethyl acetate (1:2, v/v) to afford A-isomer of 11-acetyl-4-dimethoxymethyl-8-oxo-14-oxa-1,11-diazatetracyclo[7.4.1.0$^{2,7}$.0$^{10,12}$]tetradeca-2,4,6-trien-6,9-diyl diacetate (34 mg).

$^1$H NMR δ (ppm, CDCl$_3$): 6.86 (1H, d, J=0.8 Hz), 6.84 (1H, d, J=0.8 Hz), 5.35 (1H, s), 4.10 (1H, dd, J=2.7, 14.6 Hz), 3.75 (1H, d, J=14.6 Hz), 3.31 (3H, s), 3.29

(3H, s), 3.23 (1H, d, J=6.2 Hz), 3.04 (1H, dd, J=1.9, 6.2 Hz), 2.36 (3H, s), 2.23 (3H, s), 1.94 (3H, s)

IR $\nu_{max}^{CHCl_3}$: 3000, 2930, 1772, 1717, 1703, 1618 cm$^{-1}$

SI Mass: m/z 435 (M$^+$+1)

EXAMPLE 38

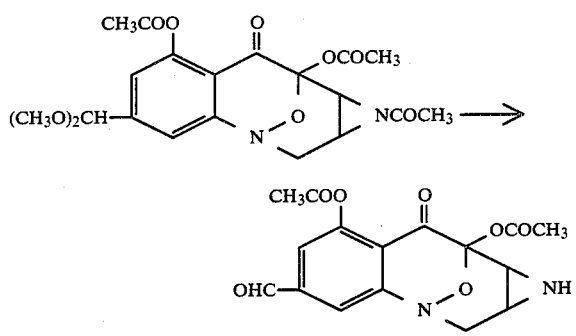

To a solution of A-isomer of 11-acetyl-4-dimethoxymethyl-8-oxo-14-oxa-1,11-diazatetracyclo[7.4.1.0$^{2,7}$.0$^{10,12}$]tetradeca-2,4,6-trien-6,9-diyl diacetate (6 mg) in acetone (0.5 ml) was added p-toluene sulfonic acid (1 mg). The mixture was stirred for 1 hour at ambient temperature, and then subjected to preparative thin layer chromatography, which was developed with a mixture of chloroform and acetone (5:1, v/v) to afford A-isomer of 4-formyl-8-oxo-14-oxa-1,11-diazatetracyclo[7.4.1.0$^{2,7}$.0$^{10,12}$]tetradeca-2,4,6-trien-6,9-diyl diacetate (1 mg).

$^1$H NMR δ (ppm, CDCl$_3$): 7.20 (1H, d, J=1.4 Hz), 7.05 (1H, d, J=1.4 Hz), 3.77 (1H, dd, J=2.7, 13.5 Hz), 2.94 (1H, d, J=13.5 Hz), 2.38 (3H, s), 2.26 (1H, d, J=6.8 Hz), 2.15–2.20 (1H), 2.17 (3H, s)

IR $\nu_{max}^{KBr}$: 3380, 1753, 1715, 1692, 1607 cm$^{-1}$

SI Mass: m/z 369 (M$^+$+23)

EXAMPLE 39

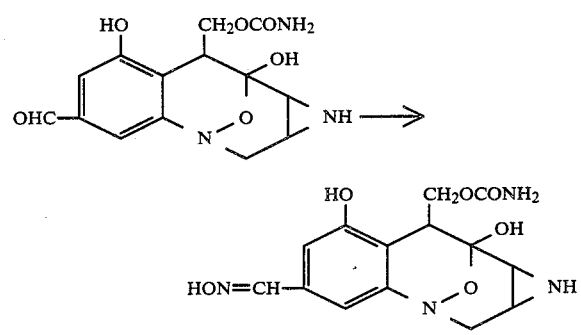

To a solution of 4-formyl-6,9-dihydroxy-14-oxa-1,11-diazatetracyclo[7.4.1.0$^{2,7}$.0$^{10,12}$]tetradeca-2,4,6-trien-8-ylmethyl carbamate (100 mg) in methanol (5 ml) were added hydroxylamine hydrochloride (90 mg) and sodium bicarbonate (106 mg). The mixture was stirred for 1 hour at ambient temperature and evaporated in vacuo. The residue was subjected to preparative thin layer chromatography, which was developed with a mixture of chloroform, methanol and water (6:4:1, v/v) to afford 6,9-dihydroxy-4-hydroxyiminomethyl-14-oxa-1,11-diazatetracyclo[7.4.1.0$^{2,7}$.0$^{10,12}$]tetradeca-2,4,6-trien-8-ylmethyl carbamate (105 mg).

$^1$H NMR δ (ppm, CD$_3$OD): 7.94 (1H, s), 6.78 (1H, s),

| 6.55(s) 6.48(s) } | (1H), 5.0–5.4(1H), 4.4–4.9 (2H), 3.6–3.9 (2H), 2.2–2.9 (2H) |

IR $\nu_{max}^{KBr}$: 3150, 1677, 1604, 1330 cm$^{-1}$

SI Mass: m/z 337 (M$^+$+1), 359 (M$^+$+23)

EXAMPLE 40

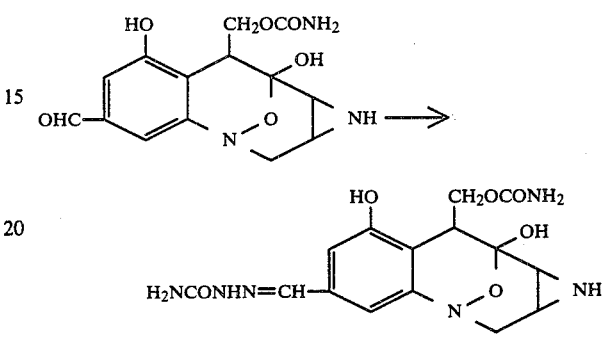

To a solution of 4-formyl-6,9-dihydroxy-14-oxa-1,11-diazatetracyclo[7.4.1.0$^{2,7}$.0$^{10,12}$]tetradeca-2,4,6-trien-8-ylmethyl carbamate (50 mg) in methanol (5 ml) were added sodium bicarbonate (27 mg) and semicarbazide hydrochloride (35 mg). The mixture was stirred for 1 hour at ambient temperature and evaporated in vacuo. The residue was subjected to preparative thin layer chromatography, which was developed with a mixture of chloroform, methanol and water (6:4:1, v/v) to afford 6,9-dihydroxy-4-semicarbazonomethyl-14-oxa-1,11-diazatetracyclo[7.4.1.0$^{2,7}$.0$^{10,12}$]tetradeca-2,4,6-trien-8-ylmethyl carbamate (59 mg).

| $^1$H NMRδ (ppm, CD$_3$OD): 7.74 (1H, s), 6.84 (1H, s), 6.69(s) 6.60(s) } (1H), 5.0–5.3 (1H), 4.3–4.6 (2H), 3.5–3.9 (2H), 2.3–2.8 (2H) |

IR $\nu_{max}^{KBr}$: 3300, 1655, 1578 cm$^{-1}$

SI Mass: m/z 379 (M$^+$+1)

EXAMPLE 41

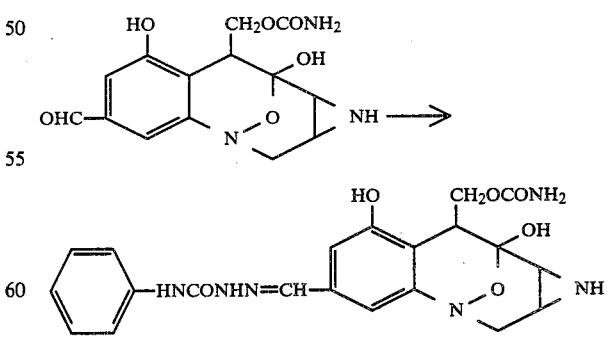

To a solution of 4-formyl-6,9-dihydroxy-14-oxa-1,11-diazatetracyclo[7.4.1.0$^{2,7}$.0$^{10,12}$]tetradeca-2,4,6-trien-8-ylmethyl carbamate (50 mg) in methanol (5 ml) were added sodium bicarbonate (27 mg) and 4-phenylsemicarbazide hydrochloride (59 mg). The mixture was stirred for 1 hour at ambient temperature and evaporated in vacuo. The residue was subjected to preparative thin layer chromatography, which was developed with a mixture of chloroform and methanol (3:1, v/v) to afford 6,9-dihydroxy-4-(4-phenylsemicarbazonomethyl)-14-oxa-1,11-diazatetracyclo[7.4.1.0$^{2,7}$.0$^{10,12}$]tetradeca-2,4,6-trien-8-ylmethyl carbamate (64 mg).

$^1$H NMRδ (ppm, CD$_3$OD): 7.87(s), 7.77(s) (1H),
7.0–7.6 (5H), 6.93(d), 6.87(d) (1H, J= 1Hz),
6.74(d), 6.66(d) (1H, J=1Hz), 5.0–5.3 (1H),
4.4–4.8 (2H), 3.5–3.8 (2H), 2.4–2.8 (2H)

IR ν$_{max}$$^{KBr}$: 3250, 1654, 1591, 1520 cm$^{-1}$
SI Mass: m/z 455 (M$^+$+1)

EXAMPLE 42

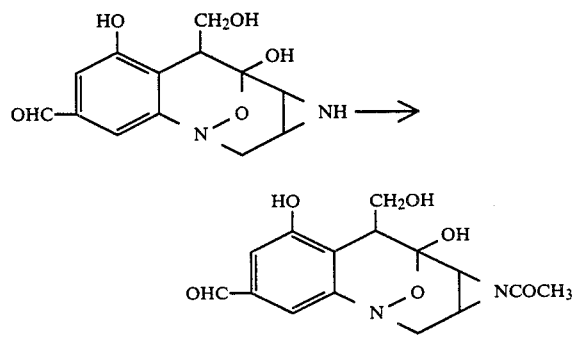

To a solution of 6,9-dihydroxy-8-hydroxymethyl-14-oxa-1,11-diazatetracyclo[7.4.1.0$^{2,7}$.0$^{10,12}$]tetradeca-2,4,6-triene-4-carbaldehyde (98 mg) in methanol (3 ml) was added acetic anhydride (40 μl). The mixture was stirred for 1 hour at ambient temperature and evaporated in vacuo. The residue was subjected to preparative thin layer chromotography, which was developed with a mixture of chloroform and methanol (10:1, v/v) to afford 11-acetyl-6,9-dihydroxy-8-hydroxymethyl-14-oxa-1,11-diazatetracyclo[7.4.1.0$^{2,7}$.0$^{10,12}$]tetradeca-2,4,6-triene-4-carbaldehyde (71 mg).

$^1$H NMRδ (ppm, CD$_3$OD): 9.81(s), 9.77(s) (1H),
6.98(d), 6.93(d) (1H, J=2Hz), 6.89(d), 6.81(d) (1H, J=2Hz),
4.5–4.8 (1H), 3.6–4.3 (4H), 2.8–3.5 (2H),
1.84(s), 2.18(s) (3H)

IR ν$_{max}$$^{KBr}$: 3150, 1635, 1578 cm$^{-1}$
SI Mass: m/z 321 (M$^+$+1)

EXAMPLE 43

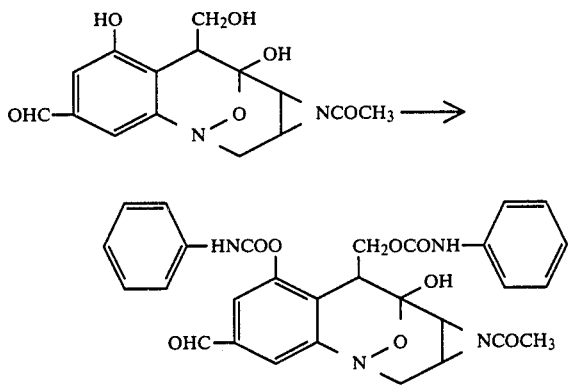

To a solution of 11-acetyl-6,9-dihydroxy-8-hydroxymethyl-14-oxa-1,11-diazatetracyclo[7.4.1.0$^{2,7}$.0$^{10,12}$]tetradeca-2,4,6-triene-4-carbaldehyde (18 mg) in dimethylformamide (1.0 ml) was added a mixture of phenyl isocyanate (12.5 μl) in dimethylformamide (1.25 ml) in an ice-water bath. The mixture was stirred for 30 minutes in an ice-water bath and then stirred for additional 1 hour at ambient temperature. The mixture was evaporated in vacuo and subjected to preparative thin layer chromatography, which was developed with a mixture of chloroform and methanol (15:1, v/v) to afford 11-acetyl-4-formyl-9-hydroxy-6-(N-phenylcarbamoyloxy)-14-oxa-1,11-diazatetracyclo[7.4.1.0$^{2,7}$.0$^{10,12}$]tetradeca-2,4,6-trien-8-ylmethyl N-phenyl-carbamate (12 mg).

$^1$H NMRδ (ppm, CDCl$_3$): 9.91 (1H, s), 7.9–8.2 (1H),
6.65–7.65 (11H), 5.90–6.00 (1H), 5.21 (1H, broad s), 3.5–4.9 (4H), 2.7–3.5 (3H),
2.23(s), 1.87(s) (3H)

IR ν$_{max}$$^{CHCl_3}$: 3435, 3320, 1755, 1720, 1700, 1602, 1531 cm$^{-1}$
SI Mass: m/z 559 (M$^+$+1)

EXAMPLE 44

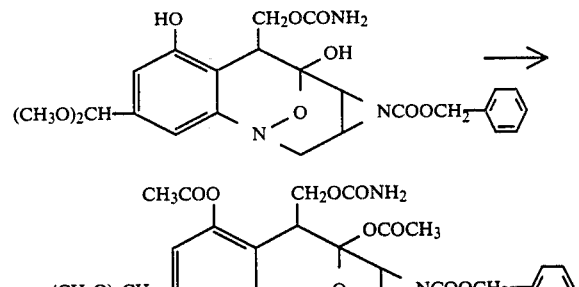

To a solution of 11-benzyloxycarbonyl-6,9-dihydroxy-4-dimethoxymethyl-14-oxa-1,11-diazatetracyclo[7.4.1.0$^{2,7}$.0$^{10,12}$]tetradeca-2,4,6-trien-8-ylmethyl carbamate (400 mg) in a mixture of pyridine (10 ml) and acetic anhydride (5 ml) was added 4-dimethylaminopyridine (10 mg). The mixture was stirred overnight at ambient temperature and evaporated in vacuo. The residue was subjected to silica gel column chromatography and elution was carried out with a mixture of chloroform and methanol (50:1, v/v). The desired fractions were combined and then evaporated to dryness in vacuo to afford 11-benzyloxycarbonyl-8-carbamoyloxymethyl-4-dimethoxymethyl-14-oxa-1,11-diazatetracyclo[7.4.1.0$^{2,7}$.0$^{10,12}$]tetradeca-2,4,6-trien-6,9-diyl diacetate (458 mg).

IR $\nu_{max}^{CHCl_3}$: 3525, 3430, 1762, 1723, 1672, 1583 cm$^{-1}$
SI Mass: m/z 586 (M$^+$+1)

EXAMPLE 45

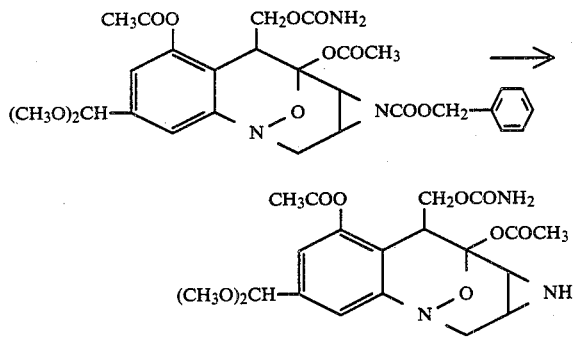

To a solution of 11-benzyloxycarbonyl-8-carbamoyloxymethyl-4-dimethoxymethyl-14-oxa-1,11-diazatetracyclo[7.4.1.0$^{2,7}$.0$^{10,12}$]tetradeca-2,4,6-trien-6,9-diyl diacetate (100 mg) in methanol (10 ml) was added 10% palladium on carbon (50 mg). The mixture was stirred for 1 hour under hydrogen atmosphere (20 psi) at ambient temperature. The reaction mixture was filtered through cellulose powder and the filtrate was evaporated in vacuo. The residue was subjected to preparative thin layer chromatography, which was developed with a mixture of chloroform and methanol (10:1, v/v) to afford A-isomer of 8-carbamoyloxymethyl-4-dimethoxymethyl-14-oxa-1,11-diazatetracyclo[7.4.1.0$^{2,7}$.0$^{10,12}$]tetradeca-2,4,6-trien-6,9-diyl diacetate (31 mg).

$^1$H NMR δ (ppm, CDCl$_3$): 6.95 (1H, s), 6.77 (1H, s), 5.37 (1H, s), 4.63 (2H, broad s), 4.34 (2H, d, J=6 Hz), 3.99 (1H, dd, J=3, 15 Hz), 3.83 (1H, t, J=6 Hz), 3.61 (1H, d, J=15 Hz), 3.30 (6H, s), 3.0–3.2 (1H), 2.35 (3H, s), 2.22 (3H, s)

IR $\nu_{max}^{CHCl_3}$: 3540, 3440, 1740, 1585 cm$^{-1}$
SI Mass: m/z 452 (M$^+$+1)

Further, B-isomer of 8-carbamoyloxymethyl-4-dimethoxymethyl-14-oxa-1,11-diazatetracyclo[7.4.1.0$^{2,7}$.0$^{10,12}$]tetradeca-2,4,6-trien-6,9-diyl diacetate (41 mg) could be afforded from the same preparative thin layer chromatography.

$^1$H NMR δ (ppm, CDCl$_3$): 6.94 (1H, s), 6.86 (1H, s), 5.30 (1H, s), 4.5–5.0 (4H), 4.25 (1H, dd, J=3.2, 7.2 Hz), 3.91 (1H, dd, J=2.7, 14.4 Hz), 3.61 (1H, dd, J=6.3, 14.4 Hz), 3.31 (6H, s), 2.77 (1H, d, J=6.3 Hz), 2.3–2.5 (1H), 2.31 (3H, s), 2.12 (3H, s)
IR $\nu_{max}^{CHCl_3}$: 3525, 3405, 2982, 1752, 1728, 1576 cm$^{-1}$
SI Mass: m/z 452 (M$^+$+1)

EXAMPLE 46

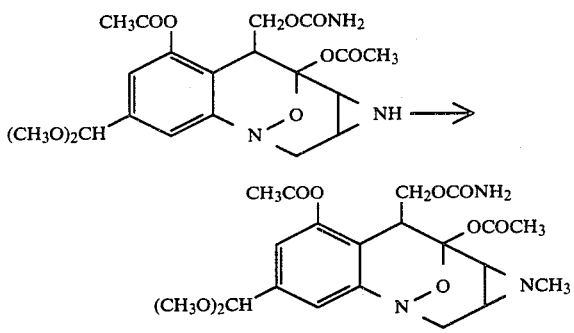

To a suspension of sodium hydride (60% in oil, 4 mg) in tetrahydrofuran (0.5 ml) was added a solution of B-isomer of 8-carbamoyloxymethyl-4-dimethoxymethyl-14-oxa-1,11-diazatetracyclo[7.4.1.0$^{2,7}$.0$^{10,12}$]tetradeca-2,4,6-trien-6,9-diyl diacetate (20 mg) in tetrahydrofuran (2.0 mg) in an ice-water bath. To this solution was added methyl iodide (0.4 ml) in an ice-water bath. After stirring for 3 hours at ambient temperature, acetic acid (0.1 ml) was added to the reaction mixture in an ice-water bath. The resultant mixture was evaporated in vacuo and the residual oil was subjected to preparative thin layer chromatography, which was developed with a mixture of chloroform and methanol (8:1, v/v) to afford 8-carbamoyloxymethyl-4-dimethoxymethyl-11-methyl-14-oxa-1,11-diazatetracyclo[7.4.1.0$^{2,7}$.0$^{10,12}$]tetradeca-2,4,6-trien-6,9-diyl diacetate (11 mg).

$^1$H NMR δ (ppm, CDCl$_3$): 6.92 (1H, d, J=1 Hz), 6.84 (1H, d, J=1 Hz), 5.32 (1H, s), 4.82 (1H, dd, J=3.2, 11.9 Hz), 4.76 (1H, dd, J=6.8, 11.9 Hz), 4.59 (2H, broad s), 4.13 (1H, dd, J=3.2, 6.8 Hz), 3.93 (1H, dd, J=2.7, 14.9 Hz), 3.66 (1H, dd, J=6.8, 14.9 Hz), 3.323 (3H, s), 3.315 (3H, s), 2.41 (3H, s), 2.32 (3H, s), 2.25–2.35 (2H), 2.19 (3H, s)
IR $\nu_{max}^{KBR}$: 3335, 2895, 1740, 1720 cm$^{-1}$
SI Mass: m/z 466 (M$^+$+1), 488 (M$^+$+23)

EXAMPLE 47

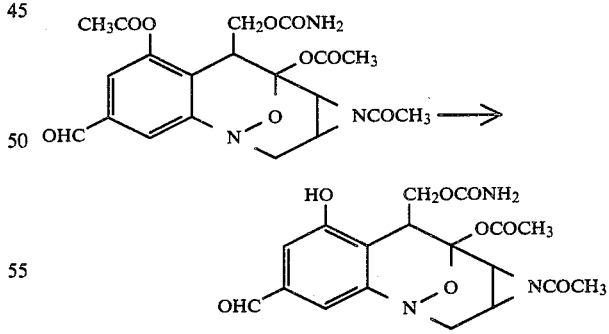

To a solution of 11-acetyl-8-carbamoyloxymethyl-4-formyl-14-oxa-1,11-diazatetracyclo[7.4.1.0$^{2,7}$.0$^{10,12}$]tetradeca-2,4,6-trien-6,9-diyl diacetate (52 mg) in methanol (5 ml) was added sodium bicarbonate (10 mg) in an ice-water bath. The mixture was stirred for 30 minutes in an ice-water bath and for additional 2.5 hours at ambient temperature. To the reaction mixture was added acetic acid to adjust the pH value to about 6 in an ice-water bath and the mixture was evaporated in vacuo. The residue was extracted with a mixture of chloroform and methanol (5:1, v/v) (5 ml×3). The extracts were combined and evaporated in vacuo. The residue was subjected to silica gel column chromatography and elution was carried out with a mixture of chloroform and methanol (50:1, v/v) to afford 11-acetyl-8-carbamoyloxymethyl-4-formyl-6-hydroxy-14-oxa-1,11-diazatetracyclo[7.4.1.0$^{2,7}$.0$^{10,12}$]tetradeca-2,4,6-trien-9-yl acetate (26 mg).

$^1$H NMR δ (ppm, CD$_3$OD): 9.80 (1H, s), 7.00 (1H, d, J=2 Hz), 6.83 (1H, d, J=2 Hz), 4.46 (1H, dd, J=7.2, 11.7 Hz), 4.14 (1H, dd, J=2, 11.7 Hz), 3.7–4.0 (3H, m), 3.60 (1H, d, J=6.3 Hz), 2.90 (1H, m), 2.18 (3H, s), 1.88 (3H, s)

EXAMPLE 48

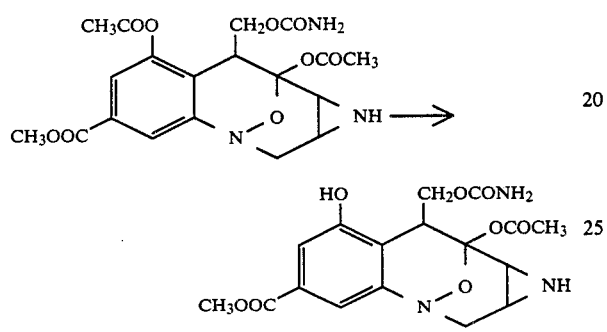

Methyl 9-acetoxy-8-carbamoyloxymethyl-6-hydroxy-14-oxa-1,11-diazatetracyclo[7.4.1.0$^{2,7}$.0$^{10,12}$]tetradeca-2,4,6-triene-4-carboxylate can be obtained according to a similar manner to that of Example 47.

$^1$H NMR δ (ppm, CDCl$_3$): 7.29 (1H, d, J=1.4 Hz), 6.97 (1H, d, J=1.4 Hz), 4.86 (2H, broad s), 4.26 (1H, dd, J=7.3. 13 Hz), 4.20 (1H, dd, J=2.4, 13 Hz), 4.08 (1H, dd, J=2.4, 7.3 Hz), 3.97 (1H, dd, J=2.2, 14 Hz), 3.86 (3H, s), 3.68 (1H, d, J=14 Hz), 3.10 (1H, m), 2.26 (1H), 2.24 (3H, s)

IR ν$_{max}^{CHCl3}$: 3555, 3445, 3325, 1744, 1720, 11715, 1584, 1358 cm$^{-1}$

EXAMPLE 49

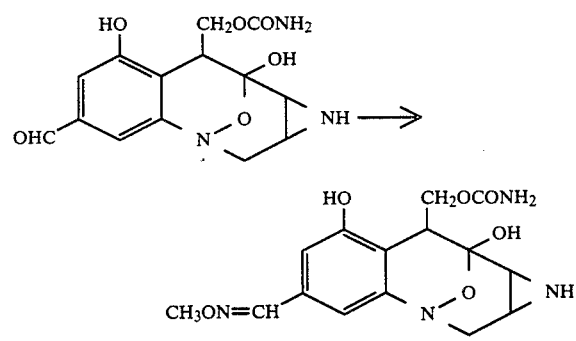

To a solution of 4-formyl-6,9-dihydroxy-14-oxa-1,11-diazatetracyclo[7.4.1.0$^{2,7}$.0$^{10,12}$]tetradeca-2,4,6-trien-8-ylmethyl carbamate (100 mg) in methanol (5 ml) were added O-methylhydroxylamine hydrochloride (105 mg) and sodium bicarbonate (106 mg). The mixture was stirred for 1.5 hours at ambient temperature and evaporated in vacuo. The residue was subjected to preparative thin layer chromatography, which was developed with a mixture of chloroform and methanol (4:1, v/v) to afford 6,9-dihydroxy-4-methoxyiminomethyl-14-oxa-1,11-diazatetracyclo[7.4.1.0$^{2,7}$.0$^{10,12}$]tetradeca-2,4,6-trien-8-ylmethyl carbamate (80 mg).

$^1$H NMRδ (ppm, CD$_3$OD): 7.94 (1H, s),
6.77(d) } (1H, J=2Hz), 6.55(d) } (1H, J=2Hz),
6.73(d) 6.47(d)
5.0–5.3 (1H), 4.4–4.8 (2H), 3.90 (3H, s), 3.5–3.8 (2H), 2.3–2.7 (2H)

IR ν$_{max}^{KBr}$: 3250, 1680, 1600 cm$^{-1}$

EXAMPLE 50

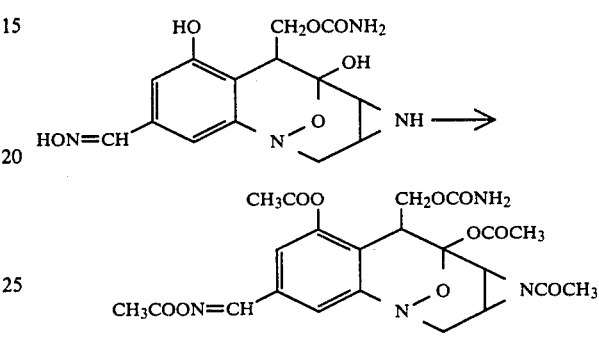

6,9-Dihydroxy-4-hydroxyiminomethyl-14-oxa-1,11-diazatetracyclo[7.4.1.0$^{2,7}$.0$^{10,12}$]tetradeca-2,4,6-trien-8-ylmethyl carbamate (88 mg) was dissolved in a mixture of pyridine (3 ml) and acetic anhydride (1.5 ml) and the solution was stirred for 20 hours at ambient temperature. The mixture was evaporated in vacuo and subjected to preparative thin layer chromatography, which was developed with a mixture of chloroform and methaol (12:1, v/v) to afford 4-acetoxyiminomethyl-11-acetyl-8-carbamoyloxymethyl-14-oxa-1,11-diazatetracyclo[7.4.1.0$^{2,7}$.0$^{10,12}$]tetradeca-2,4,6-trien-6,9-diyl diacetate (90 mg).

$^1$H NMR δ (ppm, CDCl$_3$): 8.23 (1H, s), 7.15 (1H, d, J=2 Hz), 7.02 (1H, d, J=2 Hz), 4.68 (2H, broad s), 4.2–4.6 (2H, m), 4.02 (1H, dd, J=3, 14 Hz), 3.7–3.9 (1H, m), 3.70 (1H, d, J=14 Hz), 3.39 (1H, d, J=6 Hz), 2.80 (1H, dd, J=3, 6 Hz), 2.34 (3H, s), 2.20 (6H, s), 1.95 (3H, s)

IR ν$_{max}^{CHCl3}$: 3510, 3405, 2990, 1760, 1732, 1715, 1700 cm$^{-1}$

EXAMPLE 51

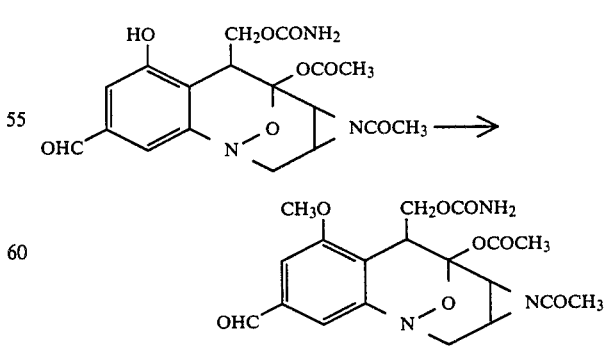

To a solution of 11-acetyl-8-carbamoyloxymethyl-4-formyl-6-hydroxy-14-oxa-1,11-diazatetracyclo[7.4.1.0$^{2,7}$.0$^{10,12}$]tetradeca-2,46-trien-9-yl acetate (25 mg) in a mixture of acetone (1 ml) and methyl iodide (1 ml) was added potassium carbonate (50 mg), and the mixture was stirred for 3 hours at 45° C. The reaction mixture was subjected to preparative thin layer chromatography, which was developed with a mixture of chloroform and methanol (15:1, v/v) to afford 11-acetyl-8-carbamoyloxymethyl-4-formyl-6-methoxy-14-oxa-1,11-diazatetracyclo[7.4.1.0$^{2,7}$.0$^{10,12}$]tetradeca-2,4,6-trien-9-yl acetate (25 mg).

$^1$H NMR δ (ppm CDCl$_3$): 9.89 (1H, s), 7.06 (1H, d, J=1 Hz), 6.87 (1H, d, J=1 Hz), 4.73 (2H, broad s), 4.52 (1H, dd, J=7, 11 Hz), 4.32 (1H, dd, J=2, 11 Hz), 4.03 (1H, dd, J=2, 14 Hz), 3.92 (3H, s), 3.87 (1H, dd, J=2, 7 Hz), 3.68 (1H, d, J=14 Hz), 3.44 (1H, d, J=6 Hz), 2.82 (1H, dd, J=2, 6 Hz), 2.20 (3H, s), 1.90 (3H, s)

IR ν$_{max}^{CHCl_3}$: 3525, 3410, 2995, 1732, 1720, 1687 cm$^{-1}$

EXAMPLE 52

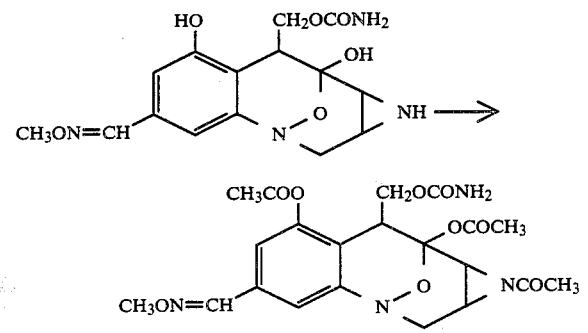

6,9-Dihydroxy-4-methoxyiminomethyl-14-oxa-1,11-diazatetracyclo[7.4.1.0$^{2,7}$.0$^{10,12}$]tetradeca-2,4,6-trien-8-ylmethyl carbamate (55 mg) was dissolved in a mixture of pyridine (3 ml) and acetic anhydride (1.5 ml) and stirred for 12 hours at ambient temperature. The mixture was evaporated in vacuo and subjected to preparative thin layer chromatography, which was developed with a mixture of chloroform and methanol (20:1, v/v) to afford 11-acetyl-8-carbamoyloxymethyl-4-methoxyiminomethyl-14-oxa-1,11-diazatetracyclo[7.4.1.0$^{2,7}$.0$^{10,12}$]tetradeca-2,4,6-trien-6,9-diyl diacetate (62 mg).

$^1$H NMR δ (ppm, CDCl$_3$): 7.90 (1H, s), 7.00 (1H, d, J=1 Hz), 6.82 (1H, d, J=1 Hz), 4.80 (2H, broad s), 4.32 (2H, d, J=6 Hz), 4.00 (1H, dd, J=2, 14 Hz), 3.92 (3H, s), 3.80 (1H, t, J=6 Hz), 3.67 (1H, d, J=14 Hz), 3.37 (1H, d, J=7 Hz), 2.77 (1H, dd, J=2, 7 Hz), 2.31 (3H, s), 2.17 (3H, s), 1.94 (3H, s)

IR μ$_{max}^{CHCl_3}$: 3520, 3430, 1760, 1753, 1732, 1720, 1700 cm$^{-1}$

EXAMPLE 53

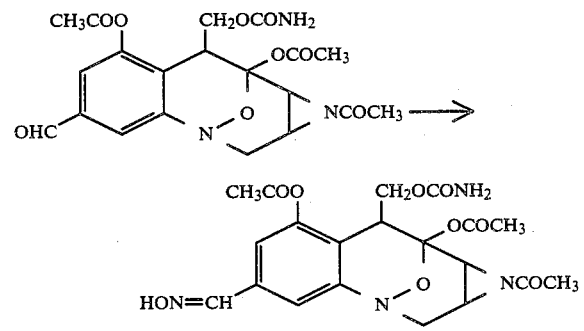

To a solution of 11-acetyl-8-carbamoyloxymethyl-4-formyl-14-oxa-1,11-diazatetracyclo[7.4.1.0$^{2,7}$.0$^{10,12}$]tetradeca-2,4,6-trien-6,9-diyl diacetate (40 mg) in methanol (2 ml) were added hydroxylamine hydrochloride (10 mg) and sodium bicarbonate (8 mg). The mixture was stirred for 2 hours at ambient temperature and evaporated in vacuo. The residue was subjected to preparative thin layer chromatography, which was developed with a mixture of chloroform and methanol (10:1, v/v) to afford 11-acetyl-8-carbamoyloxymethyl-4-hydroxyiminomethyl-14-oxa-1,11-diazatetracyclo[7.4.1.0$^{2,7}$.0$^{10,12}$]tetradeca-2,4,6-trien-6,9-diyl diacetate (13 mg).

$^1$H NMR δ (ppm, CD$_3$OD): 8.00 (1H, s), 7.03 (1H, d, J=2 Hz), 6.92 (1H, d, J=2 Hz), 4.0–4.6 (3H, m), 3.5–3.9 (3H, m), 2.87 (1H, d, J=6 Hz), 2.35 (3H, s), 2.20 (3H, s), 1.93 (3H, s)

EXAMPLE 54

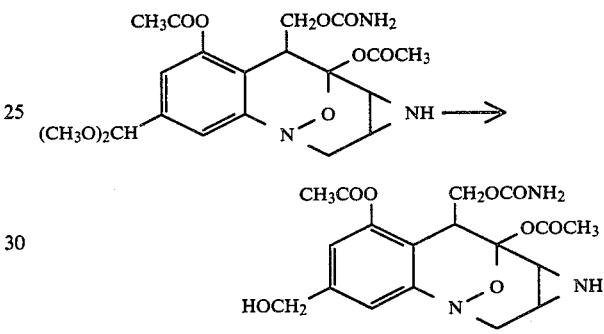

8-Carbamoyloxymethyl-4-dimethoxymethyl-14-oxa-1,11-diazatetracyclo[7.4.1.0$^{2,7}$.0$^{10,12}$]tetradeca-2,4,6-trien-6,9-diyl diacetate is reacted with p-toluenesulfonic acid according to a similar manner to that of Example 38 to give 8-carbamoyloxymethyl-4-formyl-14-oxa-1,11-diazatetracyclo[7.4.1.0$^{2,7}$.0$^{10,12}$]tetradeca-2,4,6-trien-6,9-diyl diacetate. Further, this product is subjected to catalytic reduction according to a similar manner to that of Example 17 to afford 8-carbamoyloxymethyl-4-hydroxymethyl-14-oxa-1,11-diazatetracyclo[7.4.1.0$^{2,7}$.0$^{10,12}$]tetradeca-2,4,6-trien-6,9-diyl diacetate.

$^1$H NMR δ (ppm, CDCl$_3$): 6.77 (1H, S), 6.61 (1H, S), 4.51 (2H, S), 2.97 (1H, d, J=6.3 Hz), 2.30 (3H, S), 2.14 (3H, S)

IR ν$_{max}^{CHCl_3}$: 3535, 3485, 3425, 3000, 1740, 1580 cm$^{-1}$

SI Mass: m/z 408 (M$^+$+1)

EXAMPLE 55

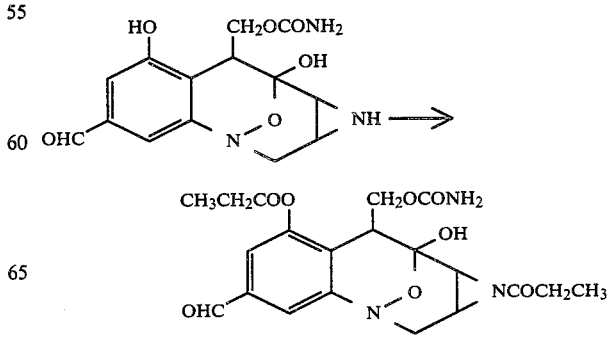

To a solution of 4-formyl-6,9-dihydroxy-14-oxa-1,11-diazatetracyclo[7.4.1.0$^{2,7}$.0$^{10,12}$]tetradeca-2,4,6-trien-8-ylmethyl carbamate (50 mg) and 4-dimethylaminopyridine (150 mg) in dimethylformamide (2 ml) was added propionyl chloride (0.1 ml) in an ice-water bath. The mixture was stirred for 20 hours at ambient temperature and evaporated in vacuo. The residue was subjected to preparative thin layer chromatography, which was developed with a mixture of chloroform and mthanol (10:1, v/v) to afford 8-carbamoyloxymethyl-4-formyl-9-hydroxy-11-propionyl-14-oxa-1,11-diazatetracyclo[7.4.1.0$^{2,7}$.0$^{10,12}$]tetradeca-2,4,6-trien-6-yl propionate (30 mg).

$^1$H NMR δ (ppm, CDCl$_3$): 9.96 (1H, S), 7.37 (2H, S), 5.00 (2H, broad S), 4.58 (1H, dd, J=5, 11 Hz), 4.2–4.5 (1H), 4.17 (1H, dd, J=6, 11 Hz), 3.5–3.8 (3H), 3.27 (1H, t, J=6 Hz), 2.82 (2H, q, J=7.2 Hz), 2.34 (2H, q, J=7.2 Hz), 1.26 (3H, t, J=7.2 Hz), 1.19 (3H, t, J=7.2 Hz)

EXAMPLE 56

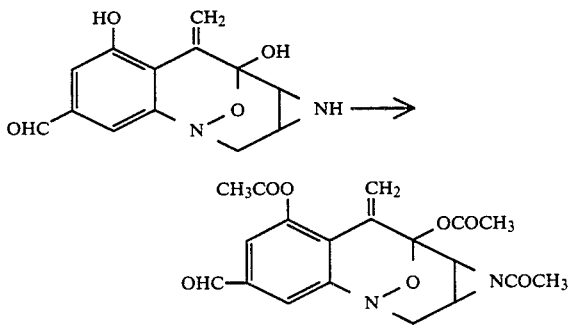

6,9-Dihydroxy-8-methylene-14-oxa-1,11-diazatetracyclo[7.4.1.0$^{2,7}$.0$^{10,12}$]tetradeca-2,4,6-triene-4-carbaldehyde (6 mg) was reacted with acetic anhydride (0.2 ml) at 80° C. according to a similar manner to that of Example 52 to afford 11-acetyl-4-formyl-8-mehtylne-14-oxa-1,11-diazatetracyclo[7.4.1.0$^{2,7}$.0$^{10,12}$]tetradeca-2,4,6-trien-6,9-diyl diacetate (4 mg).

$^1$H NMR δ (ppm, CDCl$_3$): 9.97 (1H, S), 7.40 (1H, d, J=1 Hz), 7.31 (1H, d, J=1 Hz), 6.37 (1H, S), 5.70 (1H, S), 3.5–4.2 (2H), 2.9–3.2 (2H), 2.37 (3H, S), 2.25 (3H, S), 2.22 (3H, S)

IR $\nu_{max}^{CHCl_3}$: 1772, 1700 cm$^{-1}$

EI Mass: m/z 386 (M+)

What we claim is:

1. Tetracyclo compounds of the formula:

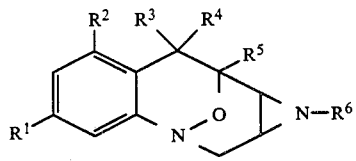

in which
R$^1$ is formyl, protected formyl, hydroxymethyl, protected hydroxymethyl, arylaminomethyl, carboxy, protected carboxy, aryliminomethyl, hydroxyiminomethyl, alkoxyiminomethyl, acyloxyiminomethyl, semicarbazonomethyl or arylsemicarbazonomethyl, R$^2$ is hydroxy, alkoxy or protected hydroxy, R$^3$ is hydrogen and R$^4$ is methyl, hydroxymethyl or protected hydroxymethyl, or R$^3$ and R$^4$ are combined together to form methylene or oxo, R$^5$ is hydroxy, alkoxy or protected hydroxy, and R$^6$ is hydrogen, imino-protective group or alkyl, and pharmaceutically acceptable salts thereof.

2. A compound of claim 1, wherein
R$^1$ is formyl, dialkoxymethyl, hydroxymethyl, acyloxymethyl, arylaminomethyl, carboxy, esterified carboxy, aryliminomethyl, hydroxyiminomethyl, alkoxyiminomethyl, acyloxyiminomethyl, semicarbazonomethyl or arylsemicarbazonomethyl, R$^2$ is hydroxy, alkoxy or acyloxy, R$^3$ is hydrogen and R$^4$ is methyl, hydroxymethyl or acyloxymethyl, or R$^3$ and R$^4$ are combined together to form methylene or oxo, R$^5$ is hydroxy, alkoxy or acyloxy, and R$^6$ is hydrogen, acyl or alkyl.

3. A compound of claim 2, wherein
R$^1$ is formyl, di(lower)alkoxymethyl, hydroxymethyl, lower alkanoyloxymethyl, arylaminomethyl, carboxy, lower alkoxycarbonyl, aryliminomethyl, hydroxyiminomethyl, lower alkoxyiminomethyl, lower alkanoyloxyiminomethyl, semicarbazonomethyl or arylsemicarbazonomethyl, R$^2$ is hydroxy, lower alkoxy, lower alkanoyloxy, higher alkanoyloxy or arylcarbamoyloxy, R$^3$ is hydrogen and R$^4$ is methyl, hydroxymethyl, carbamoyloxymethyl, lower alkanoyloxymethyl or arylcarbamoyloxymethyl, or R$^3$ and R$^4$ are combined together to form methylene or oxo, R$^5$ is hydrogen, lower alkoxy or lower alkanoyloxy, and R$^6$ is hydrogen, lower alkanoyl, higher alkanoyl, aroyl which may have halogen, lower alkylsulfonyl, aryl(lower)alkoxycarbonyl or lower alkyl.

4. A compound of claim 3, which is 4-formyl-6,9-dihydroxy-14-oxa-1,11-diazatetracyclo[7.4.1.0$^{2,7}$.0$^{10,12}$]tetradeca-2,4,6-trien-8-ylmethyl carbamate or its hydrochloride.

5. A compound of claim 3, which is 11-acetyl-8-carbamoyloxymethyl-4-formyl-14-oxa-1,11-diazatetracyclo[7.4.1.0$^{2,7}$.0$^{10,12}$]tetradeca-2,4,6-trien-6,9-diyl diacetate.

6. A compound of claim 3, which is 11-acetyl-4-formyl-9-hydroxy-8-methylene-14-oxa-1,11-diazatetracyclo[7.4.1.0$^{2,7}$.0$^{10,12}$]tetradeca-2,4,6-trien-6-yl acetate.

7. A compound of claim 3, which is 4-acetoxymethyl-11-acetyl-8-carbamoyloxymethyl-9-hydroxy-14-oxa-1,11-diazatetracyclo[7.4.1.0$^{2,7}$.0$^{10,12}$]tetradeca-2,4,6-trien-6-yl acetate.

8. A compound of claim 3, which is 4-acetoxymethyl-11-acetyl-8-carbamoyloxymethyl-14-oxa-1,11-diazatetracyclo[7.4.1.0$^{2,7}$.0$^{10,12}$]tetradeca-2,4,6-trien-6,9-diyl diacetate.

9. A compound of claim 3, which is 11-acetyl-8-carbamoyloxymethyl-4-formyl-6-methoxy-14-oxa-1,11-diazatetracyclo[7.4.1.0$^{2,7}$.0$^{10,12}$]tetradeca-2,4,6-trien-9-yl acetate.

10. A compound of claim 3, which is 11-acetyl-4-formyl-9-hydroxy-6-methoxy-14-oxa-1,11-diazatetracyclo[7.4.1.0$^{2,7}$.0$^{10,12}$]tetradeca-2,4,6-trien-8-ylmethyl carbamate.

11. A compound of claim 3, which is 6,9-dihydroxy-8-methylene-14-oxa-1,11-diazatetracyclo[7.4.1.0$^{2,7}$.0$^{10,12}$]tetradeca-2,4,6-triene-4-carbaldehyde.

12. A compound of claim 3, which is 4-acetoxymethyl-11-acetyl-9-hydroxy-8-methylene-14-oxa-1,11-diazatetracyclo[7.4.1.0$^{2,7}$.0$^{10,12}$]tetradeca-2,4,6-trien-6-yl acetate.

13. A compound of claim 3, which is 8-carbamoyloxymethyl-4-hydroxymethyl-4-oxa-1,11-diazatetracyclo[7.4.1.0$^{2,7}$.0$^{10,12}$]tetradeca-2,4,6-trien-6,9-diyl diacetate.

14. An antimicrobial pharmaceutical composition containing an antimicrobially effective amount of the tetracyclo compound of claim 1, in admixture with a pharmaceutically acceptable carrier or excipient.

15. A method for treatment of infectious diseases in mammals which comprises administering to said mammal an effective amount of the tetracyclo compound of claim 1.

* * * * *

UNITED STATES PATENT AND TRADEMARK OFFICE
CERTIFICATE OF CORRECTION

PATENT NO. : 4,645,765
DATED : February 24, 1987
INVENTOR(S) : MASANOBU KOHSAKA

It is certified that error appears in the above-identified patent and that said Letters Patent is hereby corrected as shown below:

Column 36, line 13, the formula should read

-- 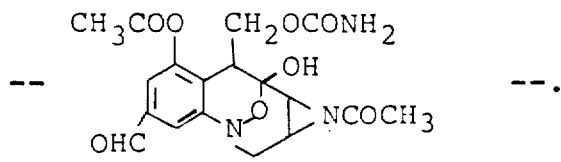 --.

Column 66, line 35, "hydrogen" should read --hydroxy--.

Column 67, line 11, "4-oxa" should read --14-oxa--.

Signed and Sealed this

Twenty-second Day of March, 1988

*Attest:*

DONALD J. QUIGG

*Attesting Officer*    *Commissioner of Patents and Trademarks*